US011065056B2

(12) United States Patent
Turquier et al.

(10) Patent No.: US 11,065,056 B2
(45) Date of Patent: Jul. 20, 2021

(54) SYSTEM AND METHOD OF GENERATING A MODEL AND SIMULATING AN EFFECT ON A SURGICAL REPAIR SITE

(71) Applicant: Sofradim Production, Trévoux (FR)

(72) Inventors: Frederic Turquier, Rhone (FR); Vit Novacek, Ain (FR); Tristan Belzacq, Ain (FR); Gaetan Guerin, Rhone (FR)

(73) Assignee: SOFRADIM PRODUCTION, Trevoux (FR)

( * ) Notice: Subject to any disclaimer, the term of this patent is extended or adjusted under 35 U.S.C. 154(b) by 447 days.

(21) Appl. No.: 15/426,088

(22) Filed: Feb. 7, 2017

(65) Prior Publication Data
US 2017/0273745 A1    Sep. 28, 2017

(30) Foreign Application Priority Data

Mar. 24, 2016    (EP) ..................................... 16305341

(51) Int. Cl.
*A61B 34/10* (2016.01)
*G16H 50/50* (2018.01)
(Continued)

(52) U.S. Cl.
CPC .............. *A61B 34/10* (2016.02); *A61B 34/25* (2016.02); *G06T 19/20* (2013.01); *G16H 50/50* (2018.01);
(Continued)

(58) Field of Classification Search
CPC ........ A61B 34/25; A61B 34/10; G16H 50/50; G06F 19/00; G06T 19/20
(Continued)

(56) References Cited

U.S. PATENT DOCUMENTS 4,290,114 A    9/1981  Sinay
4,481,001 A   11/1984  Graham et al.
(Continued)

FOREIGN PATENT DOCUMENTS

CN    105147416 A    12/2015
EP      0531889 A2    3/1993
(Continued)

OTHER PUBLICATIONS

Novitsky et al. ("Transversus abdominis muscle release: a novel approach to posterior component separation during complex abdominal wall reconstruction", The American Journal of Surgery (2012) 204, 709-716) (Year: 2012).*
(Continued)

*Primary Examiner* — Iftekhar A Khan
(74) *Attorney, Agent, or Firm* — Weber Rosselli & Cannon LLP

(57) ABSTRACT

A method of generating a computer-based observable model of an implantable repair material secured to a patient is provided. The method includes processing data corresponding to a patient using a computing device including a processor and a memory storing a software application executable by the processor. The method also includes indicating an implantable repair material and a fixation for securing the implantable repair material to the patient and indicating a distribution of the fixation about the implantable repair material. The method also includes generating an observable model of the implantable repair material secured to the patient on a display operably associated with the computing device. The observable model depicts the indicated distribution of the fixation about the implantable repair material.

27 Claims, 71 Drawing Sheets

(51) Int. Cl.
*A61B 34/00* (2016.01)
*G06T 19/20* (2011.01)
*A61F 2/00* (2006.01)

(52) U.S. Cl.
CPC ....... *A61B 2034/104* (2016.02); *A61F 2/0063* (2013.01); *G06T 2200/24* (2013.01); *G06T 2210/41* (2013.01)

(58) Field of Classification Search
USPC .......................................................... 703/6
See application file for complete search history.

(56) References Cited

U.S. PATENT DOCUMENTS

| | | | |
|---|---|---|---|
| 4,575,805 A | 3/1986 | Moermann et al. | |
| 4,839,822 A | 6/1989 | Dormond et al. | |
| 5,005,143 A | 4/1991 | Kltschuler et al. | |
| 5,018,067 A | 5/1991 | Mohlenbrock et al. | |
| 5,147,374 A * | 9/1992 | Fernandez | A61F 2/0063 606/151 |
| 5,255,187 A | 10/1993 | Sorensen | |
| 5,290,217 A | 3/1994 | Campos | |
| 5,301,105 A | 4/1994 | Cummings, Jr. | |
| 5,304,187 A | 4/1994 | Green et al. | |
| D347,061 S | 5/1994 | Phillips | |
| 5,366,460 A * | 11/1994 | Eberbach | A61B 17/0057 128/887 |
| 5,397,332 A | 3/1995 | Kammerer et al. | |
| 5,405,360 A | 4/1995 | Tovey | |
| 5,441,527 A * | 8/1995 | Erickson | A61N 1/05 607/116 |
| 5,464,403 A * | 11/1995 | Kieturakis | A61F 2/0063 128/898 |
| 5,473,537 A | 12/1995 | Glazer et al. | |
| 5,517,405 A | 5/1996 | McAndrew et al. | |
| 5,540,704 A | 7/1996 | Gordon et al. | |
| 5,551,436 A | 9/1996 | Yago | |
| 5,583,758 A | 12/1996 | McIlroy et al. | |
| 5,586,066 A | 12/1996 | White et al. | |
| 5,618,290 A | 4/1997 | Toy et al. | |
| 5,664,109 A | 9/1997 | Johnson et al. | |
| 5,737,539 A | 4/1998 | Edelson et al. | |
| 5,738,102 A | 4/1998 | Lemelson | |
| 5,752,235 A | 5/1998 | Kehr et al. | |
| 5,764,923 A | 6/1998 | Tallman et al. | |
| 5,766,231 A * | 6/1998 | Erickson | A61N 1/3605 607/51 |
| 5,769,074 A | 6/1998 | Barnhill et al. | |
| 5,772,585 A | 6/1998 | Lavin et al. | |
| 5,775,916 A | 7/1998 | Cooper et al. | |
| 5,819,248 A | 10/1998 | Kegan | |
| 5,833,599 A | 11/1998 | Schrier et al. | |
| 5,839,438 A | 11/1998 | Graettinger et al. | |
| 5,845,255 A | 12/1998 | Mayaud | |
| 5,860,917 A | 1/1999 | Comanor et al. | |
| 5,865,802 A | 2/1999 | Yoon et al. | |
| 5,908,302 A | 6/1999 | Goldfarb | |
| 5,908,383 A | 6/1999 | Brynjestad | |
| 5,924,074 A | 7/1999 | Evans | |
| 5,942,986 A | 8/1999 | Shabot et al. | |
| 6,009,420 A | 12/1999 | Fagg, III et al. | |
| 6,029,138 A | 2/2000 | Khorasani et al. | |
| 6,049,794 A | 4/2000 | Jacobs et al. | |
| 6,063,028 A | 5/2000 | Luciano | |
| 6,081,786 A | 6/2000 | Barry et al. | |
| 6,088,677 A | 7/2000 | Spurgeon | |
| 6,098,061 A | 8/2000 | Gotoh et al. | |
| 6,101,478 A | 8/2000 | Brown | |
| 6,151,581 A | 11/2000 | Kraftson et al. | |
| 6,188,988 B1 | 2/2001 | Barry et al. | |
| 6,195,612 B1 | 2/2001 | Pack-Harris | |
| 6,234,964 B1 | 5/2001 | Iliff | |
| 6,247,004 B1 | 6/2001 | Moukheibir | |
| 6,272,481 B1 | 8/2001 | Lawrence et al. | |
| 6,283,761 B1 | 9/2001 | Joao | |
| 6,317,719 B1 | 11/2001 | Schrier et al. | |
| 6,336,812 B1 | 1/2002 | Cooper et al. | |
| 6,381,577 B1 | 4/2002 | Brown | |
| 6,409,739 B1 | 6/2002 | Nobles et al. | |
| 6,443,889 B1 | 9/2002 | Groth et al. | |
| 6,447,448 B1 * | 9/2002 | Ishikawa | A61B 5/0031 600/300 |
| 6,450,956 B1 | 9/2002 | Rappaport et al. | |
| 6,463,351 B1 | 10/2002 | Clynch | |
| 6,470,320 B1 | 10/2002 | Hildebrand et al. | |
| 6,482,156 B2 | 11/2002 | Iliff | |
| 6,575,988 B2 | 6/2003 | Rousseau | |
| 6,638,218 B2 | 10/2003 | Bulat | |
| 6,658,396 B1 | 12/2003 | Tang et al. | |
| 6,678,562 B1 * | 1/2004 | Tepper | A61B 17/6416 606/54 |
| 6,678,669 B2 | 1/2004 | Lapointe et al. | |
| 6,694,334 B2 | 2/2004 | DuLong et al. | |
| 6,770,029 B2 | 8/2004 | Iliff | |
| 6,772,026 B2 | 8/2004 | Bradbury et al. | |
| 6,804,656 B1 | 10/2004 | Rosenfeld et al. | |
| 6,807,531 B1 | 10/2004 | Kanai | |
| 6,875,176 B2 | 4/2005 | Mourad et al. | |
| 6,983,423 B2 | 1/2006 | Dvorak et al. | |
| 7,026,121 B1 | 4/2006 | Wohlgemuth et al. | |
| 7,039,628 B2 | 5/2006 | Logan, Jr. | |
| 7,069,227 B1 | 6/2006 | Lintel, III et al. | |
| 7,074,183 B2 | 7/2006 | Castellanos | |
| 7,158,890 B2 | 1/2007 | Brumbach et al. | |
| 7,181,017 B1 | 2/2007 | Nagel et al. | |
| 7,230,529 B2 | 6/2007 | Ketcherside, Jr. et al. | |
| 7,239,937 B2 | 7/2007 | Slemker et al. | |
| 7,251,610 B2 | 7/2007 | Alban et al. | |
| 7,256,708 B2 | 8/2007 | Rosenfeld et al. | |
| 7,275,220 B2 | 9/2007 | Brummel et al. | |
| 7,319,386 B2 | 1/2008 | Collins, Jr. et al. | |
| 7,356,379 B2 | 4/2008 | Slemker et al. | |
| 7,364,544 B2 | 4/2008 | Castellanos | |
| 7,379,885 B1 | 5/2008 | Zakim | |
| 7,409,354 B2 | 8/2008 | Putnam et al. | |
| 7,428,520 B2 | 9/2008 | Armstrong et al. | |
| 7,431,734 B2 * | 10/2008 | Danoff | A61F 2/30721 607/51 |
| 7,447,643 B1 | 11/2008 | Olson et al. | |
| 7,457,804 B2 | 11/2008 | Uber, III et al. | |
| 7,493,266 B2 | 2/2009 | Gupta | |
| 7,493,299 B2 | 2/2009 | Entwistle | |
| 7,533,008 B2 | 5/2009 | Mangino et al. | |
| 7,676,390 B2 | 3/2010 | Senturk et al. | |
| 7,702,600 B2 | 4/2010 | Deshpande | |
| 7,705,727 B2 | 4/2010 | Pestotnik et al. | |
| 7,727,142 B2 | 6/2010 | Hjelle et al. | |
| 7,742,933 B1 | 6/2010 | Royds | |
| 7,769,603 B2 | 8/2010 | Jung et al. | |
| 7,811,297 B2 | 10/2010 | Cox et al. | |
| 7,827,044 B2 | 11/2010 | McCullough | |
| 7,844,470 B2 | 11/2010 | Portnoy et al. | |
| 7,850,454 B2 | 12/2010 | Toly | |
| 7,869,984 B2 | 1/2011 | Mangino et al. | |
| 7,874,985 B2 | 1/2011 | Kovatchev et al. | |
| 7,877,272 B2 | 1/2011 | Rosales et al. | |
| 7,962,855 B2 | 6/2011 | Lengeling | |
| 7,970,725 B2 | 6/2011 | Armstrong et al. | |
| 7,991,485 B2 | 8/2011 | Zakim | |
| 7,996,381 B2 | 8/2011 | Uber, III et al. | |
| 8,046,625 B2 | 10/2011 | Ferguson et al. | |
| 8,062,331 B2 * | 11/2011 | Zamierowski | A61B 17/08 606/216 |
| 8,070,773 B2 * | 12/2011 | Zamierowski | A61B 17/064 606/216 |
| 8,078,282 B2 * | 12/2011 | Nycz | A61N 1/205 607/51 |
| 8,086,552 B2 | 12/2011 | Randazzo et al. | |
| 8,095,382 B2 | 1/2012 | Boyden et al. | |
| 8,095,384 B2 | 1/2012 | Firminger et al. | |
| 8,116,900 B2 | 2/2012 | Slemker et al. | |
| 8,121,868 B1 | 2/2012 | Grady et al. | |
| 8,135,596 B2 | 3/2012 | Jung et al. | |

(56) References Cited

U.S. PATENT DOCUMENTS

| | | |
|---|---|---|
| 8,147,537 B2 | 4/2012 | Boyden et al. |
| 8,150,709 B2 | 4/2012 | Miller et al. |
| 8,160,895 B2 | 4/2012 | Schmitt et al. |
| 8,165,896 B2 | 4/2012 | Jung et al. |
| 8,185,409 B2 | 5/2012 | Putnam et al. |
| 8,234,128 B2 | 7/2012 | Martucci et al. |
| 8,250,018 B2 | 8/2012 | Wong et al. |
| 8,265,948 B2 | 9/2012 | Schmitt et al. |
| 8,284,047 B2 | 10/2012 | Collins, Jr. et al. |
| 8,297,982 B2 | 10/2012 | Park et al. |
| 8,316,227 B2 | 11/2012 | Nolan et al. |
| 8,321,474 B2 | 11/2012 | Schilken |
| 8,346,698 B2 | 1/2013 | Baluta |
| 8,380,539 B2 | 2/2013 | Linder et al. |
| 8,380,542 B2 | 2/2013 | Wons et al. |
| 8,384,526 B2 | 2/2013 | Schuman, Sr. et al. |
| 8,392,747 B2 | 3/2013 | Ferguson et al. |
| 8,417,537 B2 | 4/2013 | Apacible et al. |
| 8,421,606 B2 | 4/2013 | Collins, Jr. et al. |
| 8,430,922 B2 | 4/2013 | Jung et al. |
| 8,448,077 B2 | 5/2013 | Alsafadi |
| 8,456,286 B2 | 6/2013 | Schuman et al. |
| 8,461,968 B2 | 6/2013 | Ball et al. |
| 8,468,029 B2 | 6/2013 | Jung et al. |
| 8,469,716 B2 | 6/2013 | Fedotov et al. |
| 8,475,517 B2 | 7/2013 | Jung et al. |
| 8,478,437 B2 | 7/2013 | Boyden et al. |
| 8,521,552 B2 | 8/2013 | Niwa |
| 8,521,716 B2 | 8/2013 | Uber, III et al. |
| 8,527,293 B2 | 9/2013 | Hammond et al. |
| 8,532,938 B2 | 9/2013 | Jung et al. |
| 8,533,004 B1 | 9/2013 | Grady et al. |
| 8,533,746 B2 | 9/2013 | Nolan et al. |
| 8,538,778 B2 | 9/2013 | Neville |
| 8,551,155 B2 | 10/2013 | Jung et al. |
| 8,561,039 B2 | 10/2013 | Winter et al. |
| 8,589,175 B2 | 11/2013 | Glauser et al. |
| 8,598,995 B2 | 12/2013 | Schuman et al. |
| 8,604,916 B2 | 12/2013 | McNeely et al. |
| 8,604,917 B2 | 12/2013 | Collins et al. |
| 8,606,591 B2 | 12/2013 | Heniford et al. |
| 8,613,621 B2 | 12/2013 | Hendrickson et al. |
| 8,615,406 B1 | 12/2013 | Grady et al. |
| 8,636,662 B2 | 1/2014 | Gritzky |
| 8,641,699 B2 * | 2/2014 | Hansen .............. A61B 17/0057 606/1 |
| 8,645,424 B2 | 2/2014 | Miller |
| 8,661,247 B2 | 2/2014 | Spalka et al. |
| 8,666,467 B2 | 3/2014 | Lynn et al. |
| 8,666,785 B2 | 3/2014 | Baluta et al. |
| 8,677,146 B2 | 3/2014 | Spalka et al. |
| 8,688,385 B2 | 4/2014 | Mrazek et al. |
| 8,688,416 B2 | 4/2014 | Fearon et al. |
| 8,695,106 B2 | 4/2014 | Spalka et al. |
| 8,699,705 B2 | 4/2014 | Spalka et al. |
| 8,708,707 B2 | 4/2014 | Hendrickson et al. |
| 8,725,699 B2 | 5/2014 | Randazzo et al. |
| 8,728,001 B2 | 5/2014 | Lynn |
| 8,758,245 B2 | 6/2014 | Ray et al. |
| 8,762,306 B2 | 6/2014 | Cameron et al. |
| 8,762,766 B2 | 6/2014 | Ferguson et al. |
| 8,764,452 B2 | 7/2014 | Pravong et al. |
| 8,775,196 B2 | 7/2014 | Simpson et al. |
| 9,320,826 B2 * | 4/2016 | Lee ..................... A61L 24/06 |
| 9,445,883 B2 * | 9/2016 | Lecuivre ................ D06C 7/00 |
| 9,839,505 B2 * | 12/2017 | Romuald .............. A61F 2/0063 |
| 2001/0050610 A1 | 12/2001 | Gelston |
| 2001/0050810 A1 | 12/2001 | Lorincz |
| 2002/0002472 A1 | 1/2002 | Abraham-Fuchs |
| 2002/0002473 A1 | 1/2002 | Schrier et al. |
| 2002/0007294 A1 | 1/2002 | Bradbury et al. |
| 2002/0019747 A1 | 2/2002 | Ware et al. |
| 2002/0029157 A1 | 3/2002 | Marchosky |
| 2002/0035486 A1 | 3/2002 | Huyn et al. |
| 2002/0040282 A1 | 4/2002 | Bailey et al. |
| 2002/0042726 A1 | 4/2002 | Mayaud |
| 2002/0049503 A1 * | 4/2002 | Milbocker .............. C08L 75/04 623/23.72 |
| 2002/0080189 A1 | 6/2002 | Dvorak et al. |
| 2002/0083075 A1 | 6/2002 | Brummel et al. |
| 2002/0091687 A1 | 7/2002 | Eglington |
| 2002/0099273 A1 | 7/2002 | Bocionek et al. |
| 2002/0107824 A1 | 8/2002 | Ahmed |
| 2002/0116222 A1 | 8/2002 | Wurster |
| 2002/0143262 A1 | 10/2002 | Bardy |
| 2002/0169771 A1 | 11/2002 | Melmon et al. |
| 2002/0178031 A1 | 11/2002 | Sorensen et al. |
| 2003/0050802 A1 | 3/2003 | Jay et al. |
| 2003/0069752 A1 | 4/2003 | LeDain et al. |
| 2003/0110059 A1 | 6/2003 | Janas et al. |
| 2003/0125609 A1 | 7/2003 | Becker |
| 2003/0135095 A1 | 7/2003 | Iliff |
| 2003/0154109 A1 | 8/2003 | Martin et al. |
| 2003/0163348 A1 | 8/2003 | Stead et al. |
| 2003/0172940 A1 | 9/2003 | Rogers et al. |
| 2003/0236683 A1 | 12/2003 | Henderson et al. |
| 2004/0075433 A1 | 4/2004 | Kaufman |
| 2004/0130446 A1 | 7/2004 | Chen et al. |
| 2004/0204963 A1 | 10/2004 | Klueh et al. |
| 2004/0210548 A1 | 10/2004 | Ketcherside et al. |
| 2004/0225199 A1 | 11/2004 | Evanyk et al. |
| 2004/0236192 A1 * | 11/2004 | Necola Shehada .. A61B 5/6882 600/301 |
| 2004/0243481 A1 | 12/2004 | Bradbury et al. |
| 2004/0249250 A1 | 12/2004 | McGee et al. |
| 2004/0260666 A1 | 12/2004 | Pestotnik et al. |
| 2005/0020903 A1 | 1/2005 | Krishnan et al. |
| 2005/0026125 A1 | 2/2005 | Toly |
| 2005/0055242 A1 | 3/2005 | Bello et al. |
| 2005/0058629 A1 * | 3/2005 | Harmon ............. A61K 38/1833 424/93.7 |
| 2005/0080462 A1 | 4/2005 | Jenkins et al. |
| 2005/0108052 A1 | 5/2005 | Omaboe |
| 2005/0137480 A1 | 6/2005 | Alt et al. |
| 2005/0142163 A1 * | 6/2005 | Hunter ...................... A61P 1/00 424/423 |
| 2005/0143817 A1 * | 6/2005 | Hunter ............... A61B 17/1219 623/11.11 |
| 2005/0144274 A1 | 6/2005 | Osborn et al. |
| 2005/0175665 A1 * | 8/2005 | Hunter .................. A61K 45/06 424/423 |
| 2005/0203773 A1 | 9/2005 | Soto et al. |
| 2005/0215867 A1 | 9/2005 | Grigsby et al. |
| 2005/0216305 A1 | 9/2005 | Funderud |
| 2005/0245817 A1 * | 11/2005 | Clayton ................... A61B 5/06 600/424 |
| 2005/0273359 A1 | 12/2005 | Young |
| 2006/0009856 A1 * | 1/2006 | Sherman ............. A61B 5/0031 623/20.32 |
| 2006/0010090 A1 | 1/2006 | Brockway et al. |
| 2006/0036323 A1 * | 2/2006 | Carl ...................... A61F 2/4405 623/17.11 |
| 2006/0079773 A1 | 4/2006 | Mourad et al. |
| 2006/0089646 A1 * | 4/2006 | Bonutti ................. A61F 2/0811 606/279 |
| 2006/0100508 A1 * | 5/2006 | Morrison ............. A61B 5/1075 600/426 |
| 2006/0100738 A1 | 5/2006 | Alsafadi et al. |
| 2006/0129154 A1 * | 6/2006 | Shipp ................. A61B 17/0644 606/301 |
| 2006/0173715 A1 | 8/2006 | Wang |
| 2006/0206038 A1 | 9/2006 | Jenkins et al. |
| 2006/0230071 A1 | 10/2006 | Kass et al. |
| 2007/0033075 A1 | 2/2007 | Hoffman et al. |
| 2007/0112361 A1 * | 5/2007 | Schonholz ............ A61F 2/0063 606/151 |
| 2007/0112782 A1 | 5/2007 | Lobach et al. |
| 2007/0118243 A1 | 5/2007 | Schroeder et al. |
| 2007/0168223 A1 | 7/2007 | Fors et al. |
| 2007/0179562 A1 * | 8/2007 | Nycz ..................... A61N 1/205 607/51 |
| 2007/0260179 A1 * | 11/2007 | Sholev ................. A61F 2/0063 604/103 |

(56) References Cited

U.S. PATENT DOCUMENTS

| | | |
|---|---|---|
| 2007/0276694 A1 | 11/2007 | Moriyama |
| 2007/0294210 A1 | 12/2007 | Jung et al. |
| 2008/0003198 A1 | 1/2008 | Haro |
| 2008/0015894 A1 | 1/2008 | Miller et al. |
| 2008/0040151 A1 | 2/2008 | Moore |
| 2008/0082357 A1 | 4/2008 | Schmitt et al. |
| 2008/0082365 A1 | 4/2008 | Schmitt et al. |
| 2008/0109252 A1 | 5/2008 | LaFountain et al. |
| 2008/0109260 A1 | 5/2008 | Roof |
| 2008/0114617 A1* | 5/2008 | Heniford ............... G16H 50/50 705/2 |
| 2008/0161680 A1* | 7/2008 | von Jako ............... A61B 34/20 600/424 |
| 2008/0188874 A1* | 8/2008 | Henderson ....... A61B 17/00234 606/151 |
| 2008/0235057 A1 | 9/2008 | Weidenhaupt et al. |
| 2008/0243542 A1 | 10/2008 | Hammond et al. |
| 2008/0255880 A1 | 10/2008 | Beller et al. |
| 2008/0256490 A1 | 10/2008 | Lord et al. |
| 2008/0270175 A1 | 10/2008 | Rodriguez et al. |
| 2008/0286722 A1* | 11/2008 | Berckmans, III .. A61C 13/0004 433/215 |
| 2009/0089092 A1 | 4/2009 | Johnson et al. |
| 2009/0119130 A1 | 5/2009 | Kimmel et al. |
| 2009/0187419 A1 | 7/2009 | Renganathan et al. |
| 2009/0216558 A1 | 8/2009 | Reisman et al. |
| 2009/0217194 A1 | 8/2009 | Martin et al. |
| 2009/0298480 A1 | 12/2009 | Khambete et al. |
| 2010/0011302 A1 | 1/2010 | Stein et al. |
| 2010/0030231 A1* | 2/2010 | Revie ..................... A61B 34/10 606/130 |
| 2010/0076563 A1* | 3/2010 | Otto ....................... A61B 5/4528 623/20.14 |
| 2010/0083159 A1 | 4/2010 | Mountain |
| 2010/0174555 A1 | 7/2010 | Abraham-Fuchs et al. |
| 2010/0191088 A1* | 7/2010 | Anderson ............... A61B 34/20 600/373 |
| 2010/0209899 A1 | 8/2010 | Park et al. |
| 2010/0210745 A1* | 8/2010 | McDaniel ............. C09D 5/1668 521/55 |
| 2010/0235182 A1 | 9/2010 | Firminger et al. |
| 2010/0235183 A1 | 9/2010 | Firminger et al. |
| 2010/0235184 A1 | 9/2010 | Firminger et al. |
| 2010/0235185 A1 | 9/2010 | Firminger et al. |
| 2010/0235186 A1 | 9/2010 | Firminger et al. |
| 2010/0235187 A1 | 9/2010 | Firminger et al. |
| 2010/0235188 A1 | 9/2010 | Firminger et al. |
| 2010/0235189 A1 | 9/2010 | Firminger et al. |
| 2010/0235190 A1 | 9/2010 | Firminger et al. |
| 2010/0235242 A1 | 9/2010 | Firminger et al. |
| 2010/0241449 A1 | 9/2010 | Firminger et al. |
| 2010/0268057 A1 | 10/2010 | Firminger et al. |
| 2010/0280847 A1 | 11/2010 | Schaffer |
| 2010/0285082 A1 | 11/2010 | Fernandez |
| 2010/0293007 A1 | 11/2010 | Schoenberg |
| 2010/0305962 A1 | 12/2010 | Firminger et al. |
| 2011/0009960 A1* | 1/2011 | Altman .................. A61F 2/0063 623/8 |
| 2011/0035231 A1 | 2/2011 | Firminger et al. |
| 2011/0145012 A1 | 6/2011 | Nightingale et al. |
| 2011/0202361 A1 | 8/2011 | Firminger et al. |
| 2011/0210853 A1 | 9/2011 | Lord et al. |
| 2011/0212090 A1* | 9/2011 | Pedersen ............... A61P 35/00 424/133.1 |
| 2011/0251834 A1 | 10/2011 | Fearon et al. |
| 2011/0288566 A1* | 11/2011 | Kubiak .................... A61F 2/08 606/151 |
| 2011/0295565 A1* | 12/2011 | Ozen .................... A61B 17/80 703/1 |
| 2011/0301977 A1 | 12/2011 | Belcher et al. |
| 2012/0011180 A1 | 1/2012 | Kavaklioglu |
| 2012/0015337 A1 | 1/2012 | Hendrickson et al. |
| 2012/0015339 A1 | 1/2012 | Hendrickson et al. |
| 2012/0029538 A1* | 2/2012 | Reeser ................ A61B 17/064 606/151 |
| 2012/0041774 A1 | 2/2012 | Schmitt et al. |
| 2012/0046966 A1 | 2/2012 | Chang et al. |
| 2012/0065986 A1 | 3/2012 | Tesanovic et al. |
| 2012/0078062 A1 | 3/2012 | Bagchi et al. |
| 2012/0095313 A1 | 4/2012 | Reinke et al. |
| 2012/0148994 A1 | 6/2012 | Hori et al. |
| 2012/0150204 A1* | 6/2012 | Mortarino ............. A61F 2/0059 606/151 |
| 2012/0150498 A1 | 6/2012 | Shastri et al. |
| 2012/0150555 A1 | 6/2012 | Truyen et al. |
| 2012/0173260 A1 | 7/2012 | Nayak et al. |
| 2012/0179175 A1* | 7/2012 | Hammell ............... D04B 21/16 606/151 |
| 2012/0179491 A1 | 7/2012 | Liu et al. |
| 2012/0191465 A1 | 7/2012 | Xue et al. |
| 2012/0232930 A1 | 9/2012 | Schmidt et al. |
| 2012/0239597 A1 | 9/2012 | Lakshminarayan |
| 2012/0253848 A1 | 10/2012 | Gazula |
| 2012/0278095 A1 | 11/2012 | Homchowdhury et al. |
| 2012/0282584 A1 | 11/2012 | Millon et al. |
| 2012/0290322 A1 | 11/2012 | Bergman et al. |
| 2013/0018393 A1* | 1/2013 | Bengtson ......... A61B 17/07207 606/144 |
| 2013/0066820 A1 | 3/2013 | Apte et al. |
| 2013/0093829 A1* | 4/2013 | Rosenblatt ............... H04N 7/14 348/14.01 |
| 2013/0116711 A1 | 5/2013 | Altman et al. |
| 2013/0116785 A1 | 5/2013 | Altman et al. |
| 2013/0151516 A1 | 6/2013 | Park |
| 2013/0185231 A1 | 7/2013 | Baras et al. |
| 2013/0245681 A1* | 9/2013 | Straehnz ............. A61B 17/064 606/219 |
| 2013/0267970 A1* | 10/2013 | Cardinale ............. A61F 2/0063 606/151 |
| 2013/0296642 A1 | 11/2013 | Atasoy et al. |
| 2013/0317844 A1 | 11/2013 | Hammond et al. |
| 2013/0325502 A1 | 12/2013 | Robicsek et al. |
| 2014/0025393 A1 | 1/2014 | Wang et al. |
| 2014/0046889 A1 | 2/2014 | Biem et al. |
| 2014/0046890 A1 | 2/2014 | Biem et al. |
| 2014/0072941 A1 | 3/2014 | Hendrickson et al. |
| 2014/0088619 A1* | 3/2014 | Cardinale ............. A61F 2/0063 606/151 |
| 2014/0123061 A1 | 5/2014 | Bennett et al. |
| 2014/0257348 A1* | 9/2014 | Priewe ................... A61F 2/0063 606/151 |
| 2014/0276999 A1* | 9/2014 | Harms ................... A61F 2/0063 606/151 |
| 2014/0342334 A1* | 11/2014 | Black ..................... G09B 23/30 434/269 |
| 2015/0057762 A1* | 2/2015 | Harms ..................... B29C 43/18 623/23.74 |
| 2015/0142023 A1* | 5/2015 | Tannhauser ........... A61F 2/0063 606/151 |
| 2015/0165096 A1* | 6/2015 | Andjelic ................. A61L 31/06 525/411 |
| 2015/0231183 A1* | 8/2015 | Peterson ................ A61P 19/02 424/569 |
| 2016/0354192 A1* | 12/2016 | Sniffin .................. A61B 17/083 |
| 2017/0105724 A1* | 4/2017 | Limem ............... A61B 17/0401 |
| 2017/0209251 A1* | 7/2017 | Francois .............. A61F 2/0063 |
| 2017/0224460 A1* | 8/2017 | Ringo .................... A61F 2/0077 |

FOREIGN PATENT DOCUMENTS

| | | |
|---|---|---|
| EP | 0718784 B1 | 8/2003 |
| EP | 2365458 A2 | 9/2011 |
| EP | 2457914 B1 | 8/2014 |
| GB | 2336008 A | 10/1999 |
| JP | H11219297 A | 8/1999 |
| JP | 2001212088 A | 8/2001 |
| JP | 2002065614 A | 3/2002 |
| JP | 2002083066 A | 3/2002 |
| JP | 2002245578 A | 8/2002 |
| JP | 2002366652 A | 12/2002 |

(56) References Cited

FOREIGN PATENT DOCUMENTS

| | | | |
|---|---|---|---|
| JP | 2003319913 A | 11/2003 | |
| JP | 2005190055 A | 7/2005 | |
| JP | 2006215035 A | 8/2006 | |
| JP | 2007050247 A | 3/2007 | |
| JP | 2009075309 A | 4/2009 | |
| WO | 9802836 A2 | 1/1998 | |
| WO | 0007131 A1 | 2/2000 | |
| WO | 0007339 A1 | 2/2000 | |
| WO | 0171634 A1 | 9/2001 | |
| WO | 0233654 A1 | 4/2002 | |
| WO | 03032827 A1 | 4/2003 | |
| WO | 03104939 A2 | 12/2003 | |
| WO | 2011070463 A1 | 6/2011 | |
| WO | 2012054925 A2 | 4/2012 | |
| WO | 2013059575 A1 | 4/2013 | |
| WO | 2013074708 A1 | 5/2013 | |
| WO | 2014055125 A1 | 4/2014 | |

OTHER PUBLICATIONS

Bringman et al. ("Hernia repair: the search for ideal meshes", Springer, 2010, pp. 81-87) (Year: 2010).*

Kukleta et al. ("Efficiency and safety of mesh fixation in laparoscopic inguinal hernia repair using n-butyl cyanoacrylate: long-term bioconnpatibility in over 1,300 mesh fixations", Hernia (2012) 16:153-162) (Year: 2012).*

Tomaszewska et al. (Physical and mathematical modelling of implant-fascia system in orderto improve laparoscopic repair of ventral hernia, Clinical Biomechanics 28 (2013) 743-751) (Year: 2013).*

Jamadar et al. (Abdominal Wall Hernia Mesh Repair, American Institute of Ultrasound in Medicine, 2008, pp. 907-917) (Year: 2008).*

Carter et al. (Application of soft tissue 1nodelling to image-guided surgery, Medical Engineering & Physics 27 (2005) 893-909) (Year: 2005).*

Notification of the First Office Action issued in Chinese Patent Application No. 201710183803.9 dated Aug. 28, 2020 with English translation.

Acosta Santamaria Victor et al: "Material 1-16 model calibration from planar tension tests on porcinelinea alba", Journal of the Mechanical Behavior of Biomedical Materials, vol. 43, Dec. 13, 2014 (Dec. 13, 2014), pp. 26-34.

Extended European Search Report issued in European Application No. 16305341 dated Sep. 14, 2016, 8 pages.

* cited by examiner

| General | Comorbidities | Risk Factors | Anatomo-pathology |

Age  61
Sex  M
Weight  99  kg
Height  1.75  m
BMI  32.3  m.kg$^{-2}$
Comments

FIG. 4A

| General | Comorbidities | Risk Factors | Anatomo-pathology |
|---|---|---|---|

Diabetis Type I  [0] [1] [2] [3] [4] [5]

Diabetis Type II  [0] [1] [2] [3] [4] [5]

Cardiac disease  [0] [1] [2] [3] [4] [5]

Arterial Hypertension  [0] [1] [2] [3] [4] [5]

Pulmonary Disease  [0] [1] [2] [3] [4] [5]

Hepatic Disease  [0] [1] [2] [3] [4] [5]

Renal Disease  [0] [1] [2] [3] [4] [5]

Malignant Disease  [0] [1] [2] [3] [4] [5]

FIG. 4B

| General | Comorbidities | Risk Factors | Anatomo-pathology |
|---|---|---|---|

Aneurysm Disease [0] [1] [2] [3] [4] [5]

Collagen-related Disease [0] [1] [2] [3] [4] [5]

Personal history [0] [1] [2] [3] [4] [5]

Family history [0] [1] [2] [3] [4] [5]

Cortocisteroids [0] [1] [2] [3] [4] [5]

Immunosuppressant [0] [1] [2] [3] [4] [5]

Anticoagulant therapy [0] [1] [2] [3] [4] [5]

FIG. 4C

MUSCULAR CONTRACTIBILITY EXPERT MODULE

Deep Electromyography

Surface Electromyography

...

| Approach | Mesh | Fixations | Fixations Distribution |

Tack  　　　　　　　　　　　　Suture  　　　　　　　　　　Glue

Brand [Covidien ▶]  Brand [　　　▶]  Brand [Covidien ▶]  Brand [N/A]
Model [Absorbatack ▶]  Model [　　　▶]  Model [Velosorb ▶]  Model [N/A]
Material [PGLA]  Material [　　　]  [　　　]  Type [N/A]
Resorption [Yes]  Resorption [　　　]

| Approach | Mesh | Fixations | Fixations Distribution |
|---|---|---|---|

Tack                    Suture              Glue
Brand  | Medtronic ▶ |   Brand | N/A       |   Brand | N/A |
Model  | Absorbatack ▶|  Model | N/A       |   Model | N/A |
Material | PGLA |                           Type  | N/A |
Resorption | Yes |

| | Selection | | | | | | | | Report | | | |
|---|---|---|---|---|---|---|---|---|---|---|---|---|
| BMI | Weight | Type | Model | Size | a1 | d1 | a2 | d2 | Cardinal | Corner | All other | Date | Activity |
| 32 | 99 | Intraperitoneal | Mesh A | 18x15.5 | 1.5 | 1 | - | - | Velosorb | Velosorb | Absorbatack | 17/06/2015 | Coughing |
| 32 | 99 | Intraperitoneal | Mesh A | 18x15.5 | 1.5 | 1 | 1.5 | 1 | Absorbatack | Absorbatack | Absorbatack | 17/06/2015 | Coughing |
| 32 | 99 | Intraperitoneal | Mesh A | 18x15.5 | 1.5 | 1 | - | - | Absorbatack | Absorbatack | Absorbatack | 17/06/2015 | Coughing |
| 32 | 99 | Intraperitoneal | Mesh A | 18x15.5 | 4 | 1 | - | - | Absorbatack | Absorbatack | Absorbatack | 17/06/2015 | Coughing |

FIG. 32A

SYSTEM AND METHOD OF GENERATING A MODEL AND SIMULATING AN EFFECT ON A SURGICAL REPAIR SITE

CROSS-REFERENCE TO RELATED APPLICATIONS

This application claims benefit of and priority to European Patent Application Serial No. 16305341.6 filed Mar. 24, 2016, the disclosure of the above-identified application is hereby incorporated by reference in its entirety.

BACKGROUND

1. Technical Field

The present disclosure relates to tissue modeling technology, and in particular, utilizing tissue modeling technology to provide clinical decision support associated with surgically repairing tissue defects.

2. Background of Related Art

Implantable surgical repair devices such as meshes and sutures used in performing tissue defect repair procedures (e.g., hernia repair, incision line reinforcement, bridging, augmentation, incision line closure, etc.) are produced in a variety of sizes and material properties to fit a range of defects and patient needs. Typically, a clinician will attempt to choose the appropriate size, shape, and fixation technique associated with the repair device prior to surgery or intra-operatively with varying degrees of success. Each patient has unique needs due to the infinite variation of subject anatomy combined with the infinite variation of disease and/or risk factors. Various imaging techniques can be used for pre-operative planning to determine surgical approaches and appropriate sizing of these repair devices. However, tissue imaging techniques fail to provide tissue modeling information relating how a repair device interacts with tissue in the model during a patient activity or action. Offering clinicians a way to observe a simulation of how a mesh or suture interacts with tissue during a given patient activity would improve repair device development, surgical techniques, patient profiles, and patient and surgeon education and decrease associated tissue defect recurrence rates.

SUMMARY

According to an embodiment of the present disclosure, a method of generating a computer-based observable model of an implantable repair material secured to a patient is provided. The method includes processing data corresponding to a patient using a computing device including a processor and a memory storing a software application executable by the processor. The method also includes indicating an implantable repair material and a fixation for securing the implantable repair material to the patient and indicating a distribution of the fixation about the implantable repair material. The method also includes generating an observable model of the implantable repair material secured to the patient on a display operably associated with the computing device. The observable model depicts the indicated distribution of the fixation about the implantable repair material.

According to one aspect of the above-described embodiment, the method also includes indicating an activity to be performed by the patient and generating, on the display, a simulation of an effect of the indicated activity on the implantable repair material secured to the patient.

According to another aspect of the above-described embodiment, the effect of the indicated activity on the implantable repair material may be selected from the group consisting of a force at the fixation securing the implantable repair material to the patient, bulging of the implantable repair material, and a stress field on the implantable repair material.

According to another aspect of the above-described embodiment, the data corresponding to the patient may include a clinical profile of the patient.

According to another aspect of the above-described embodiment, at least one of the implantable repair material, the fixation, or the distribution of the fixation about the implantable repair material may be generated by the software application.

According to another aspect of the above-described embodiment, at least one of the implantable repair material, the fixation, or the distribution of the fixation about the implantable repair material may be selected through a user interface of the computing device.

According to another aspect of the above-described embodiment, the observable model may be generated in 3D.

According to another aspect of the above-described embodiment, the observable model may be generated by the software application.

According to another aspect of the above-described embodiment, the observable model may be selected through a user interface of the computing device.

According to another aspect of the above-described embodiment, the method also includes indicating a placement technique selected from the group consisting of onlay, inlay, retromuscular, preperitoneal, and intraperitoneal.

According to another aspect of the above-described embodiment, the method also includes indicating a technique for tissue release selected from the group consisting of transversus abdominis muscle release (TAR) and component separation.

According to another aspect of the above-described embodiment, the method also includes indicating a type of defect repair as one of augmentation or bridging.

According to another aspect of the above-described embodiment, the method also includes indicating a morphotype of the patient.

According to another aspect of the above-described embodiment, the method also includes indicating a surgical approach for securing the implantable repair material to the patient as one of an open surgical approach or a laparoscopic surgical approach.

According to another aspect of the above-described embodiment, generating the observable model may be based on at least one of the processed data, the indicated implantable repair material, the indicated fixation, or the indicated distribution of the fixation.

According to another aspect of the above-described embodiment, generating the simulation may be based on at least one of the processed data, the indicated implantable repair material, the indicated fixation, the indicated distribution of the fixation, or the indicated activity to be performed by the patient.

According to another aspect of the above-described embodiment, the implantable repair material may be a hernia mesh.

According to another aspect of the above-described embodiment, the fixation for securing the implantable repair material to the patient may be at least one of a tack, a suture, glue, a strap, or a staple.

According to another aspect of the above-described embodiment, the fixation for securing the implantable repair material to the patient may be a tack.

According to another aspect of the above-described embodiment, the fixation for securing the implantable repair material to the patient may be a suture.

According to another aspect of the above-described embodiment, the fixation for securing the implantable repair material to the patient may be glue.

According to another aspect of the above-described embodiment, the fixation for securing the implantable repair material to the patient may be a staple.

According to another embodiment of the present disclosure, a system is provided for generating a computer-based observable model of an implantable repair material secured to a patient. The system includes a computing device including a processor and a memory storing a software application which, when executed by the processor, cause the computing device to perform a method. The method includes processing data corresponding to a patient using the computing device and indicating an implantable repair material and a fixation for securing the implantable repair material to the patient. The method also includes indicating a distribution of the fixation about the implantable repair material and generating an observable model of the implantable repair material secured to the patient on a display operably associated with the computing device. The observable model depicts the indicated distribution of the fixation about the implantable repair material.

According to one aspect of the above-described embodiment, the method also includes indicating an activity to be performed by the patient and generating, on the display, a simulation of an effect of the indicated activity on the implantable repair material secured to the patient.

According to another embodiment of the present disclosure, a method of generating a computer-based observable model of a hernia mesh secured to a patient is provided. The method includes processing data corresponding to a patient using a computing device including a processor and a memory storing a software application executable by the processor. The method also includes indicating a hernia mesh and a distribution of a fixation about the hernia mesh for securing the hernia mesh to the patient. The method also includes generating an observable model of the hernia mesh secured to the patient on a display operably associated with the computing device. The observable model depicts the indicated distribution of the fixation about the hernia mesh.

According to one aspect of the above-described embodiment, the method also includes indicating an activity to be performed by the patient and generating, on the display, a simulation of an effect of the indicated activity on the implantable repair material secured to the patient.

According to another embodiment of the present disclosure, a method of generating a computer-based observable model of an implantable repair material secured to a patient is provided. The method includes processing data corresponding to a patient using a computing device including a processor and a memory storing a software application executable by the processor. The method also includes indicating an implantable repair material and a fixation for securing the implantable repair material to the patient. The method also includes indicating a target distribution of the fixation about the implantable repair material when an abdominal wall of the patient is deflated and generating an optimized intra-abdominal pressure (IAP) to which to insufflate the abdominal wall of the patient. The method also includes generating an optimized distribution of the fixation about the implantable repair material when the abdominal wall of the patient is inflated at the optimized IAP.

According to one aspect of the above-described embodiment, the optimized IAP may be generated based on at least one of the implantable repair material, the fixation, or the target distribution of the fixation.

According to another aspect of the above-described embodiment, the optimized IAP may be generated based on the implantable repair material.

According to another aspect of the above-described embodiment, the optimized IAP may be generated based on the fixation.

According to another aspect of the above-described embodiment, the optimized IAP may be generated based on the target distribution of the fixation.

According to another aspect of the above-described embodiment, the method also includes generating a resulting distribution of the fixation about the implantable repair material when the abdominal wall of the patient is deflated.

According to another aspect of the above-described embodiment, the method also includes generating an observable model of the implantable repair material secured to the patient on a display operably associated with the computing device. The observable model depicts at least one of the optimized distribution of the fixation when the abdominal wall of the patient is inflated at the optimized IAP or the resulting distribution of the fixation about the implantable repair material when the abdominal wall of the patient is deflated.

According to another aspect of the above-described embodiment, the resulting distribution of the fixation may be based on at least one of the implantable repair material, the fixation, the target distribution of the fixation, or the optimized distribution of the fixation.

According to another aspect of the above-described embodiment, the resulting distribution of the fixation may be based on the implantable repair material.

According to another aspect of the above-described embodiment, the resulting distribution of the fixation may be based on the fixation.

According to another aspect of the above-described embodiment, the resulting distribution of the fixation may be based on the target distribution of the fixation.

According to another aspect of the above-described embodiment, the resulting distribution of the fixation may be based on the optimized distribution of the fixation.

According to another embodiment of the present disclosure, a method of generating a computer-based observable model of an implantable repair material secured to a patient is provided. The method includes processing data corresponding to a patient using a computing device including a processor and a memory storing a software application executable by the processor. The method also includes indicating an implantable repair material and a fixation for securing the implantable repair material to the patient. The method also includes indicating a target distribution of the fixation about the implantable repair material when an abdominal wall of the patient is deflated and indicating an intra-abdominal pressure (IAP) to which to insufflate the abdominal wall of the patient. The method also includes generating an optimized distribution of the fixation about the implantable repair material when the abdominal wall of the patient is inflated at the IAP.

According to one aspect of the above-described embodiment, the method also includes generating a resulting distribution of the fixation about the implantable repair material when the abdominal wall of the patient is deflated.

According to another aspect of the above-described embodiment, the method also includes generating an observable model of the implantable repair material secured to the patient on a display operably associated with the computing device. The observable model depicts at least one of the optimized distribution of the fixation when the abdominal wall of the patient is inflated at the IAP or the resulting distribution of the fixation about the implantable repair material when the abdominal wall of the patient is deflated.

According to one aspect of the above-described embodiment, the resulting distribution of the fixation may be based on at least one of the implantable repair material, the fixation, the target distribution of the fixation, the IAP, or the optimized distribution of the fixation.

According to another aspect of the above-described embodiment, the resulting distribution of the fixation may be based on the implantable repair material.

According to another aspect of the above-described embodiment, the resulting distribution of the fixation may be based on the fixation.

According to another aspect of the above-described embodiment, the resulting distribution of the fixation may be based on the target distribution of the fixation.

According to another aspect of the above-described embodiment, the resulting distribution of the fixation may be based on the IAP.

According to another aspect of the above-described embodiment, the resulting distribution of the fixation may be based on the optimized distribution of the fixation.

According to another embodiment of the present disclosure, a method of generating a computer-based observable model of an implantable repair material secured to a patient is provided. The method includes processing data corresponding to a patient using a computing device including a processor and a memory storing a software application executable by the processor. The method also includes indicating an implantable repair material and a fixation for securing the implantable repair material to the patient. The method also includes indicating a target distribution of the fixation about the implantable repair material when an abdominal wall of the patient is inflated and indicating an intra-abdominal pressure (IAP) to which to insufflate the abdominal wall of the patient. The method also includes generating an actual distribution of the fixation about the implantable repair material when the abdominal wall of the patient is inflated at the IAP.

According to one aspect of the above-described embodiment, the method also includes generating a resulting distribution of the fixation about the implantable repair material when the abdominal wall of the patient is deflated.

According to another aspect of the above-described embodiment, the method also includes generating an observable model of the implantable repair material secured to the patient on a display operably associated with the computing device. The observable model depicts at least one of the actual distribution of the fixation when the abdominal wall of the patient is inflated at the IAP or the resulting distribution of the fixation about the implantable repair material when the abdominal wall of the patient is deflated.

According to another aspect of the above-described embodiment, the resulting distribution of the fixation may be based on at least one of the implantable repair material, the fixation, the target distribution of the fixation, the IAP, or the actual distribution of the fixation.

According to another aspect of the above-described embodiment, the resulting distribution of the fixation may be based on at least one of the implantable repair material, the fixation, the target distribution of the fixation, the IAP, or the actual distribution of the fixation.

According to another aspect of the above-described embodiment, the resulting distribution of the fixation may be based on the implantable repair material.

According to another aspect of the above-described embodiment, the resulting distribution of the fixation may be based on the fixation.

According to another aspect of the above-described embodiment, the resulting distribution of the fixation may be based on the target distribution of the fixation.

According to another aspect of the above-described embodiment, the resulting distribution of the fixation may be based on the IAP.

According to another aspect of the above-described embodiment, the resulting distribution of the fixation may be based on the actual distribution of the fixation.

According to another aspect of the above-described embodiment, the resulting distribution of the fixation may be based on the implantable repair material.

According to another aspect of the above-described embodiment, the resulting distribution of the fixation may be based on the fixation.

According to another aspect of the above-described embodiment, the resulting distribution of the fixation may be based on the target distribution of the fixation.

According to another aspect of the above-described embodiment, the resulting distribution of the fixation may be based on the IAP.

According to another aspect of the above-described embodiment, the resulting distribution of the fixation may be based on the actual distribution of the fixation.

BRIEF DESCRIPTION OF THE DRAWINGS

The present disclosure provides a system and method for clinical decision support associated with surgically repairing tissue defects.

Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

FIGS. 4A-4D are illustrations of a user interface presenting a clinical profile of the selected patient of FIG. 3;

FIG. 10C is an illustration of a user interface presenting a fixation selection process in connection with a step of selecting the open surgery plan option presented in FIG. 9A;

FIG. 12 is an illustration of a user interface presenting a mesh selection process in connection with a step of selecting a mesh conformity optimization approach presented in FIG. 11;

FIG. 13 is an illustration of a user interface presenting a fixation selection process in connection with a step of selecting a mesh conformity optimization approach presented in FIG. 11;

FIGS. 32A-32E are illustrations of a user interface showing a step of generating an analysis report of the simulations of FIGS. 30A-30C in accordance with another embodiment of the present disclosure.

DETAILED DESCRIPTION

Figure 1:
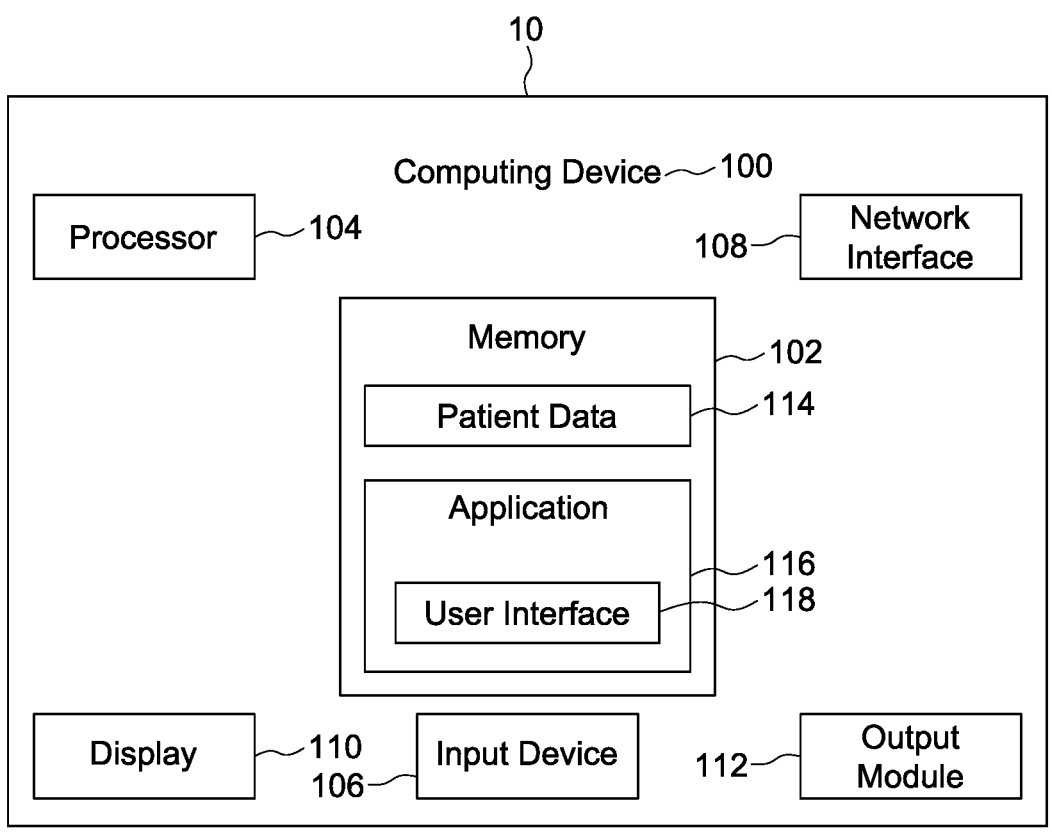
FIG. 1 is a schematic diagram of a computing device which forms part of a clinical decision support system associated with surgically repairing tissue defects.

The present disclosure provides a system and method for providing clinical decision support associated with surgically repairing tissue defects. More specifically, the system presents a clinician with a streamlined method of simulating the effects of a patient activity on a surgical repair site from the initial patient selection through a process of parameter selections to graphically generate an interactive observable 3D model of the surgical repair site on a suitable graphical display. While the term "3D" is used throughout the detailed description to describe the model, it should be understood that the generated model may be 3D, 2D, or any other suitable view. The simulation is generated on the graphical display using the generated interactive 3D model, which may be an animated depiction of patient tissue or an animated depiction of patient tissue including a defect repaired by an implantable repair material such as, for example, a suture, a mesh, or a combination thereof. The interactive 3D model is generated by the system based on a clinical profile of the patient. As described in greater detail below, a clinician may be provided an opportunity to modify the interactive 3D model generated by the system by inputting parameters through a user interface and/or by importing data from one or more suitable sources. The interactive 3D model may be displayed as patient tissue having an implantable repair material secured thereto for purposes of repairing a tissue defect in the patient tissue.

The system utilizes a software application executable on any suitable computing device to generate an observable computer simulation and provide a clinician the capability to observe the effects on an implantable repair material (e.g., a hernia mesh) secured to patient tissue, the repaired patient tissue, the patient, and/or the interaction between the implantable repair material and the tissue to which the implantable repair material is secured given the performance of a particular patient activity. Additionally, the observable computer simulation provides a clinician the capability to observe the interaction between the patient tissue and the implanted repair material. While the present disclosure to follow is described with reference to repairing hernias affecting the abdominal wall of a patient (e.g., using a ventral hernia mesh and/or sutures), the presently disclosed system is not limited to these applications in that the system is applicable to provide support for surgically repairing other types of tissue defects (e.g., inguinal, hiatal, and parastomal hernias) and performing incision line closures (FIG. 9C) with or without reinforcement using a prophylactic mesh (FIG. 10B) in connection with various pathologies such as, e.g., Chrohn's disease, gastric bypass, or splenectomy. In the instance of repairing a hernia affecting an abdominal wall using a hernia mesh, the system may use the interactive 3D model to simulate various effects such as pressure and forces on the abdominal wall, on the implanted hernia mesh, and on the fixations (e.g., tacks, sutures, glue, etc.) used to secure the hernia mesh to the abdominal wall. The system also presents a clinician with the capability to compare and contrast simulation results for different configurations of repair parameters specified by the clinician or specified by the system. For example, in the instance of hernia repair, the system may generate and display simulation results for a plurality of hernia mesh configurations each having different repair parameters (e.g., mesh type, mesh size, fixation type, fixation distribution, number of fixations, patient activity, etc.).

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Referring now to FIG. 1, the present disclosure is generally directed to a surgical repair site simulation system 10 that generally includes a computing device 100 and a software application 116 processed by the computing device 100 to generate the surgical repair site simulation and to provide a clinician with a user interface 118 to interact with the software application 116. Computing device 100 may be, for example, a laptop computer, desktop computer, tablet computer, mobile computing device, or other similar device. Computing device 100 may also include memory 102, processor 104, input device 106, network interface 108, display 110, and/or output module 112.

Memory 102 includes any non-transitory computer-readable storage media for storing data and/or software that is executable by processor 104 and which controls the operation of computing device 100. In an embodiment, memory 102 may include one or more solid-state storage devices such as flash memory chips. Alternatively or in addition to the one or more solid-state storage devices, memory 102 may include one or more mass storage devices connected to the processor 104 through a mass storage controller (not shown) and a communications bus (not shown). Although the description of computer-readable storage media contained herein refers to a solid-state storage, it should be appreciated by those skilled in the art that computer-readable storage media can be any available media that can be accessed by the processor 104. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store information and which can be accessed by computing device 100.

Memory 102 may store application 116 and/or patient data 114. Application 116 may, when executed by processor 104, cause display 110 to present user interface 118. Processor 104 may be a general purpose processor, a specialized graphics processing unit (GPU) configured to perform specific graphics processing tasks while freeing up the general purpose processor to perform other tasks, and/or any number or combination of such processors. Display 110 may be touch sensitive and/or voice activated, enabling display 110 to serve as both an input and output device. Alternatively, a keyboard (not shown), mouse (not shown), or other data input devices may be employed.

Network interface 108 may be configured to connect to a network such as a local area network (LAN) consisting of a wired network and/or a wireless network, a wide area network (WAN), a wireless mobile network, a Bluetooth network, and/or the internet. For example, computing device 100 may receive patient data from a server, for example, a hospital server, internet server, or other similar servers, for use during model generating and/or simulation. Patient data may also be provided to computing device 100 via a removable memory (not shown). Computing device 100 may receive updates to its software, for example, application 116, via network interface 108. Computing device 100 may also display notifications on display 110 that a software update is available.

Input device 106 may be any device by means of which a user may interact with computing device 100, such as, for example, a mouse, keyboard, touch screen, and/or voice interface. Output module 112 may include any connectivity port or bus, such as, for example, parallel ports, serial ports, universal serial busses (USB), or any other similar connectivity port known to those skilled in the art.

Application 116 may be one or more software programs stored in memory 102 and executed by processor 104 of computing device 100. As will be described in more detail below, application 116 guides a clinician through a series of steps to input, edit, select, deselect, indicate, and/or confirm parameters such as clinical data of a patient, biomechanical patient profiles, surgery plan parameters, and/or a patient activities for generating the interactive 3D model and simulating effects of a patient activity on a surgical repair site using the interactive 3D model.

Application 116 may be installed directly on computing device 100, or may be installed on another computer, for example a central server, and opened on computing device 100 via network interface 108. Application 116 may run natively on computing device 100, as a web-based application, or any other format known to those skilled in the art. In some embodiments, application 116 will be a single software program having all of the features and functionality described in the present disclosure. In other embodiments, application 116 may be two or more distinct software programs providing various parts of these features and functionality.

Application 116 communicates with a user interface 118 that presents visual interactive features to a clinician, for example, on display 110 and for receiving clinician input, for example, via a user input device. For example, user interface 118 may generate a graphical user interface (GUI) and output the GUI to display 110 for viewing by a clinician.

As used herein, the term "clinician" refers to any medical professional (i.e., doctor, surgeon, nurse, or the like) or other user of the surgical repair site simulation system 10 involved in interacting with the application 116 of the embodiments described herein.

Figure 2:
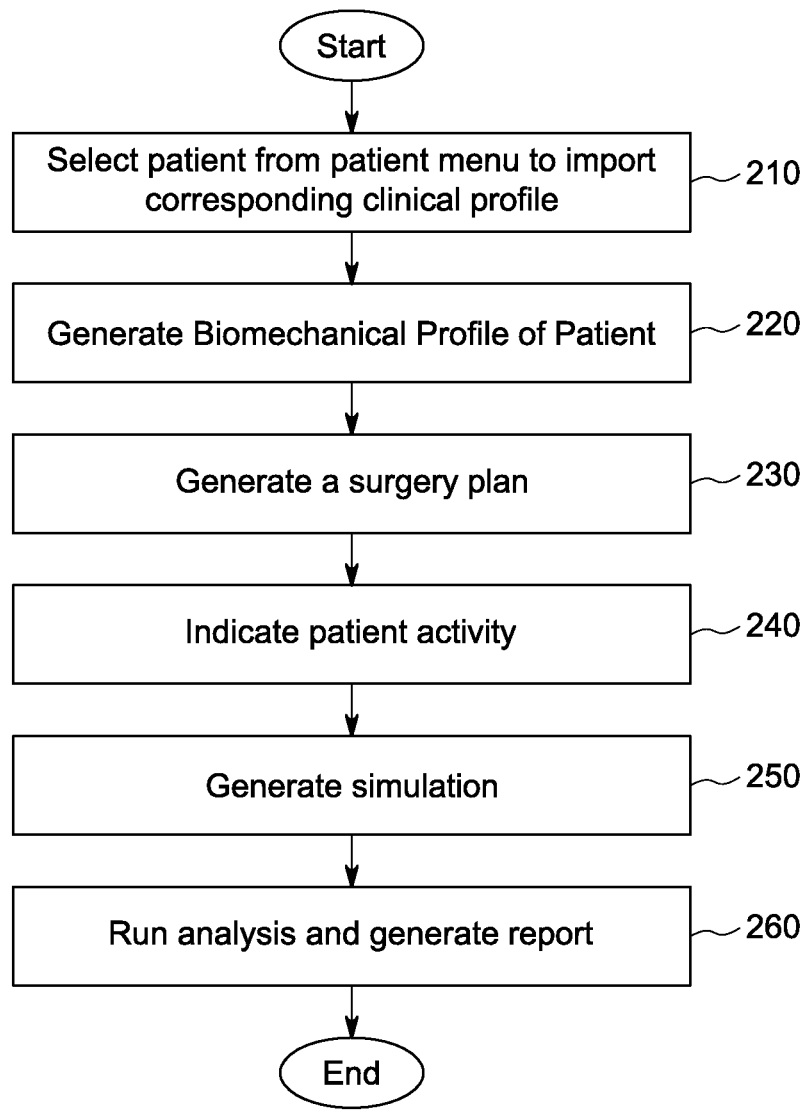
FIG. 2 is flow chart illustrating an example method of simulating the effects of a patient activity on a surgical repair site in accordance with an embodiment of the present disclosure.
Figure 3:
FIG. 3 is an illustration of a user interface presenting a view showing a step of selecting a patient from a patient menu to import a corresponding clinical profile in accordance with an embodiment of the present disclosure.

Turning now to FIG. 2, there is shown a flowchart of an example method 200 for simulating an effect of a patient activity on a surgical repair site according to an embodiment of the present disclosure. Step 210 includes selecting a patient and importing a clinical profile of that patient. With reference to FIG. 3, the system 10 may present, via the user interface 118, a list of patients from which the clinician may search for and select a patient. The list of patients may include general information such as, for example, name, age, gender, and pathology (e.g., Crohn's disease, hernia, gastric bypass, cholysectomy, splenectomy, etc.). Upon selection of a patient, a clinical profile corresponding to the selected patient is provided to the computing device 100, as described hereinabove. Once provided to the computing device 100, the clinical profile may be edited via the user interface 118.

The data included with the clinical profile provided to the computing device 100 may include data corresponding to the patient such as, for example, personal information (e.g., forename, middle name, name, age, gender, height, weight, BMI, morphotype), history information (e.g., personal history, family history), indications of disease (e.g., diabetes type, cardiac disease, arterial hypertension, pulmonary hypertension, hepatic disease, renal disease, malignant disease, aneurysm disease, collagen-related disease), indications of current medications/treatments (e.g., corticosteroids, immunosuppressant, anticoagulant therapy), pathologies, defect location, defect width, and defect height.

With reference to FIGS. 4A-4D, the clinical profile of the patient selected in step 210 is presented via the user interface 118 and may include, but is not limited to, general patient information, indications of particular comorbidities of the patient, indications of particular risk factors of the patient, an anatomo-pathology of the patient (e.g., defect width, defect height, defect type) in the case of hernia repair, and incision length and placement in the case of suturing.

With reference to FIG. 4A, the general patient information presented to the clinician via the user interface 118 may include, but is not limited to, parameters such as, for example, age, sex, weight, height, body mass index ("BMI"). These parameters are editable or confirmable by the clinician via the user interface 118. As described in detail below, a biomechanical profile of a patient (described below with respect to FIGS. 5A-8B) may be affected depending if and how a particular parameter or combination of parameters of the patient's clinical profile are edited by the clinician.

With reference to FIG. 4B, the comorbidities of the patient presented to the clinician via the user interface 118 may include, but are not limited to, diabetes type, cardiac disease, arterial hypertension, pulmonary disease, hepatic disease, renal disease, and malignant disease. For each comorbidity presented to the clinician, the clinician may indicate or confirm the severity of the comorbidity (e.g., numerically on a scale of 0-5). Although depicted in a list menu, in embodiments the comorbidity of a patient may be selected or represented in a pull down menu format or in a slide scale menu format. As described in detail below, the biomechanical profile of the patient may be affected by the indicated severity or lack of severity of a particular comorbidity or combination of comorbidities.

With reference to FIG. 4C, the risk factors of the patient presented to the clinician via the user interface 118 may include, but are not limited to, aneurysm disease, collagen-related disease, personal history such as alcohol and/or tobacco use, family history, corticosteroids, immunosuppressant, and anticoagulant therapy. For each risk factor presented to the clinician, the clinician may indicate the severity of the risk factor (e.g., numerically on a scale of 0-5). As described in detail below, the biomechanical profile of the patient may be affected by the indicated severity or lack of severity of a particular risk factor or combination of risk factors.

Figure 4D:
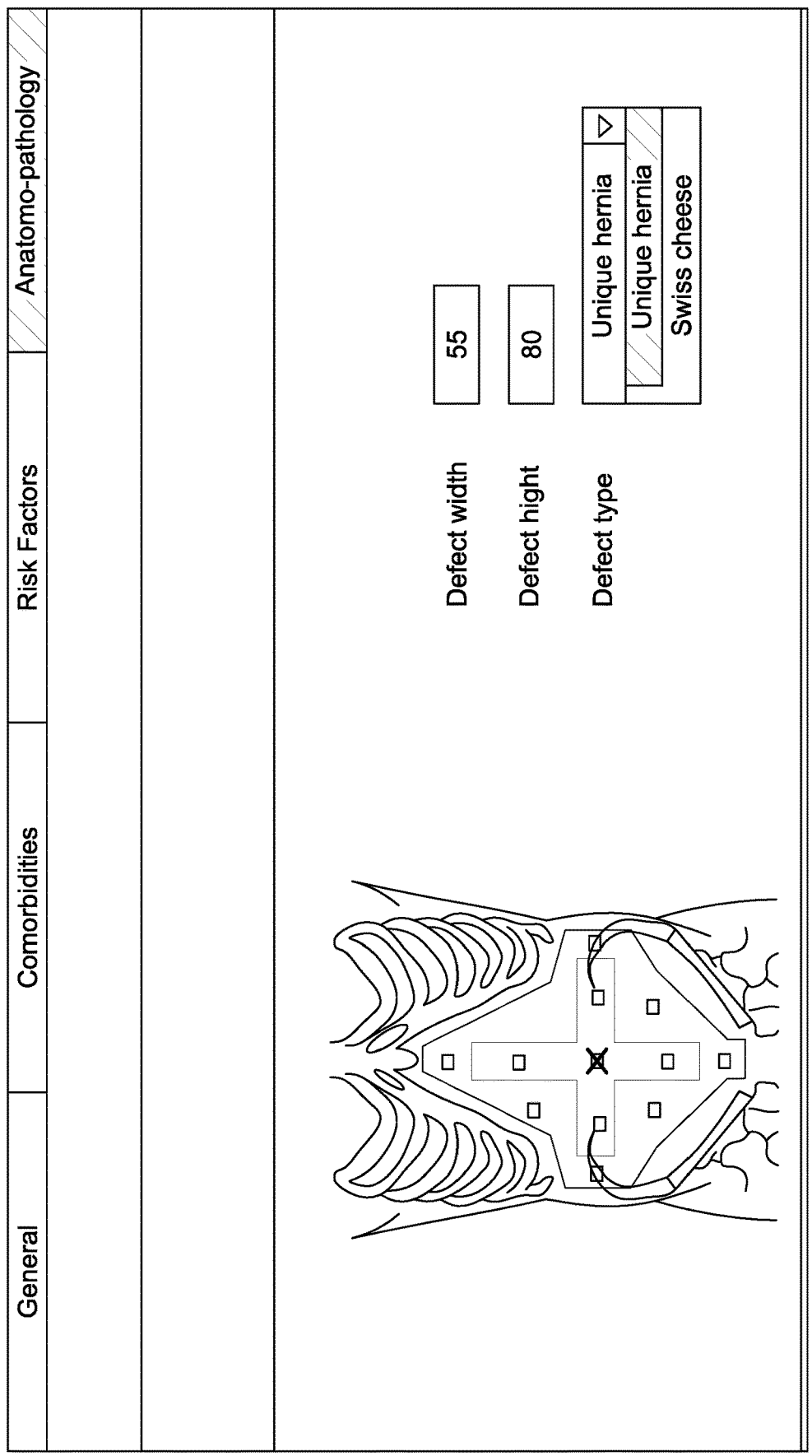

With reference to FIG. 4D, the anatomo-pathology presented to the clinician via the user interface 118 may include, but is not limited to, tissue defect width, tissue defect height, and tissue defect type (e.g., unique hernia, "swiss cheese"). As shown in FIG. 4D, the anatomo-pathology also presents to the clinician an anatomical illustration of a patient's abdominal area on which the clinician may mouse-click or touch-screen to indicate the location of a tissue defect (indicated in the illustrated example of FIG. 4D with an "x"). The clinician may also edit the indicated defect width, defect height, and defect type. As described in detail below, the biomechanical profile of the patient may be affected by the indicated defect width, height, and height or the indicated location of the tissue defect.

With continued reference to FIG. 2, step 220 includes generating a biomechanical profile of the patient based on the clinical profile of the patient. With reference to FIGS. 5A-8B, the biomechanical profile of a patient is displayed to the clinician via the user interface 118 and may include, but is not limited to, a morphotype of the patient (FIGS. 5A and 5B), an anatomical profile of the patient (FIG. 6A), tissue properties associated with the surgical repair site (FIG. 7A), and muscular contractibility associated with the surgical repair site (FIG. 8A). Other data included with the biomechanical profile of a patient may include belly depth, belly width, pubis sternum height, pubis Iliac crest distance, sternum floating rib height, rib cage angle, abdominal wall deflexion, abdominal wall flexion, fat thickness, rectus width, oblique externus thickness, oblique internus thickness, transverse abdominis thickness, and linea alba width.

The biomechanical profile of the patient may be generated by the application 116 or may be indicated, selected, and/or confirmed by the clinician through the user interface 118. As used herein, the terms "indicated," "indicating," and "indicate," may be used to describe input and/or output either generated by the application 116 or indicated, selected, specified, or confirmed through the user interface 118 (e.g., by a clinician). As described above, changes or updates to parameters of the clinical profile may affect parameters of the biomechanical profile. For example, adding tobacco use as a risk factor could lower the patient's muscle tissue quality. Tissue contractility, for example, may be affected by the severity of particular patient comorbidities such as diabetes and/or the severity of particular patient risk factors such as tobacco use.

Figure 6A:
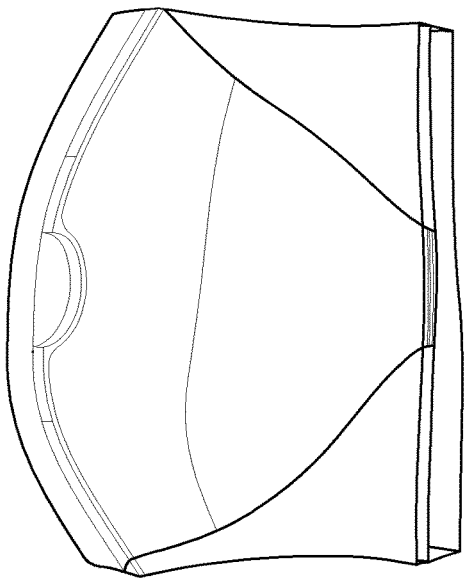
FIG. 6A is an illustration of a user interface presenting an anatomical profile in connection with a step of indicating a biomechanical profile in accordance with an embodiment of the present disclosure.
Figure 7A:
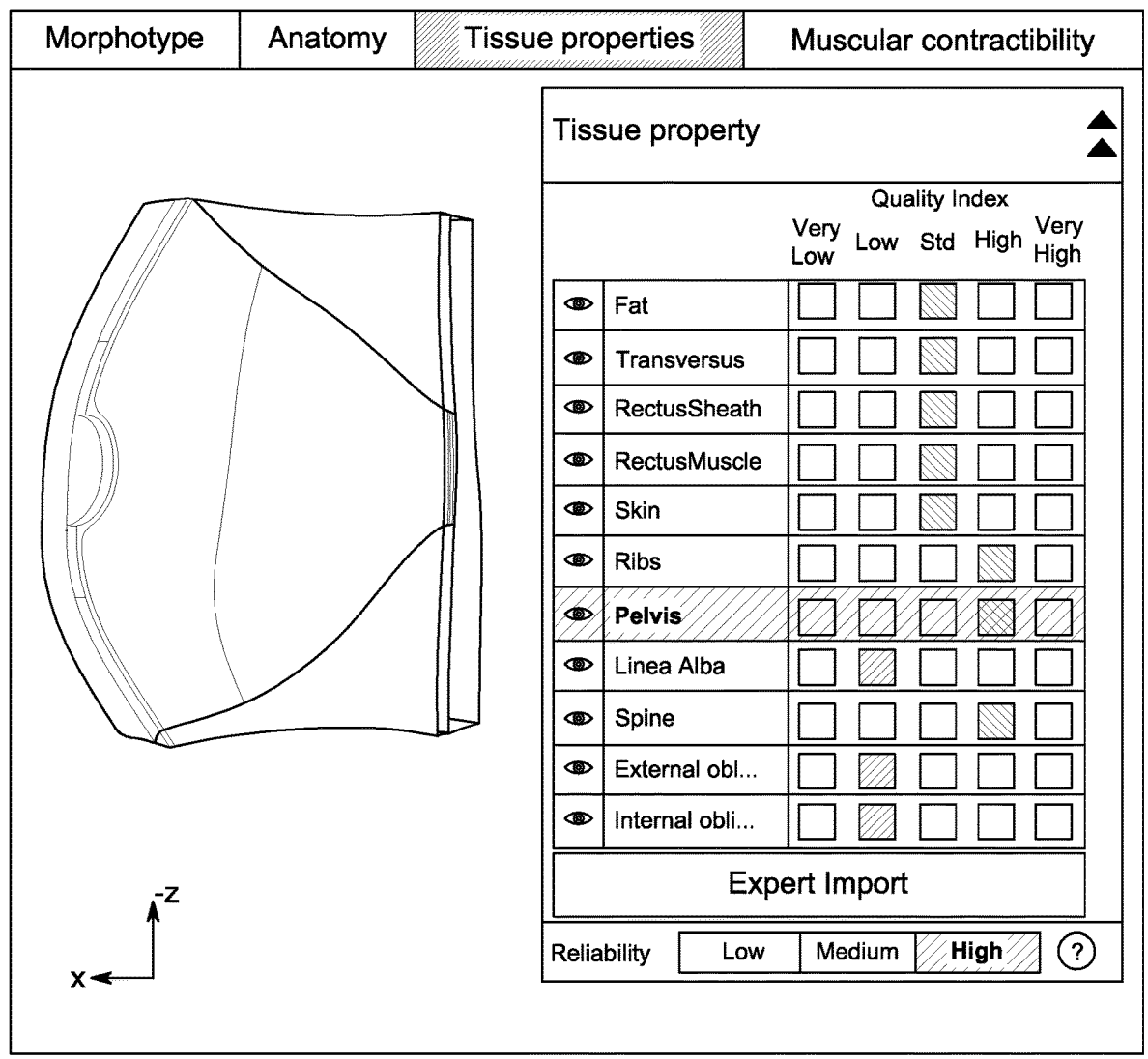
FIG. 7A is an illustration of a user interface presenting a tissue property profile in connection with a step of indicating a biomechanical profile in accordance with an embodiment of the present disclosure.
Figure 8A:
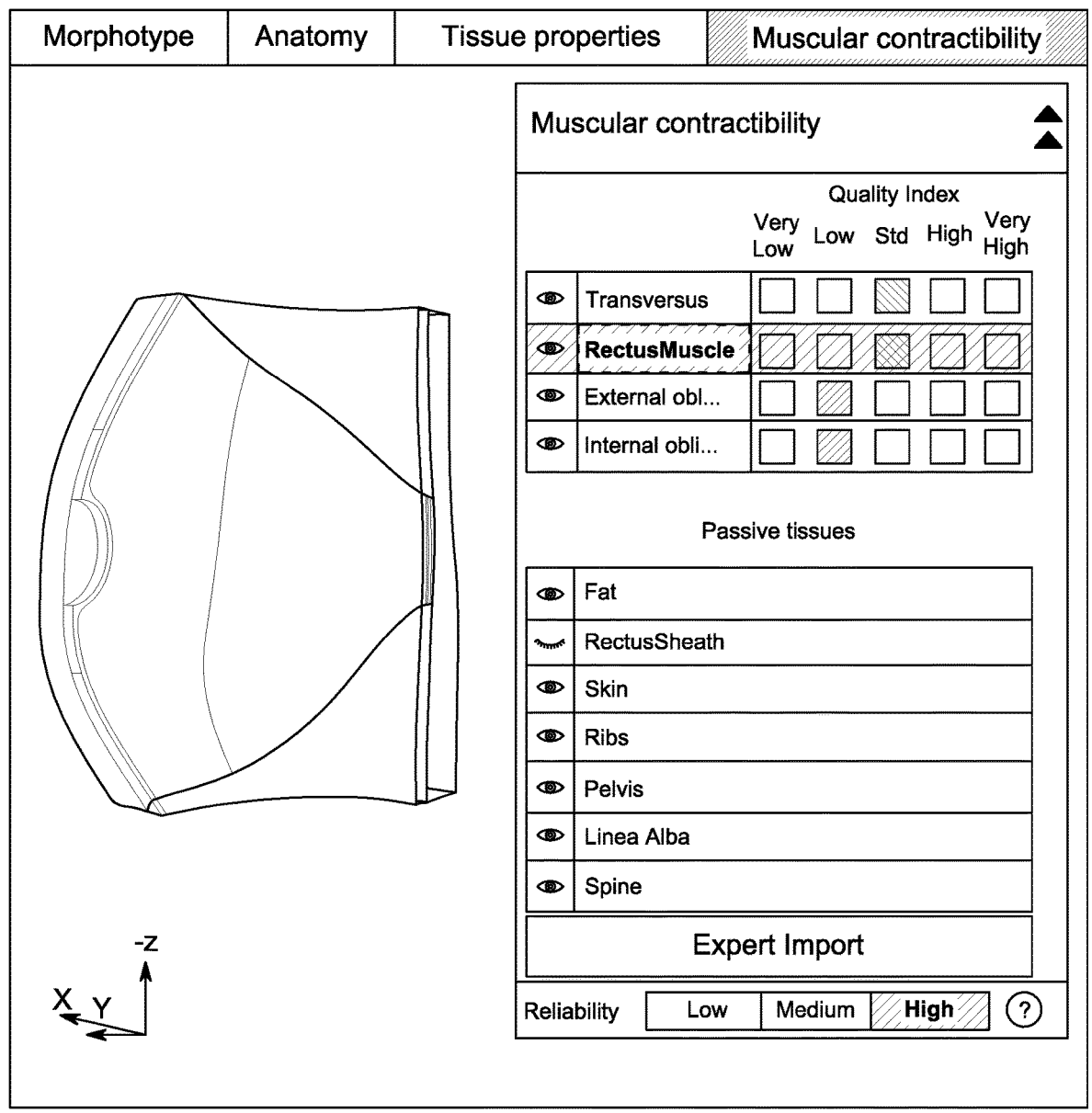
FIG. 8A is an illustration of a user interface presenting a muscular contractibility profile in connection with a step of indicating a biomechanical profile in accordance with an embodiment of the present disclosure.

As described in detail below, an interactive 3D model of a surgical repair site is generated on the display 110, as shown in FIGS. 6A, 7A, and 8A, based on the clinical profile provided in step 210. The interactive 3D model may include depictions of the patient's anatomical structures such as tissue, fat, and bone. The interactive 3D model may be interacted with and manipulated by the clinician through the user interface 118. For example, the clinician may have the capability to zoom in and out on the 3D model, rotate the 3D model about an X-Y-Z axis, and move the 3D model within the display. As described in detail below with respect to FIGS. 15A-15C, a simulation of the effects of a patient activity on a surgical repair site according to embodiments of the present disclosure is generated on the display 110 using the interactive 3D model generated in step 220, which may be an animated depiction of patient tissue including a defect repaired by an implantable repair material such as, for example, a suture, a mesh, or a combination thereof.

Figure 5A:
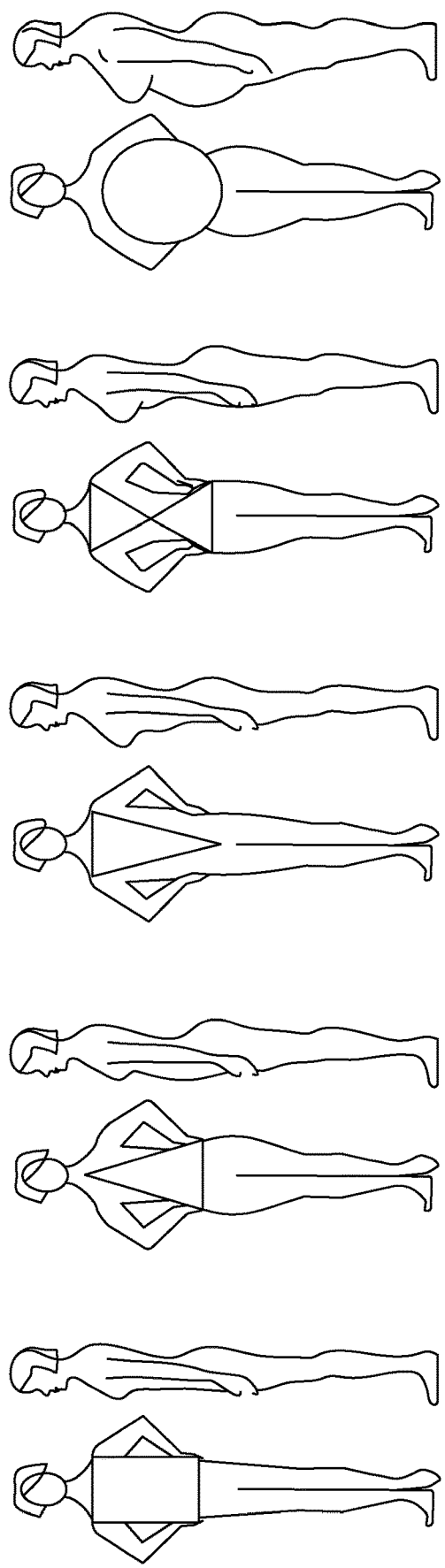
FIGS. 5A and 5B are illustrations of a user interface presenting patient morphotypes in connection with a step of indicating a biomechanical profile in accordance with an embodiment of the present disclosure.
Figure 5B:
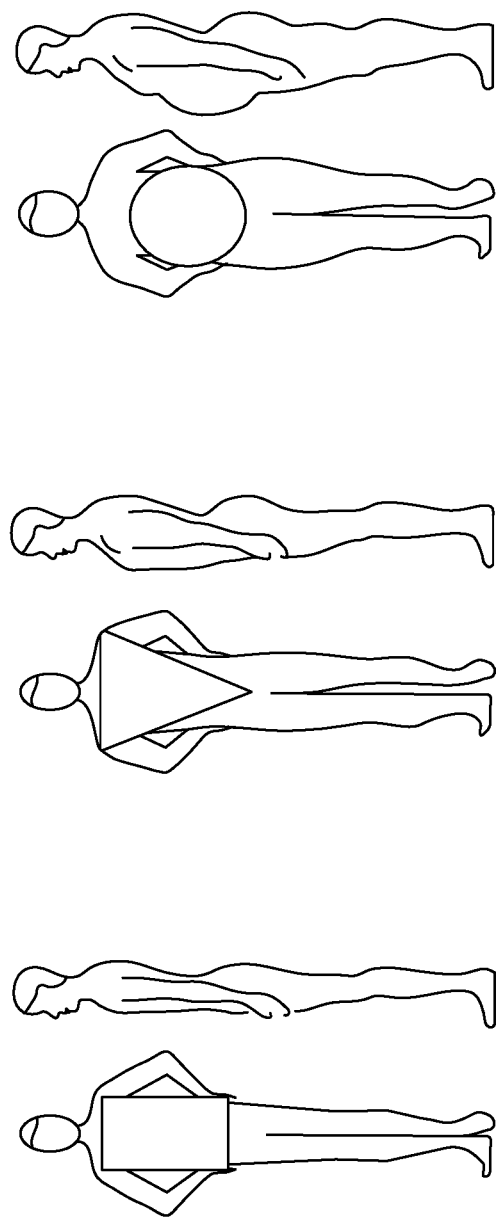

With reference to FIGS. 5A and 5B, a morphotype of the patient (e.g., ectomorph, mesomorph, or endomorph may be generated by the application 116 based on the clinical profile of the patient or indicated and/or confirmed by the clinician through the user interface 118. Depending on the gender of the patient, morphotype may be depicted using female patient illustrations (FIG. 5A) or male patient illustrations (FIG. 5B).

Figure 6B:
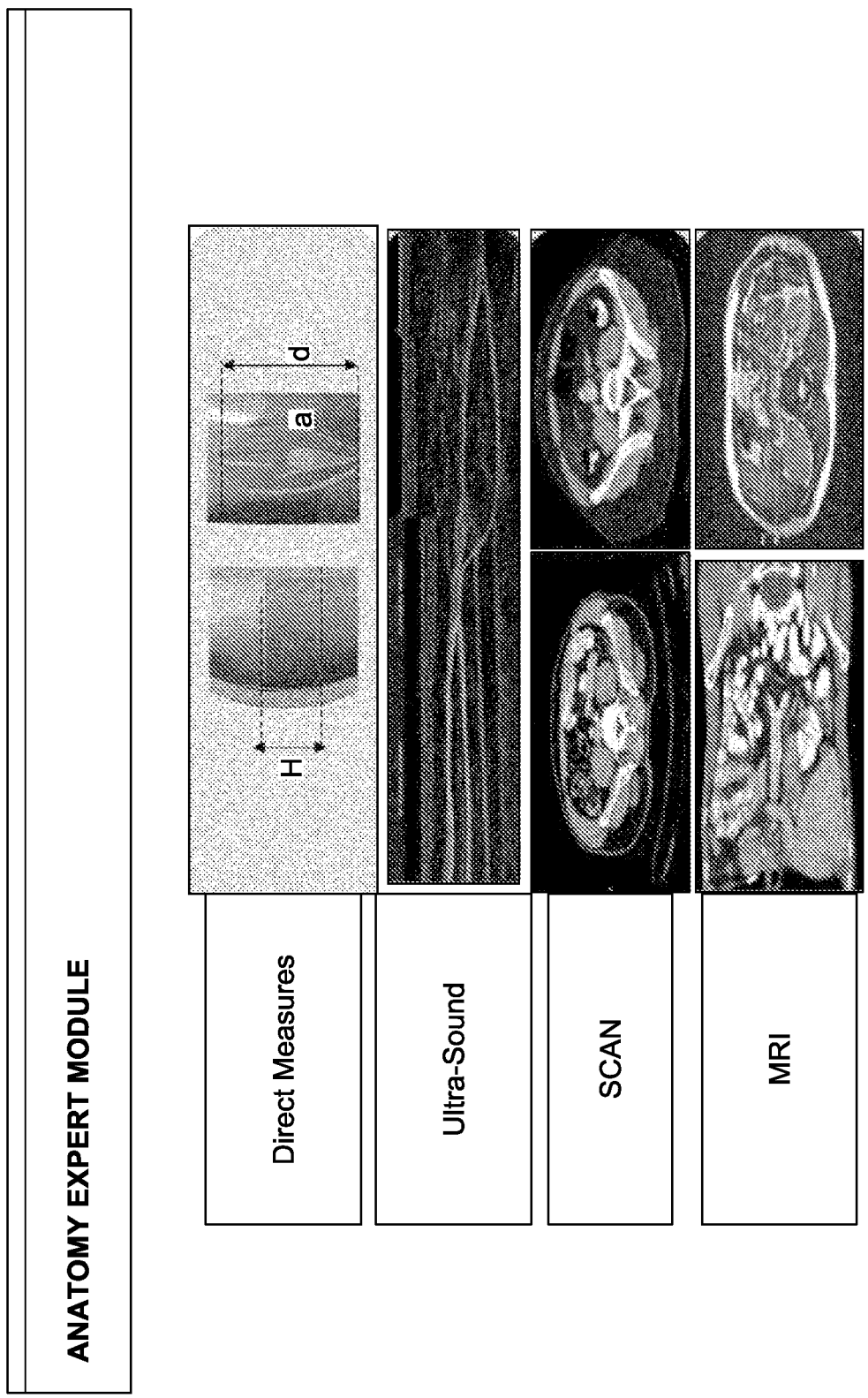
FIG. 6B is an illustration of a user interface showing supplemental sources of data that may be imported in connection with the anatomical profile of FIG. 6A.

With reference to FIG. 6A, an anatomical profile of the patient's particular anatomical structures may be generated by the application 116 based on the clinical profile of the patient and displayed to the clinician via the user interface 118. The anatomical profile may include editable values for length, width, angle, and thickness of anatomical structures (e.g., tissue, fat, and bone). In the illustrated example of FIG. 6A, anatomical structures included in the profile may include, but are not limited to, fat, linear alba, skin, pelvis, ribs, spine, rectus muscle, rectus sheath, external oblique, internal oblique, and transversus. As shown in FIG. 6A, selecting a particular anatomical structure on the interactive 3D model may generate a representation of a numerical value (shown in FIG. 6A as "146.") corresponding to a particular geometric characteristic (e.g., width) of the selected anatomical structure. A reliability level (e.g., low, medium, high) may be generated automatically by the application 116 or manually selected by the clinician to indicate a level of reliability in the anatomical profile. The reliability in the anatomical profile may correspond to the application's 116 use of the clinical profile of the patient in generating the anatomical profile. In some embodiments, the clinician may review, confirm, and/or edit the reliability level generated by the application 116 via the user interface 118. As shown in FIG. 6A, the clinician may also have an option to import additional data corresponding to the anatomical profile of a patient by selecting an "expert import" via the user interface 118. As shown in FIG. 6B, selecting "expert import" generates a menu (e.g., a pop up window) from which the clinician may select supplemental sources of data that provide data such as length, width, angle, and thickness of anatomical structures corresponding to the patient. For example, the clinician may import patient diagnostic results from various diagnostic modalities such as direct measurement, ultra-sound, CT scans, and MM. Data from supplemental sources of data may be provided to the computing device 100 substantially as described above with respect to importing a clinical profile of a patient in step 210. Importing additional data from supplemental sources may serve to increase the reliability level in the anatomical profile generated by the application 116.

Figure 7B:
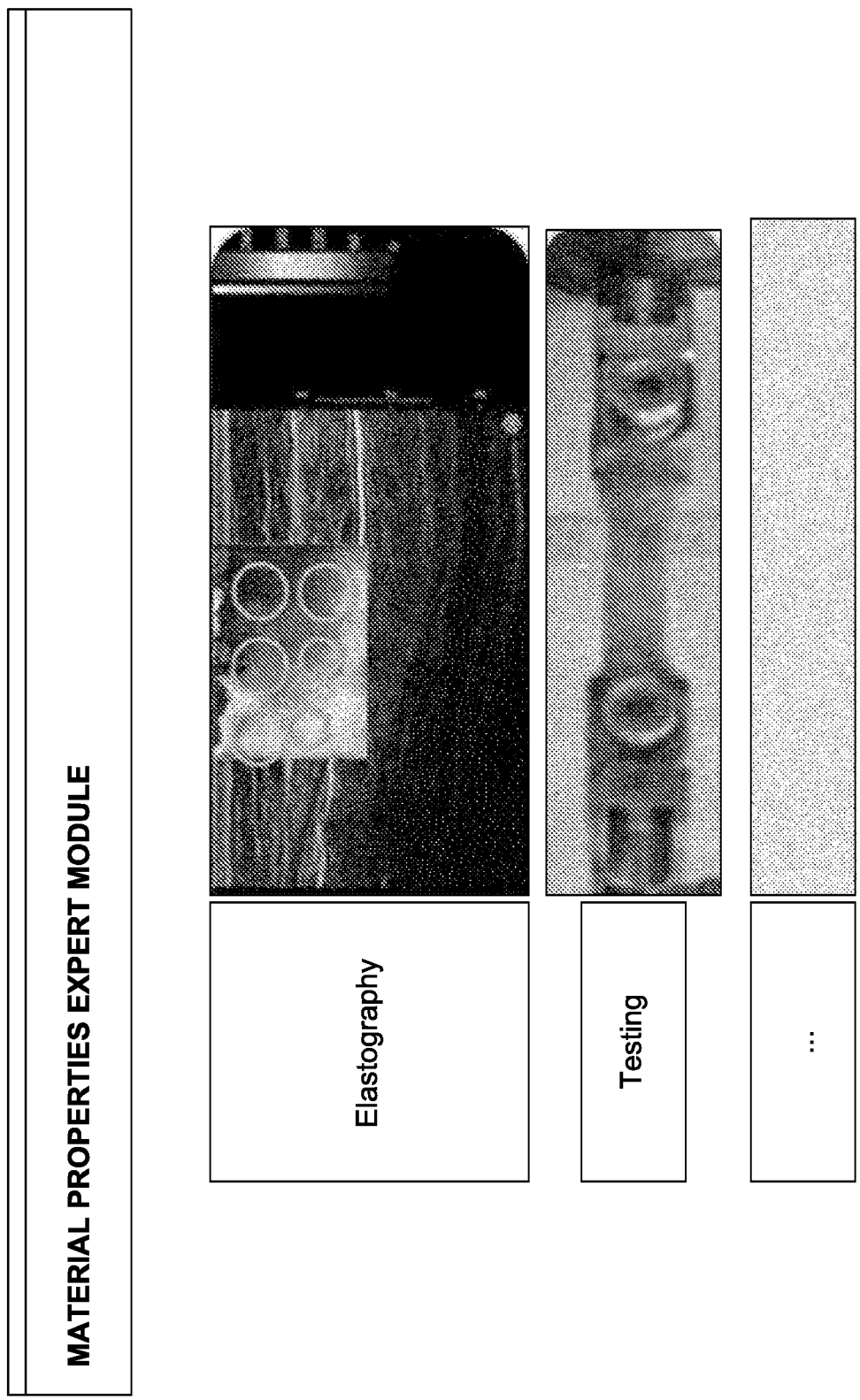
FIG. 7B is an illustration of a user interface showing supplemental sources of data that may be imported in connection with the tissue property profile of FIG. 7A.

With reference to FIG. 7A, the application 116 generates a tissue quality index of particular tissue properties (e.g., tissue elasticity) of the patient's particular anatomical structures and displays these tissue quality indexes to the clinician via the user interface 118 such that the clinician is provided with the opportunity to review, confirm, and/or edit the tissue quality indexes generated by the application 116. The clinician may also manually indicate a tissue quality index of particular tissue properties via the user interface 118. A reliability level (e.g., low, medium, high, etc.) may be generated automatically by the application 116 or manually selected by the clinician to indicate a level of reliability in the generated tissue quality indexes. The reliability in the tissue quality indexes may correspond to the application's 116 use of the clinical profile of the patient in generating the tissue quality indexes. In some embodiments, the clinician may also be provided with the opportunity to review, confirm, and/or edit the reliability level generated by the application 116 via the user interface 118. As described above with respect to FIGS. 6A and 6B, the clinician may also have an option to import additional data corresponding to tissue properties by selecting "expert import" via the user interface 118. As shown in FIG. 7B, selecting "expert import" in this instance generates a menu (e.g., a pop up window) from which the clinician may select supplemental sources of data that provide data related to tissue properties such as tissue elasticity. For example, the clinician may import patient diagnostic results from various diagnostic modalities such as elasticity testing, elastography, direct measurement, etc. Importing additional data from supplemental sources may serve to increase the reliability level in the tissue quality indexes generated by the application 116.

With reference to FIG. 8A, the application 116 generates a quality index corresponding to the muscular contractibility of the patient's particular anatomical structures and displays these quality indexes to the clinician via the user interface 118 such that the clinician is provided with the opportunity to review, confirm, and/or edit the quality indexes generated by the application 116. The clinician may also manually indicate a quality index corresponding to the muscular contractibility of particular tissue properties via the user interface 118. A reliability level (e.g., low, medium, high, etc.) may be indicated automatically by the application 116 or manually selected by the clinician to indicate a level of reliability in the generated muscular contractability quality indexes. The reliability in the muscular contractability quality indexes may correspond to the application's 116 use of the clinical profile of the patient in generating the muscular contractibility quality indexes. In some embodiments, the clinician may also be provided with the opportunity to review, confirm, and/or edit the reliability level generated by the application 116 via the user interface 118.

Figure 8B:
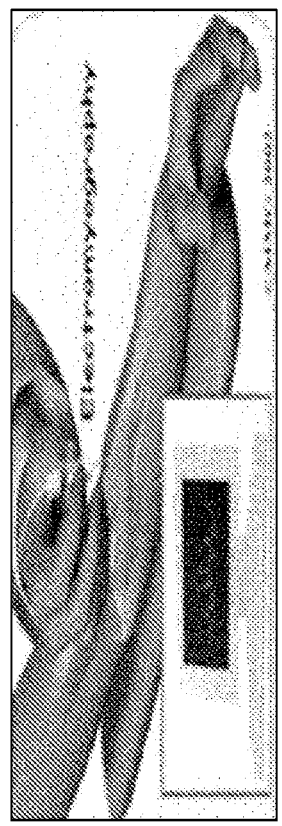
FIG. 8B is an illustration of a user interface showing supplemental sources of data that may be imported in connection with the muscular contractibility profile of FIG. 8A.
Figure 8B:
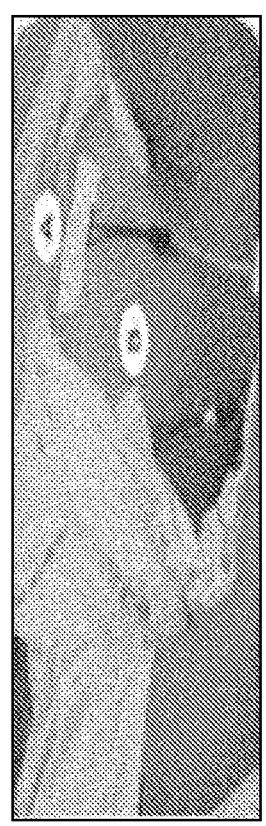
Figure 8B:
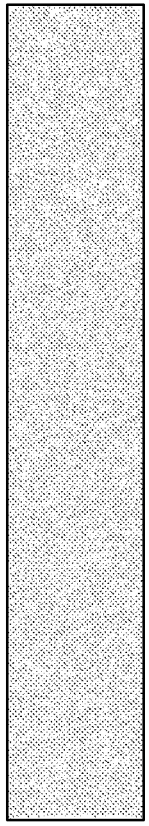

As described above with respect to FIGS. 6A-7B, the clinician may also have an option to import additional data corresponding to muscle contractibility by selecting "expert import" via the user interface 118. As shown in FIG. 8B, selecting "expert import" in this instance generates a menu (e.g., a pop up window) from which the clinician may select supplemental sources of data that provide data related to muscular contractibility. For example, the clinician may import patient diagnostic results from various diagnostic modalities such as deep electromyography and/or surface electromyography. Importing additional data from supplemental sources may serve to increase the reliability level in the muscular contractibility indexes generated by the application 116.

Referring now to FIGS. 6A, 7A, and 8A, the clinician may select and deselect particular anatomical structures to be visible or invisible on the interactive 3D model. For example, the clinician may mouse-click directly on the interactive 3D model to select or deselect a particular anatomical structure (e.g., tissue, fat, bone) to be visible or invisible or, for the same purpose, select or deselect a particular anatomical structure from a menu (e.g., pull down menu) listing the anatomical structures of the interactive 3D model. The above-described selection of anatomical structures may also be used to indicate a reliability index of particular anatomical structures and/or the muscular contractibility of particular anatomical structures to indicate the reliability and/or robustness of the data source used to provide parameters such as contractility, length, width, angle, and thickness for the selected anatomical structure.

Figure 9A:
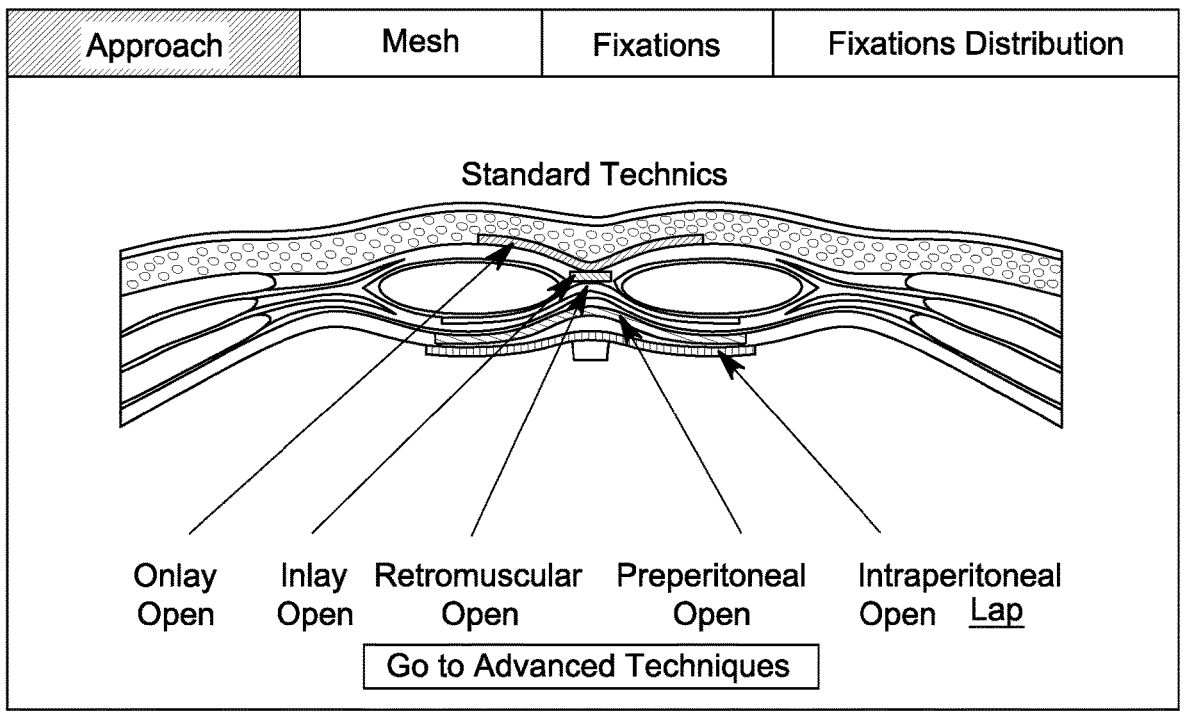
FIG. 9A is an illustration of a user interface presenting options for selecting a technique and options for selecting an open surgery plan or a laparoscopic surgery plan in connection with selecting an approach in accordance with an embodiment of the present disclosure.
Figure 9B:
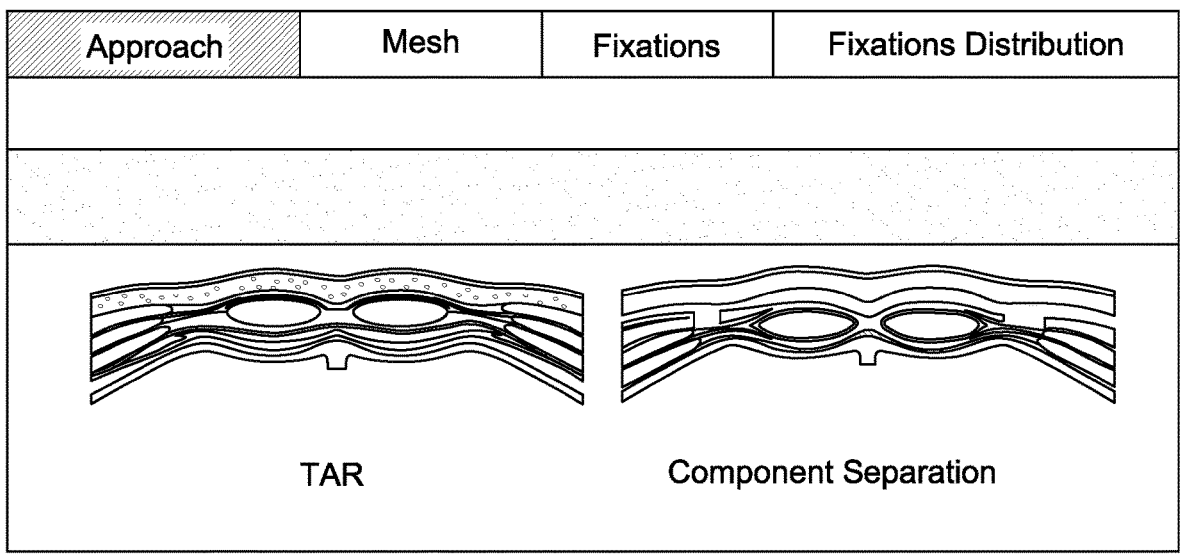
FIG. 9B is an illustration of a user interface presenting additional options for selecting a technique in connection with the technique options presented in FIG. 9A.
Figure 9C:
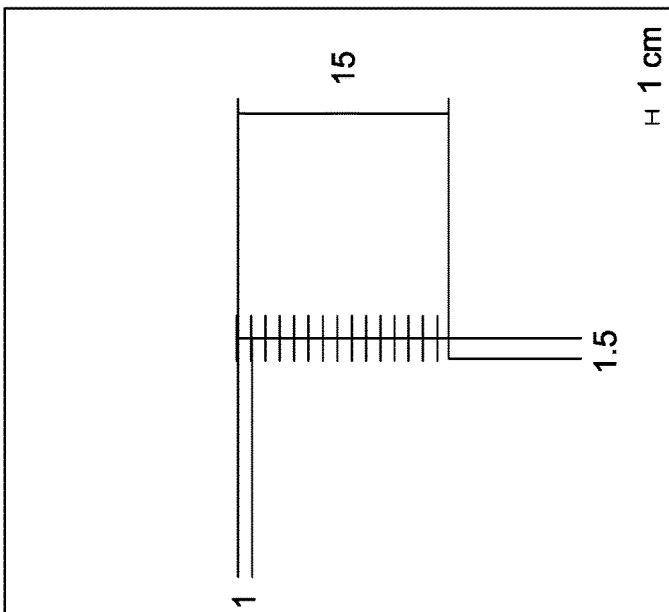
FIG. 9C is an illustration of a user interface presenting options for selecting details relating to a suture to be used in connection with the selected technique and selected surgery plan of FIG. 9A.
Figure 10A:
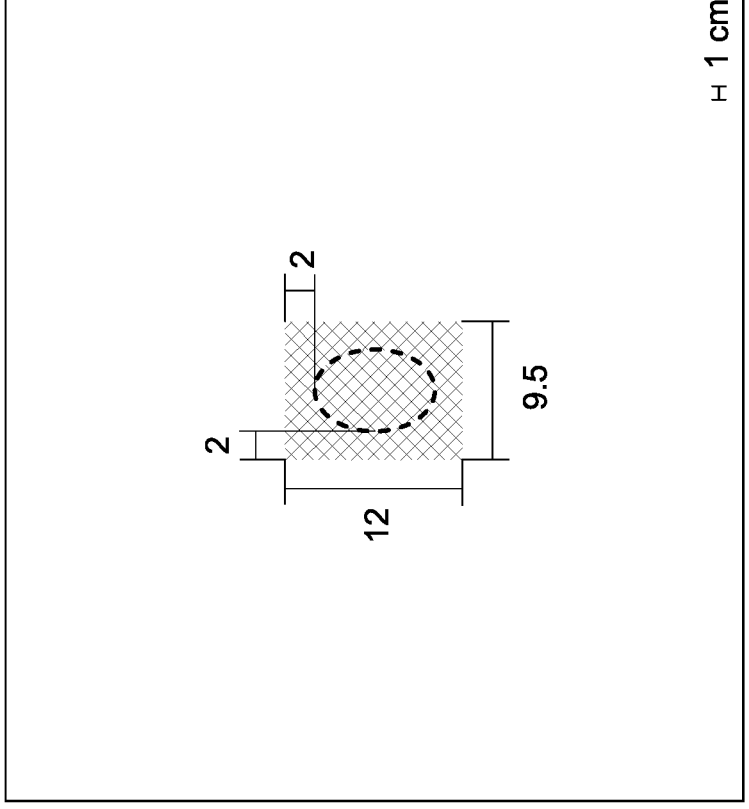
FIGS. 10A and 10B are illustrations of a user interface presenting a mesh selection process in connection with a step of selecting the open surgery plan option presented in FIG. 9A.
Figure 10B:
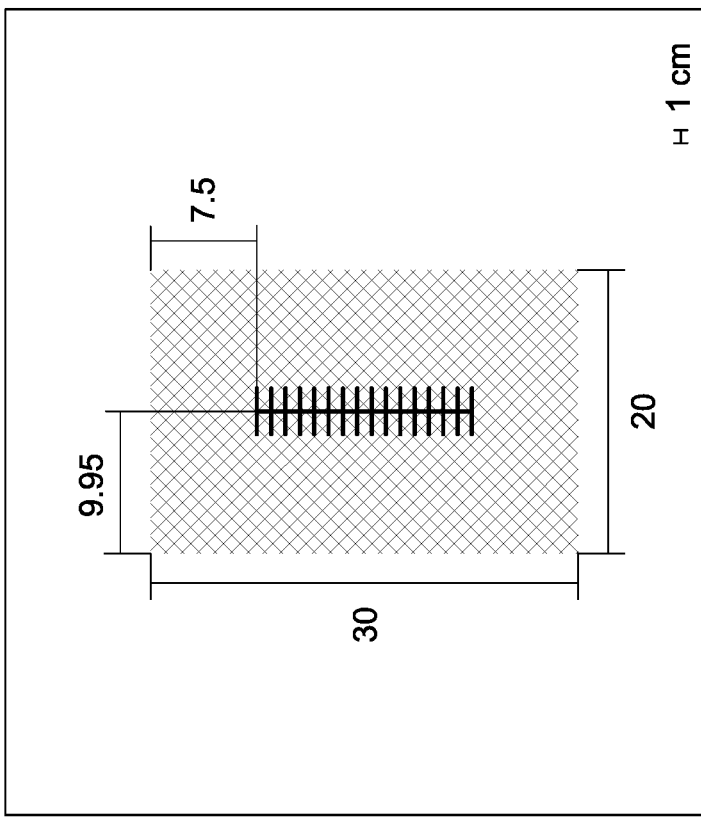

Step 230 includes generating a surgery plan for the patient. The surgery plan may be generated automatically by the application 116 and/or manually indicated by the clinician via the user interface 118. Generating a surgery plan for the patient may include, but is not limited to, indicating: (i) a technique for placement of a repair material (e.g., onlay, inlay, retromuscular, preperitoneal, intraperitoneal) as shown in FIG. 9A; (ii) a technique for tissue release (e.g., transversus abdominis muscle release (TAR) or component separation) as shown in FIG. 9B; and (iii) a type of defect repair (e.g., augmentation "defect closed" or bridging "defect non closed") to be used for repairing the tissue defect. In the case of an indication of an intraperitoneal approach, generating a surgery plan may also include indicating a surgical approach as either open or laparoscopic (shown in FIG. 9A). As detailed below, repair material specifications, fixations for securing the repair material to the surgical repair site, and a distribution of the fixations relative to the indicated repair material may be automatically generated by the application 116 and/or manually indicated by the clinician via the user interface 118. With reference to FIGS. 9A and 9B, the system may display a surgical repair site, illustrated in FIGS. 9A and 9B as an abdominal area, to provide the clinician with the capability to indicate an approach technique for placement of an implantable repair material such as a hernia mesh, a prophylactic mesh, or a suture. For example, in the instance of hernia repair, the clinician may specify the approach technique as onlay, inlay, retromuscular, preperitoneal, or intraperitoneal, as shown in FIG. 9A, or as TAR or component separation, as shown in FIG. 9B. Additionally, the clinician may be provided the capability to indicate a defect closure type in combination with the indication of placement of the implantable repair material. For example, the clinician may indicate the defect closure type as bridging (defect non closed as shown in FIG. 10A) or augmentation (defect closed as shown in FIG. 10B). In the instance of augmentation, for example, the approach technique indicated by the clinician may include indicating details about a suture to be used to perform the defect closure as well as a distribution associated with placement of the suture, as shown in FIG. 9C. For example, the clinician may indicate a brand, a model, a length, a material, and a resorption of the suture to be used in the bridging technique. Additionally, the clinician may indicate suture dimensions, filament (e.g., mono-filament, multi-filament), ratio, technique (e.g., running, interrupted), and closure (e.g., mass, layered). As shown in FIG. 9C, each indicated detail about the suture and/or defect closure may be illustrated on the display to help the clinician visualize the suture in actual size in relation to the defect and to assess the distribution of the suture to ensure adequate coverage to reduce the risk of recurrence.

Figure 10D:
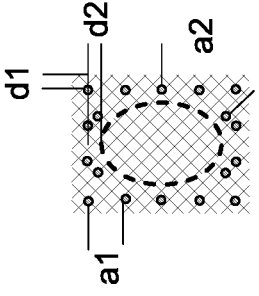
FIG. 10D is an illustration of a user interface presenting a fixation distribution process in connection with a step of selecting the open surgery plan option presented in FIG. 9A.

In the instance that an open bridging surgical approach is selected in step 230 (see FIG. 9A), FIGS. 10A, 10C, and 10D describe a process in connection with the selected open surgical approach of specifying details regarding the indicated implantable repair material, fixations used to secure the implantable repair material to patient tissue, and a distribution about the implantable repair material of the indicated fixation(s).

Referring specifically to FIG. 10A, the clinician may specify details about the indicated implantable repair material. For example, in the instance of a hernia mesh, the clinician may indicate a brand, a model, a size, a material resorption rate, a surfacic density, a transversal overlap, and a longitudinal overlap of the hernia mesh. As shown in FIG. 10A, each indicated detail about the hernia mesh may be illustrated on the display to help the clinician visualize the hernia mesh in actual size in relation to the defect and to assess the transversal and longitudinal overlap to ensure adequate coverage to reduce the risk of recurrence. Additionally, as shown in FIG. 10A, the clinician may adjust values corresponding to the placement of the mesh along the x-axis and y-axis, thus, providing the clinician the capability of centering the hernia mesh about the tissue defect.

Referring now to FIG. 10B, in the instance of augmentation, the clinician may indicate a brand, a model, a size, a material resorption rate, a surfacic density, a transversal overlap, and a longitudinal overlap of the mesh. As shown in FIG. 10B, each indicated detail about the mesh may be illustrated on the display to help the clinician visualize the mesh in actual size in relation to the suture and to the defect and to assess the transversal and longitudinal overlap to ensure adequate coverage to reduce the risk of recurrence. Additionally, as shown in FIG. 10B, the clinician may adjust values corresponding to the placement of the mesh along the x-axis and y-axis, thus, providing the clinician the capability of adjust the position of the mesh relative to the suture and/or the defect.

With reference to FIG. 10C, the clinician may specify details about fixations used to secure the implantable repair material to patient tissue. For example, the clinician may indicate the use of tacks, sutures, glue, straps, and/or staples to secure a hernia mesh to tissue for hernia repair. For each indicated fixation, the clinician may indicate specifics such as brand, model, material (e.g., titanium tacks), type (e.g., cyanoacrylate glue), and/or a resorption rate.

With reference to FIG. 10D, the clinician may specify a distribution about the implantable repair material of the indicated fixation(s) described above with respect to FIG. 10C. Specifically, the clinician may specify a fixation distribution to be used, such as single crown, double crown, or a combination, mix, or hybrid of single crown and double crown. The clinician may also indicate the type of fixation to use at particular points about the implantable repair material such as the cardinal points and the corner points. The clinician may also be provided the capability to specify a distance between fixations (depicted as "a1" in FIG. 10D) and a distance between fixations and an edge of the implantable repair material (depicted as "d1" in FIG. 10D). Additionally or alternatively, the clinician may choose a free placement option to place fixations freely about the implantable repair material.

Laparoscopic Approach

In the instance that a laparoscopic surgical approach is selected in step 230 (see FIG. 9A), the clinician may be provided the opportunity to specify and account for conditions existing during implantation of the implantable repair material. Examples of such conditions include whether the patient's abdominal wall was inflated, whether the patient was laying down, whether the patient was sedated, etc. Since conditions during surgery are different than conditions post-surgery, this may provide for a more accurate simulation. In the instance of hernia repair, for example, the abdominal wall may be insufflated during surgery resulting in conditions to exist during implantation of the hernia mesh such as shifting, tightening, and/or stretching of the tissue defect. Once surgery is complete and the abdominal wall is desufflated, tissue may return to a normal state due to removal of the above-described conditions. Since the hernia mesh was implanted while tissue may have been in an abnormal state, as described above, returning the tissue to a normal state may cause the implanted hernia mesh to lose contact with tissue, to fold, or to move as a result. It is contemplated by the present disclosure that the application 116 may generate an observable simulation, as described below with respect to step 250, that accounts for the above-described effects on the hernia mesh upon return of the tissue to a normal state. As used herein with respect to an abdominal wall of a patient, the term "deflated" refers to the abdominal wall as either being in a natural, un-inflated state or returning from an inflated or insufflated state to a non-inflated or uninsufflated state. As used herein with respect to an abdominal wall of a patient, the term "inflated" refers to the abdominal wall as being insufflated.

In connection with the clinician selecting a laparoscopic surgical approach, FIGS. 11-28B illustrate a process that provides the clinician an opportunity to account for implantation conditions such as, for example, insufflation during laparoscopic surgery, so that shifting of the repair material upon desufflation of the abdominal wall is minimized. More specifically, the application 116 provides various optimized approaches for the clinician to choose from so that the clinician may specify the implantable repair material, the fixations used to secure the implantable repair material to patient tissue, and a distribution about the implantable repair material of the indicated fixation(s) under deflated abdominal wall conditions and inflated abdominal wall conditions at a particular laparoscopic intra-abdominal pressure ("Lap IAP"). While FIGS. 11-28B illustrate a process using a hernia mesh as the implantable repair material, other types of repair materials, such as sutures, are also contemplated.

Figure 11:
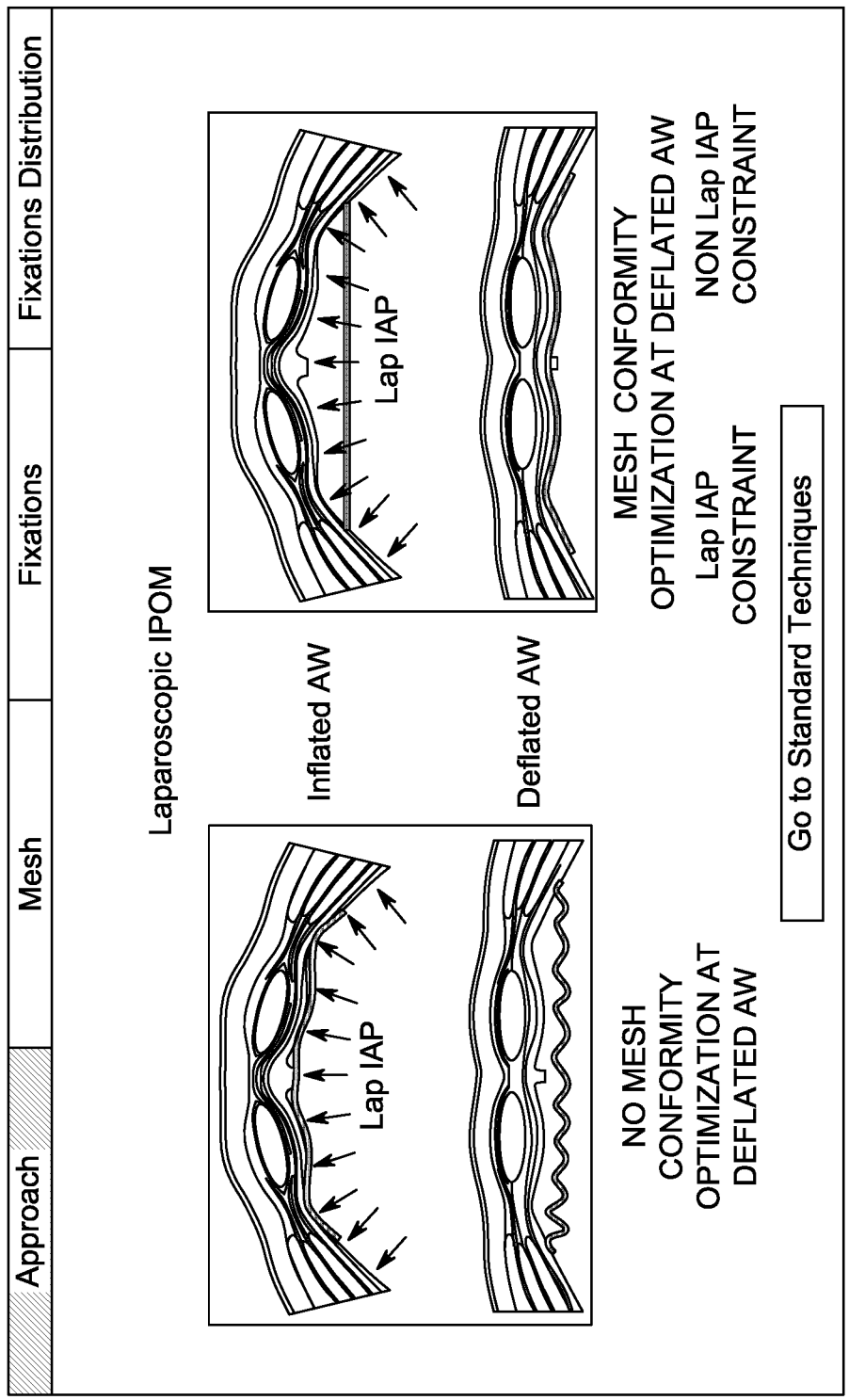
FIG. 11 is an illustration of a user interface presenting options for a mesh conformity optimization approach in connection with a step of selecting the laparoscopic surgery plan option presented in FIG. 9A.

With continued reference to step 230 (see FIG. 9A), upon selecting a laparoscopic surgery approach, the clinician may choose from a variety of implantation condition options (see FIG. 11) that account for implantation conditions such as, for example, insufflation during laparoscopic surgery, so that shifting of the hernia mesh upon desufflation of the abdominal wall is minimized. More specifically, and with reference to FIG. 11, options for utilizing a mesh conformity optimization algorithm allow the clinician to selectively utilize optimized fixation distribution parameters generated by the application 116 for use during laparoscopic hernia mesh implantation while the abdominal wall is inflated at a particular Lap IAP to produce a predictable resulting fixation distribution when the abdominal wall is returned to the deflated condition. The optimized fixation distribution while the abdominal wall is inflated and the resulting fixation distribution when the abdominal wall returns to a deflated condition may be presented to the clinician via the user interface 118 for review, confirmation, and/or editing, as described in more detail hereinbelow. As shown in FIG. 11, the mesh conformity optimization algorithm options include a "Non Lap IAP Constraint" mesh conformity optimization, a "Lap IAP Constraint" mesh conformity optimization, and "No" mesh conformity optimization. Each of these mesh conformity optimization algorithm options may be software programs integrated into the application 116 or separate stand-alone software programs.

Generally, the "Non Lap IAP Constraint" mesh conformity optimization (see FIGS. 14A-18B) accepts, as input from the clinician, target fixation distribution parameters corresponding to a deflated condition of the abdominal wall to achieve a target fixation distribution when the abdominal wall is returned to the deflated condition from an inflated condition. In response to this input from the clinician, the application 116 outputs optimized fixation distribution parameters to be applied to the hernia mesh when the abdominal wall is inflated at an optimized Lap IAP generated by the application 116 to achieve the target fixation distribution parameters specified by the clinician when the abdominal wall is returned to the deflated condition.

Generally, the "Lap IAP Constraint" mesh conformity optimization (see FIGS. 19A-23B) accepts, as input from the clinician, target fixation distribution parameters corresponding to a deflated condition of the abdominal wall and a Lap IAP at which the abdominal wall is to be inflated to achieve a target fixation distribution when the abdominal wall is returned to the deflated condition from an inflated condition. In response to this input from the clinician, the application 116 outputs optimized fixation distribution parameters to be applied to the hernia mesh when the abdominal wall is inflated at the Lap IAP specified by the clinician to achieve, or come close to achieving, the target fixation distribution parameters specified by the clinician when the abdominal wall is returned to the deflated condition. Since the "Lap IAP Constraint" mesh conformity optimization option allows the clinician to adjust the Lap IAP, stretching of the hernia mesh due to over-inflation of the abdominal wall may result. With this in mind, the clinician may be provided with a visualization of the hernia mesh before stretching and after stretching in conjunction with fixation distribution parameters so that the clinician can visualize the effects of inflating the abdominal wall to a particular Lap IAP. In some embodiments, the clinician may also be provided with this visualization upon selection of the "Lap IAP Constraint" and "No" mesh conformity optimization options.

Generally, the "No" mesh conformity optimization (see FIGS. 24A-28B) accepts, as input from the clinician, target fixation distribution parameters to be applied to the hernia mesh when the abdominal wall is inflated and a Lap IAP at which the abdominal wall is to be inflated to achieve a target fixation distribution when the abdominal wall is in the inflated condition. In response to this input from the clinician, the application 116 outputs fixation distribution parameters that will result from the abdominal wall being returned to the deflated condition. In contrast to the "Non Lap IAP Constraint" and "Lap IAP Constraint" mesh conformity optimization options, the "No" mesh conformity optimization option includes the user inputting target fixation distribution parameters to be applied to the hernia mesh when the abdominal wall is inflated (see FIG. 24B).

Figure 12:
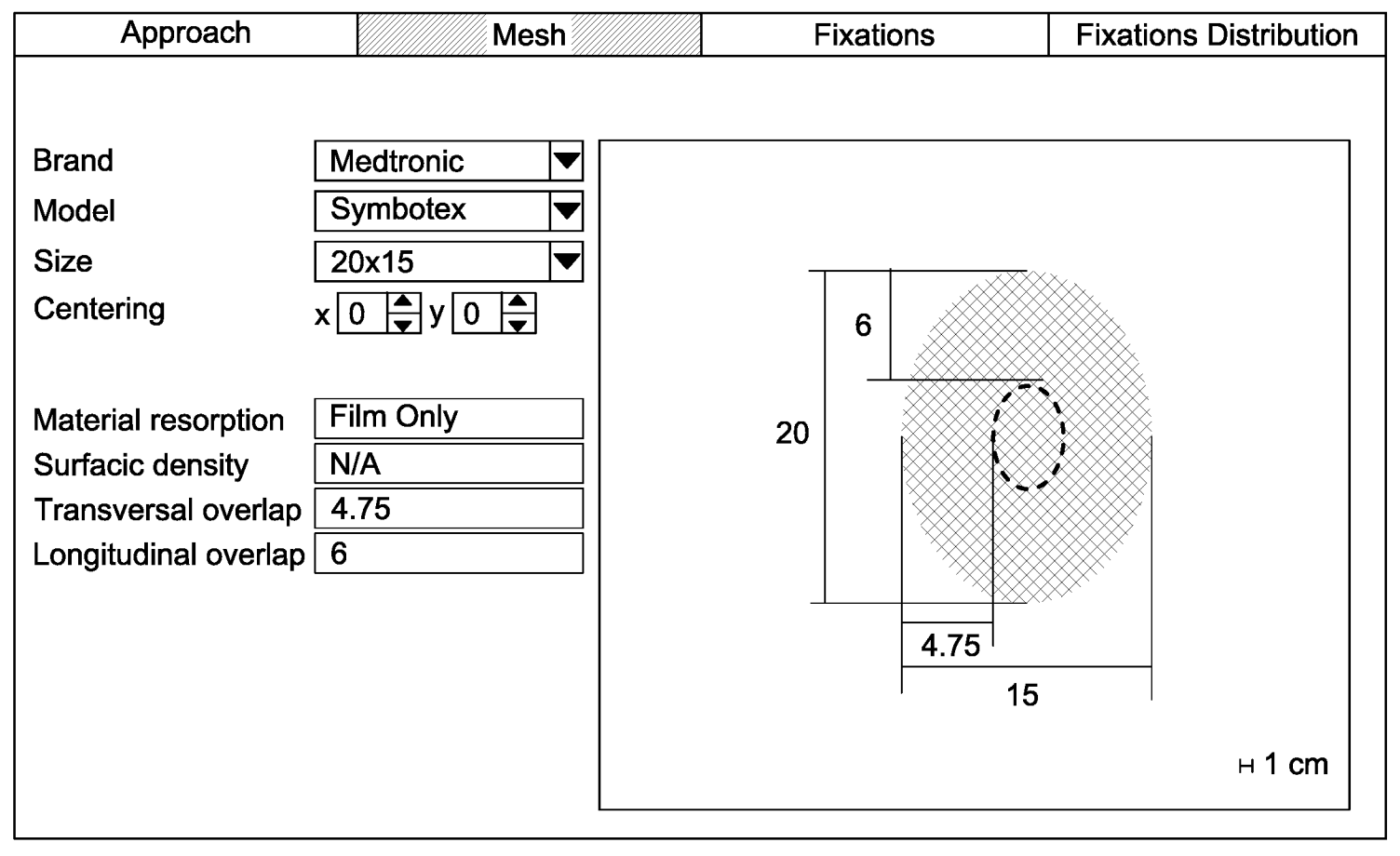

With reference to FIGS. 12 and 13, upon selection of a mesh conformity optimization option (see FIG. 11), the clinician may specify details about the hernia mesh (e.g., brand, model, size, material resorption rate, surface density, transversal overlap, and longitudinal overlap of the hernia mesh), as shown in FIG. 12, and details about fixations used to secure the hernia mesh to tissue (e.g., tacks, sutures, glue, straps, and/or staples), as shown in FIG. 13. As shown in FIG. 12, each indicated detail about the hernia mesh may be illustrated on the display to help the clinician visualize the hernia mesh in actual size in relation to the defect and to assess the transversal and longitudinal overlap to ensure adequate coverage to reduce the risk of recurrence. Additionally, as shown in FIG. 12, the clinician may adjust values corresponding to the placement of the mesh along the x-axis and y-axis, thus, providing the clinician the capability of centering the hernia mesh about the tissue defect. With reference to FIG. 13, for each indicated fixation, the clinician may indicate specifics such as brand, model, material (e.g., titanium tacks), type (e.g., cyanoacrylate glue), and/or a resorption rate.

"Non Lap IAP Constraint" Mesh Conformity Optimization Option

Figure 14A:
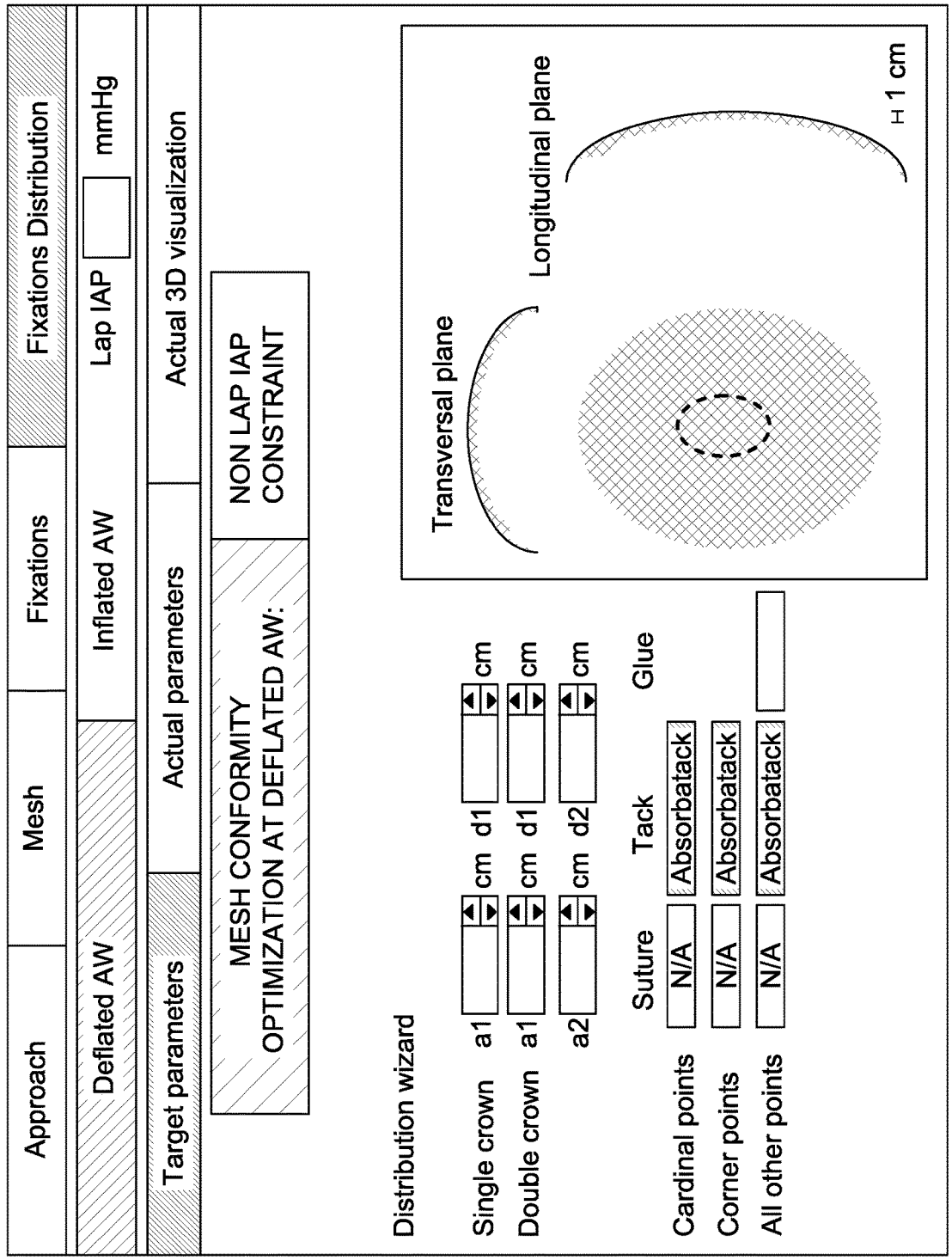
FIGS. 14A-18B are illustrations of a user interface presenting a fixation distribution process in connection with a step of selecting the "NON IAP CONSTRAINT" mesh conformity optimization option presented in FIG. 11 according to an embodiment of the present disclosure.
Figure 14B:
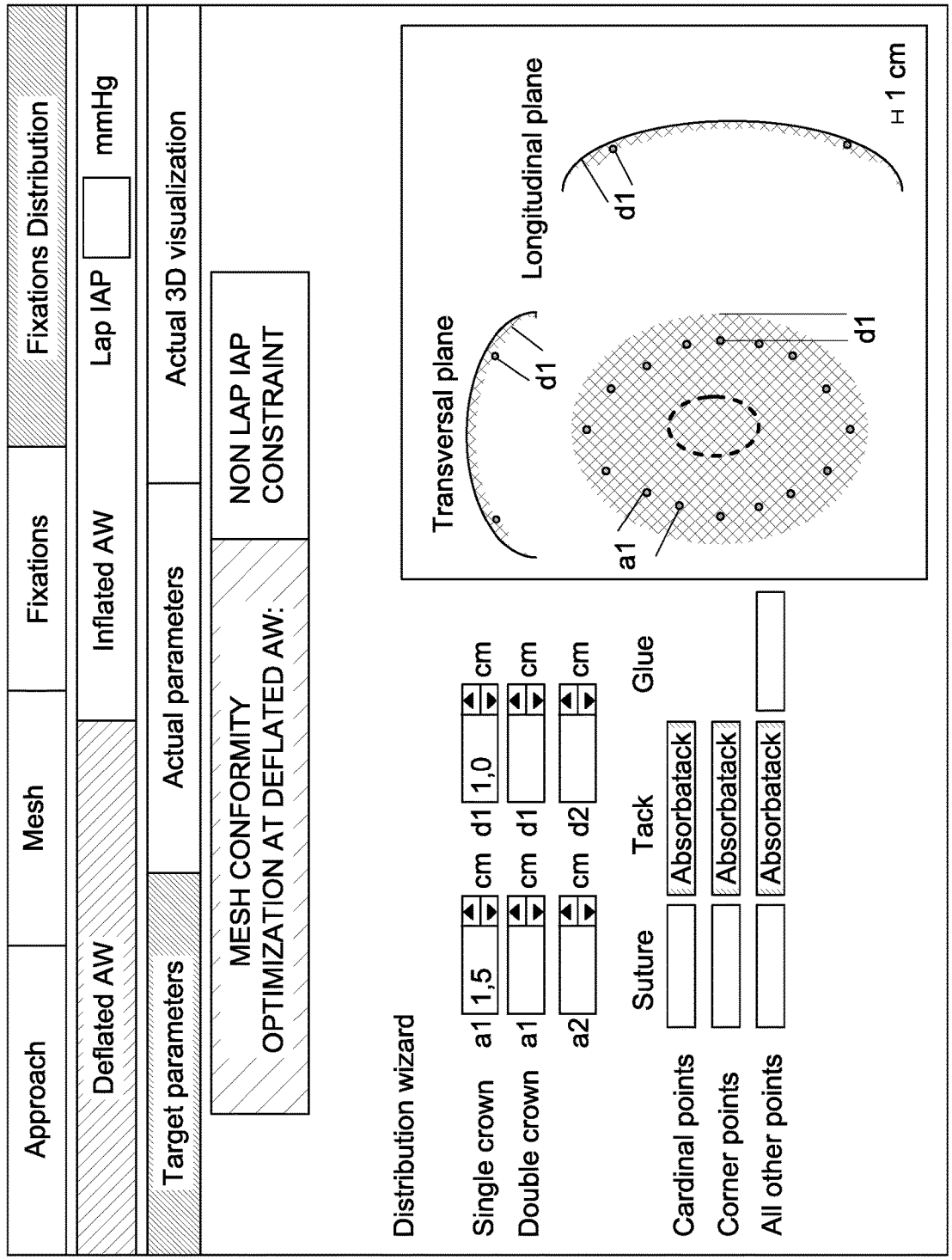
Figure 14C:
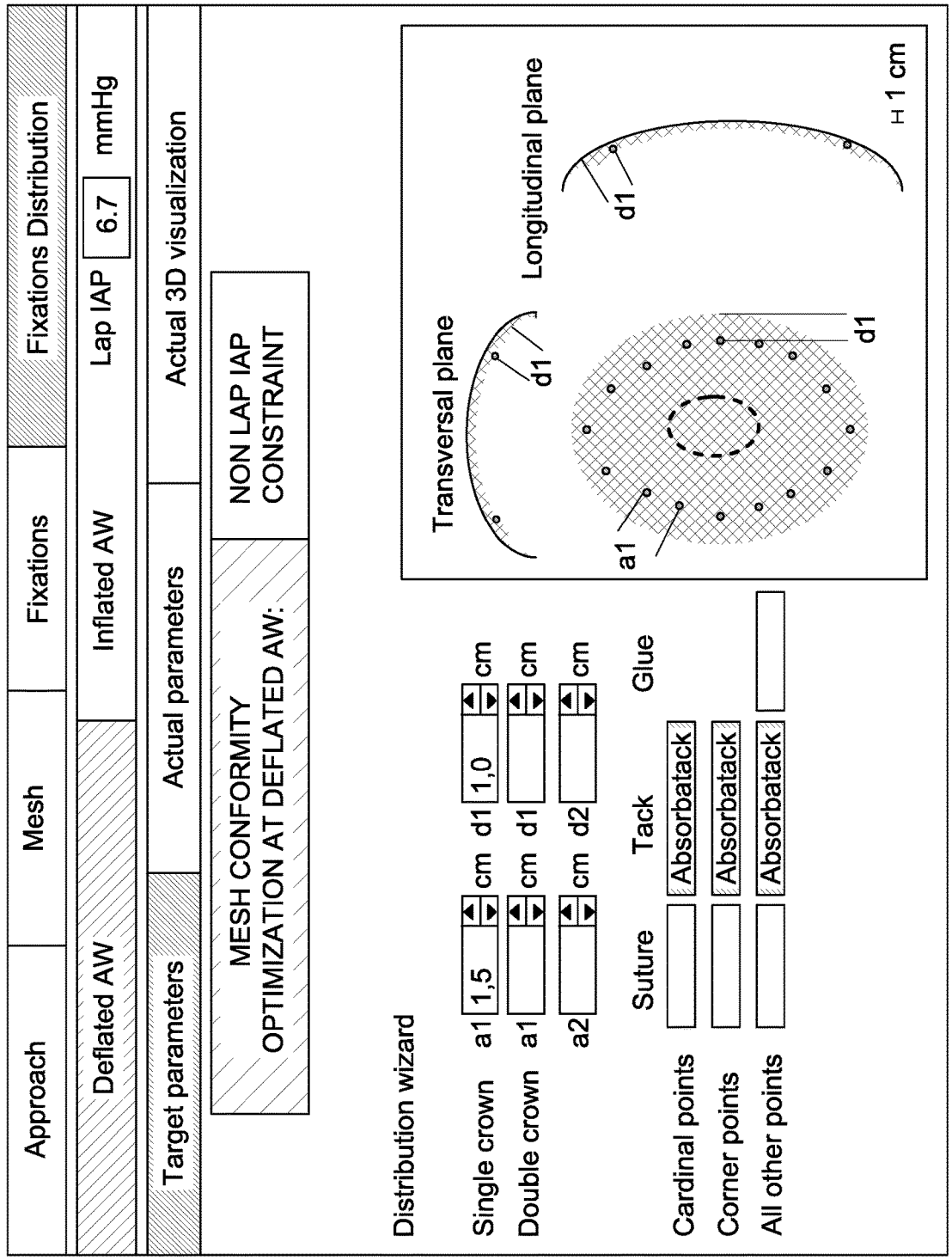

With reference to FIGS. 14A-14C, upon selection of the "Non Lap IAP Constraint" mesh conformity optimization option (see FIG. 11), the clinician may indicate target parameters for the distribution of fixations about the hernia mesh corresponding to a deflated condition of the abdominal wall. Specifically, the clinician may specify a fixation technique to be used, such as single crown, double crown, or a combination, mix, or hybrid of single crown and double crown. The clinician may also indicate the type of fixation to use at particular points about the hernia mesh such as the cardinal points and the corner points. The clinician may also be provided the capability to specify a distance between fixations (depicted in FIGS. 14A-14C as "a1") and a distance between fixations and an edge of the hernia mesh (depicted in FIGS. 14A-14C as "d1").

Figure 15A:
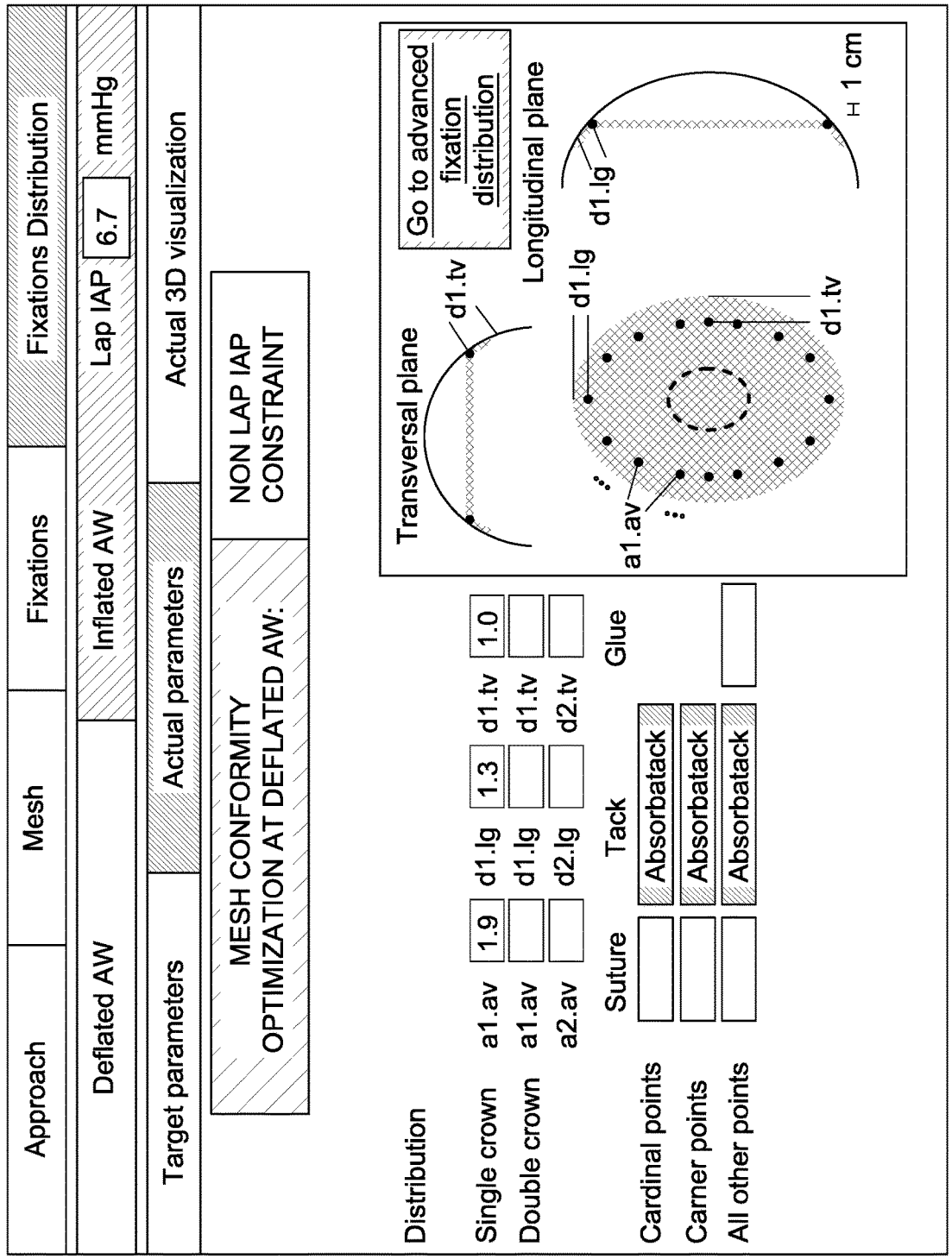
Figure 15B:
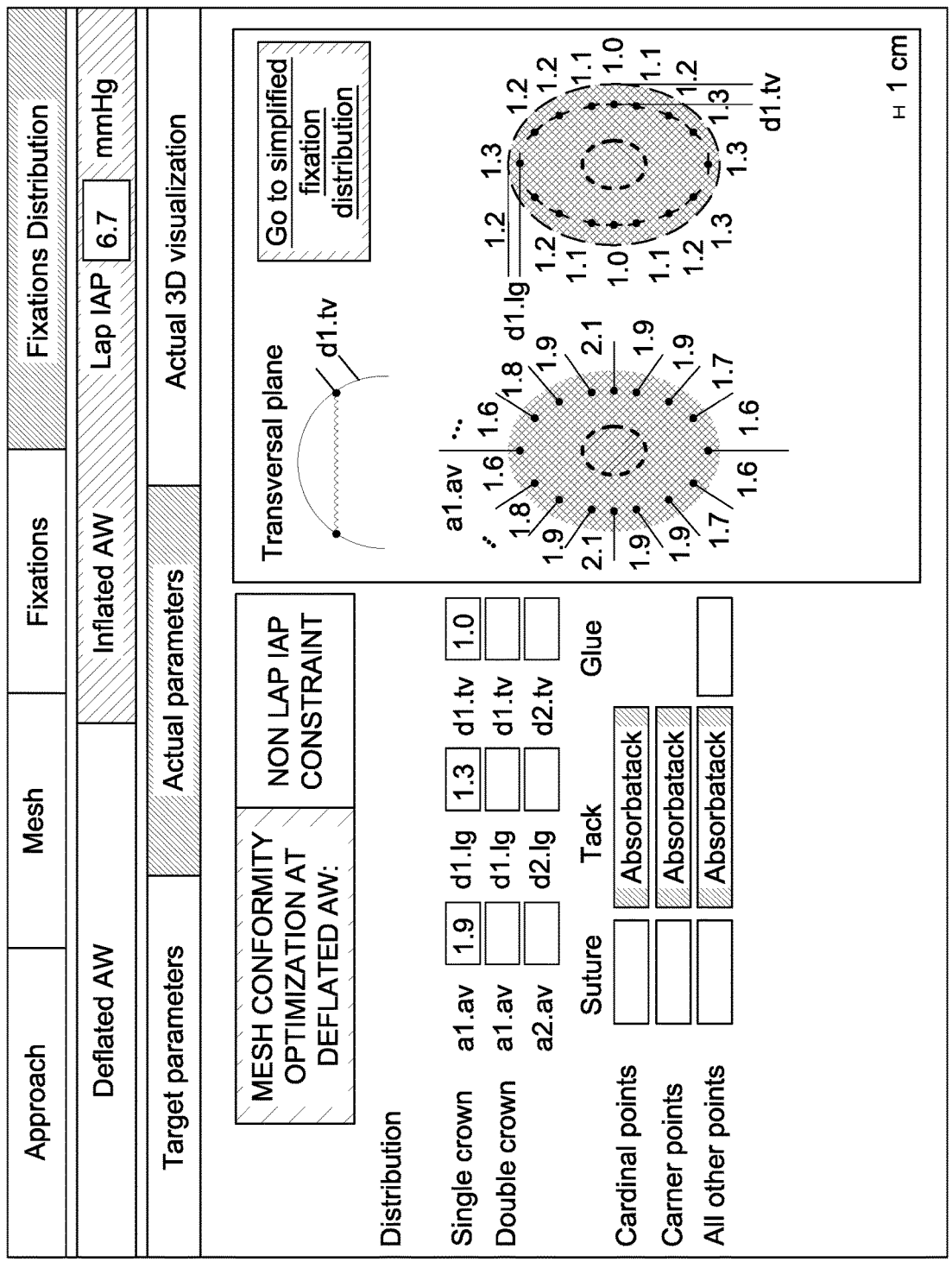

In response to the clinician specifying target values for "a1" and "d1", the application 116 generates an optimized Lap IAP in mmHg (depicted in FIG. 14C as 6.7 mmHg). The clinician may select "Actual parameters" (FIGS. 15A and 15B), in response to which the application 116 generates optimized fixation distribution parameters for the distribution of fixations about the hernia mesh while the abdominal wall is inflated. These optimized fixation distribution parameters (depicted in FIGS. 15A and 15B as a1.av, d1.1g, and d1.tv) indicate to the clinician that applying these optimized fixation distribution parameters to the hernia mesh while the abdominal wall is inflated at the optimized Lap IAP (e.g., 6.7 mmHg) will result in the target fixation distribution parameters previously indicated by the clinician (see FIG. 14B) upon return of the abdominal wall to the deflated condition. The clinician may choose to view the optimized fixation distribution under a "simplified fixation distribution" view as shown in FIG. 15A, which depicts the optimized fixation distribution applied to the hernia mesh about various planes (e.g., transversal plane, longitudinal plane, etc.) and includes references to a1.av, d1.1g, and d1.tv corresponding to particular fixation points on the hernia mesh. Additionally, the clinician may choose to view the optimized fixation distribution under an "advanced fixation distribution" view as shown in FIG. 15B, which depicts the optimized fixation distribution applied to the hernia mesh as in the "simplified fixation distribution" view, with the addition of an increased number of references to a1.av, d1.1g, and d1.tv corresponding to particular fixation points on the hernia mesh along with specific values for a1.av, d1.1g, and d1.tv.

Figure 16A:
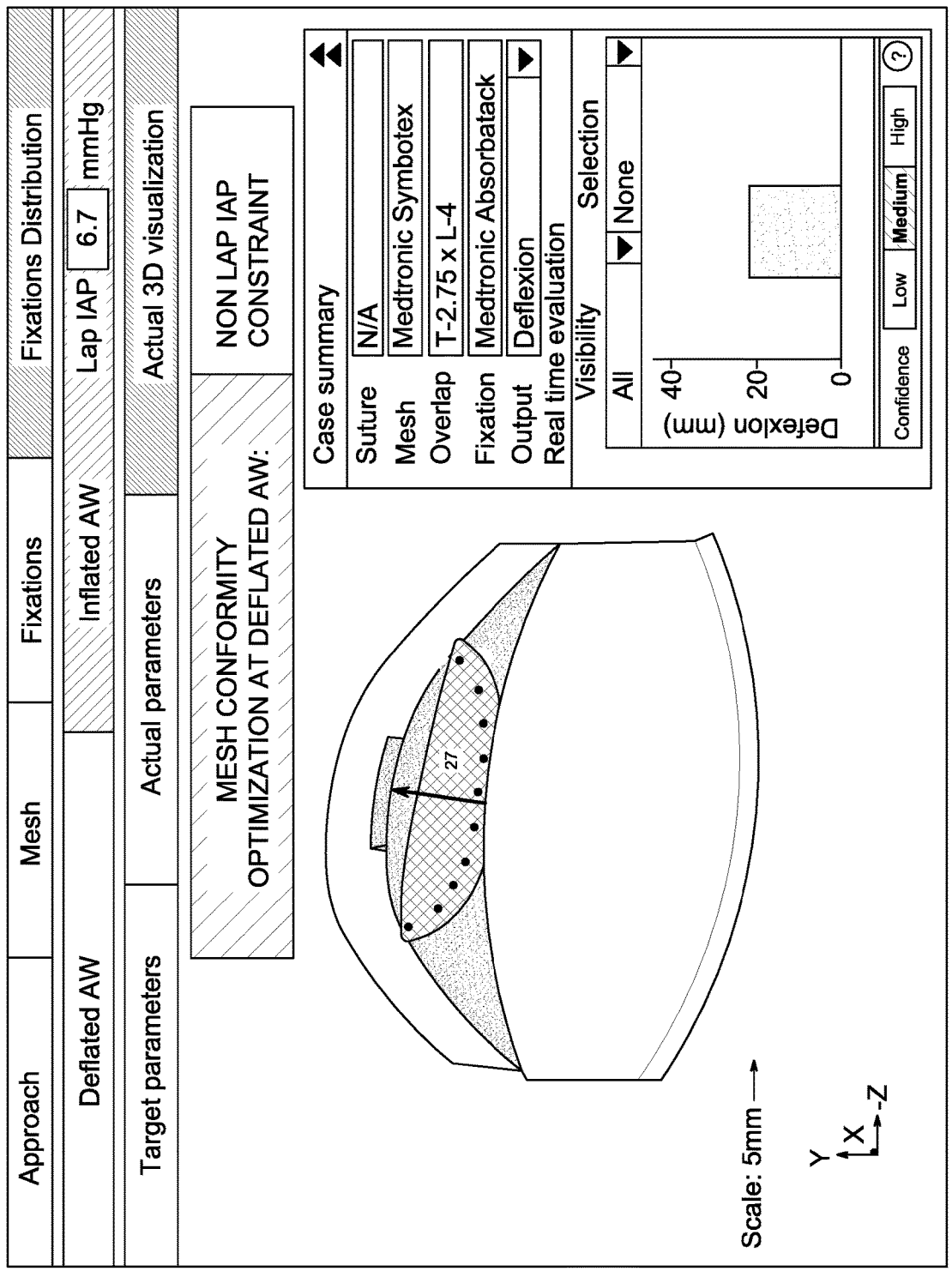
Figure 16B:
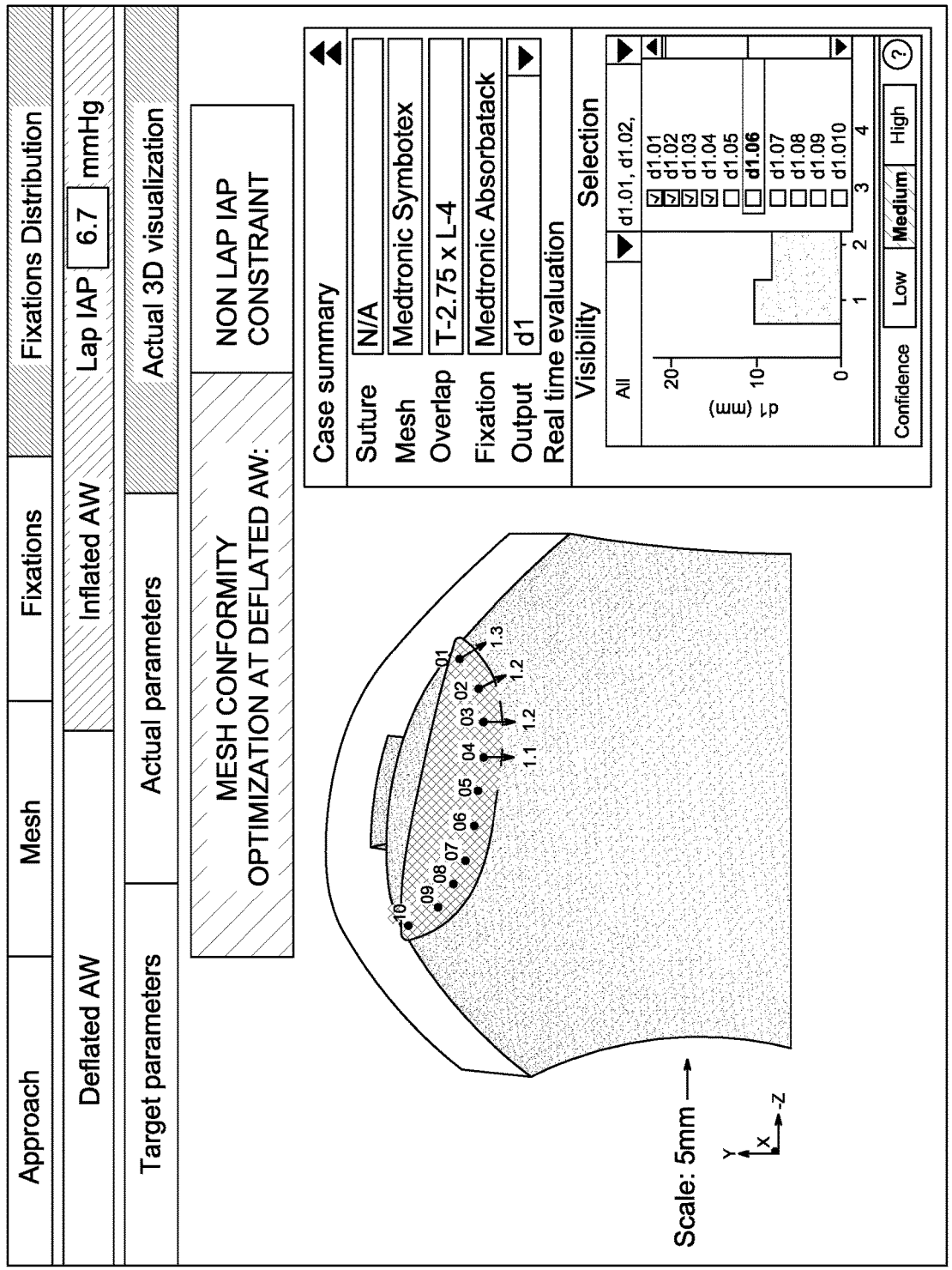
Figure 16C:
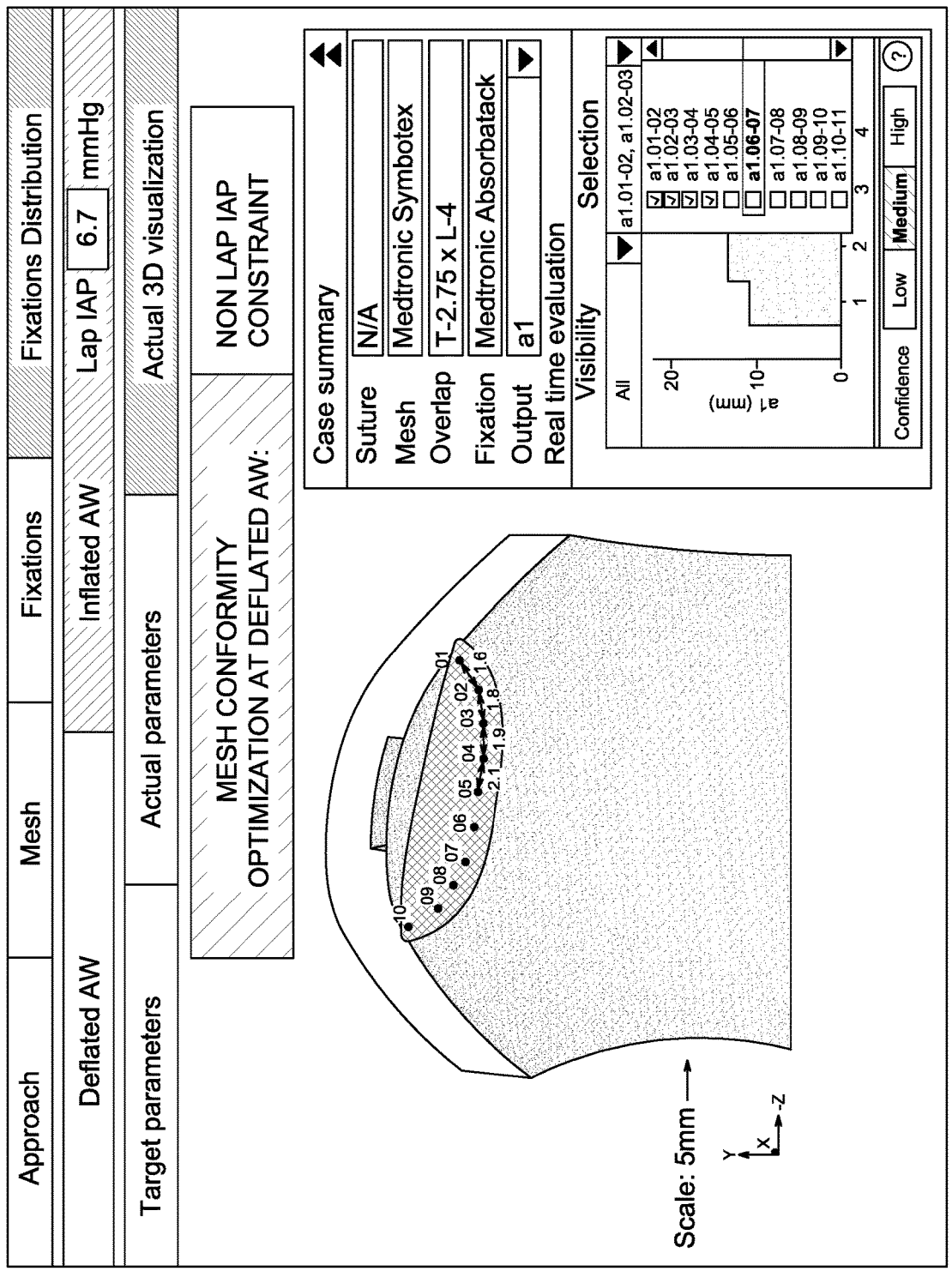

As shown in FIGS. 16A-16C, the clinician may choose to view an interactive 3D model of the hernia repair site when the abdominal wall is inflated at the optimized Lap IAP, e.g., by selecting "Actual 3D visualization." A "Case summary" of the interactive 3D model is displayed alongside the 3D model and includes a suture type, mesh type and size (or suture type and size), overlap measurements, and fixation type, all of which were previously indicated and/or confirmed by the clinician or otherwise based on a clinical profile provided to the computing device 100. Additionally, an output may be selected by the clinician (e.g., via a pull-down menu) to visualize outputs relating to the fixation distribution when the abdominal wall is in an inflated condition such as, but not limited to, deflexion (FIG. 16A), d1 (FIG. 16B), or a1 (FIG. 16C).

As shown in FIG. 16A, the clinician may choose "Deflexion" as the output to view the distance (e.g., shown in FIG. 16A as 27 mm) that the abdominal wall has expanded from a deflated condition to an inflated condition. Effectively, the "Deflexion" output serves to notify the clinician of how much working space has been created by insufflating the abdominal wall at the optimized Lap IAP. As shown in FIG. 16B, the clinician may choose "d1" as the output to view the distance (e.g., shown in FIG. 16B as 1.1 mm, 1.2 mm, and 1.3 mm) between selected fixations and an edge of the hernia mesh when the abdominal wall is inflated at the optimized Lap IAP. As shown in FIG. 16C, the clinician may choose "a1" as the output to view the distance between fixations when the abdominal wall is inflated at the optimized Lap IAP. For example, FIG. 16C shows a1 values between multiple pairs of fixations as 2.1 mm, 1.9 mm, 1.8 mm, and 1.6 mm. As detailed below, the clinician may use a "selection" menu (e.g., a pull-down menu) displayed alongside the 3D model, as shown in FIGS. 16A-16C, to select which fixation points or groups of fixation points for which to display corresponding d1 and a1 measurements.

Additionally, a "Real time evaluation" of the interactive 3D model is displayed alongside the 3D model, as shown in FIGS. 16A-16C. The "Real time evaluation" includes a "visibility" menu (e.g., a pull-down menu) through which the clinician may choose specific anatomical structures to be visible or invisible on the display of the 3D model. Anatomical structures may include, but are not limited to, fat, linear alba, skin, pelvis, ribs, spine, rectus muscle, rectus sheath, external oblique, internal oblique, and transversus. Additionally, the clinician may use a "selection" menu (e.g., a pull-down menu) to select or deselect specific fixation points or groups of fixation points superimposed on the 3D model to observe measurements (e.g., d1, a1) relating to those fixation points. Additionally, the interactive 3D model may be interacted with and manipulated by the clinician through the user interface 118. For example, the clinician may have the capability to zoom in and out on the 3D model, rotate the 3D model about an X-Y-Z axis, and move the 3D model within the display.

Figure 17A:
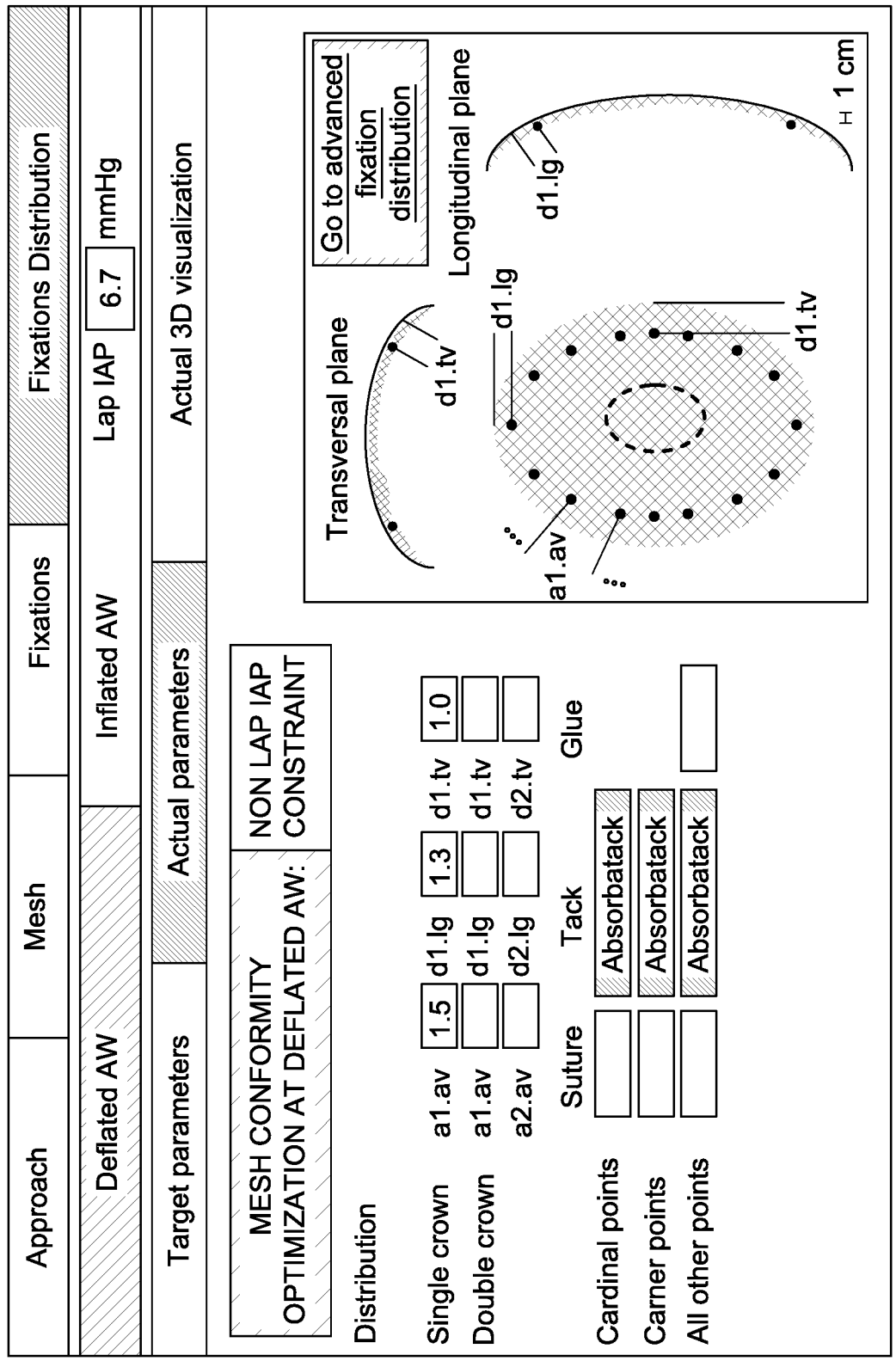
Figure 17B:
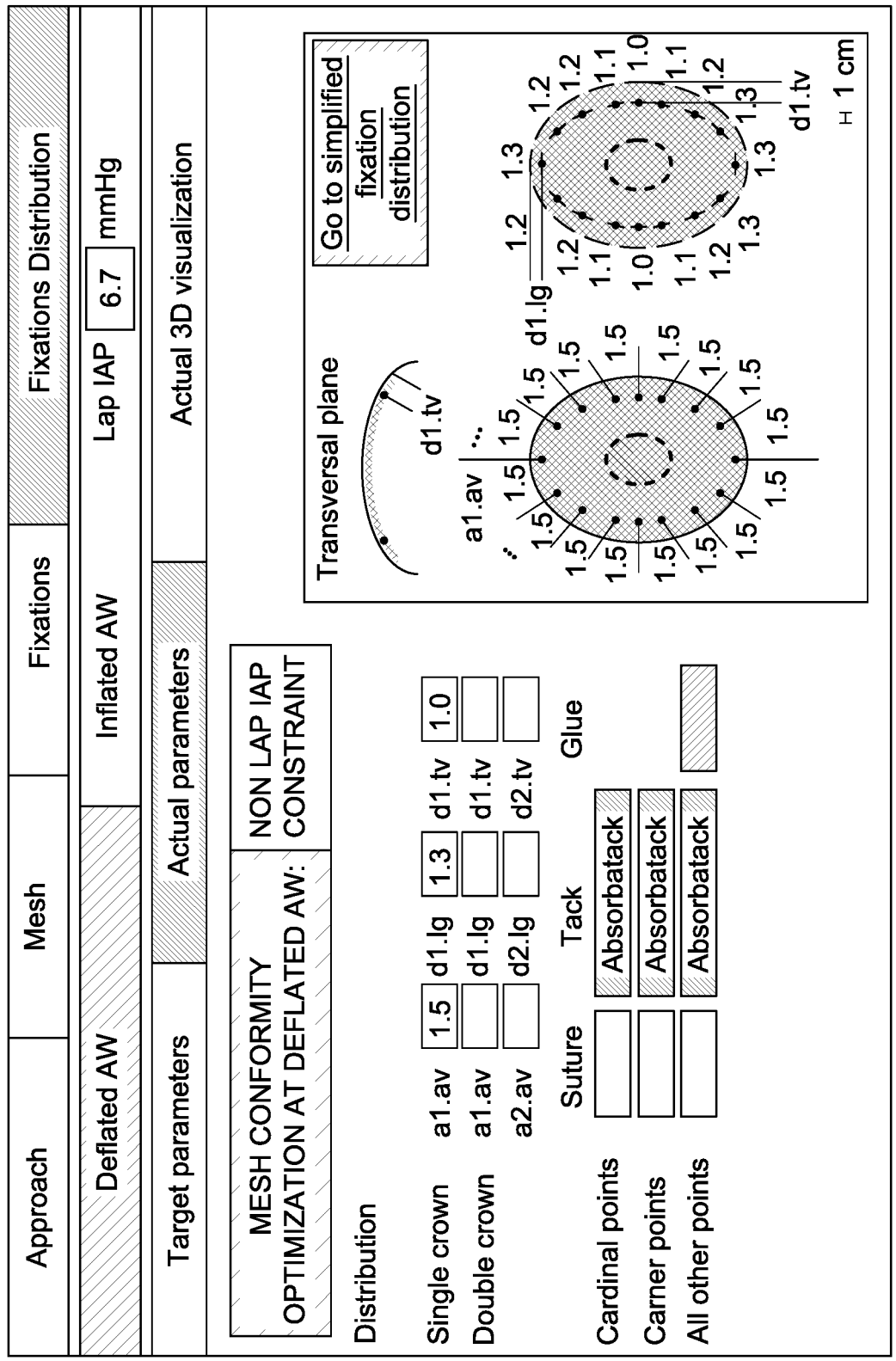

As shown in FIGS. 17A and 17B, the clinician may choose to view the "Actual parameters" relating to the fixation distribution upon return of the abdominal wall to the deflated condition resulting from the use of the optimized fixation distribution parameters generated by the application 116 while the abdominal wall was inflated (see FIGS. 15A and 15B). Substantially as described above with respect to FIGS. 15A and 15B, the clinician may choose to view a "simplified fixation distribution" while the abdominal wall is deflated as shown in FIG. 17A or an "advanced fixation distribution" as shown in FIG. 17B, which shows a more detailed view of the fixation distribution while the abdominal wall is deflated.

Figure 18A:
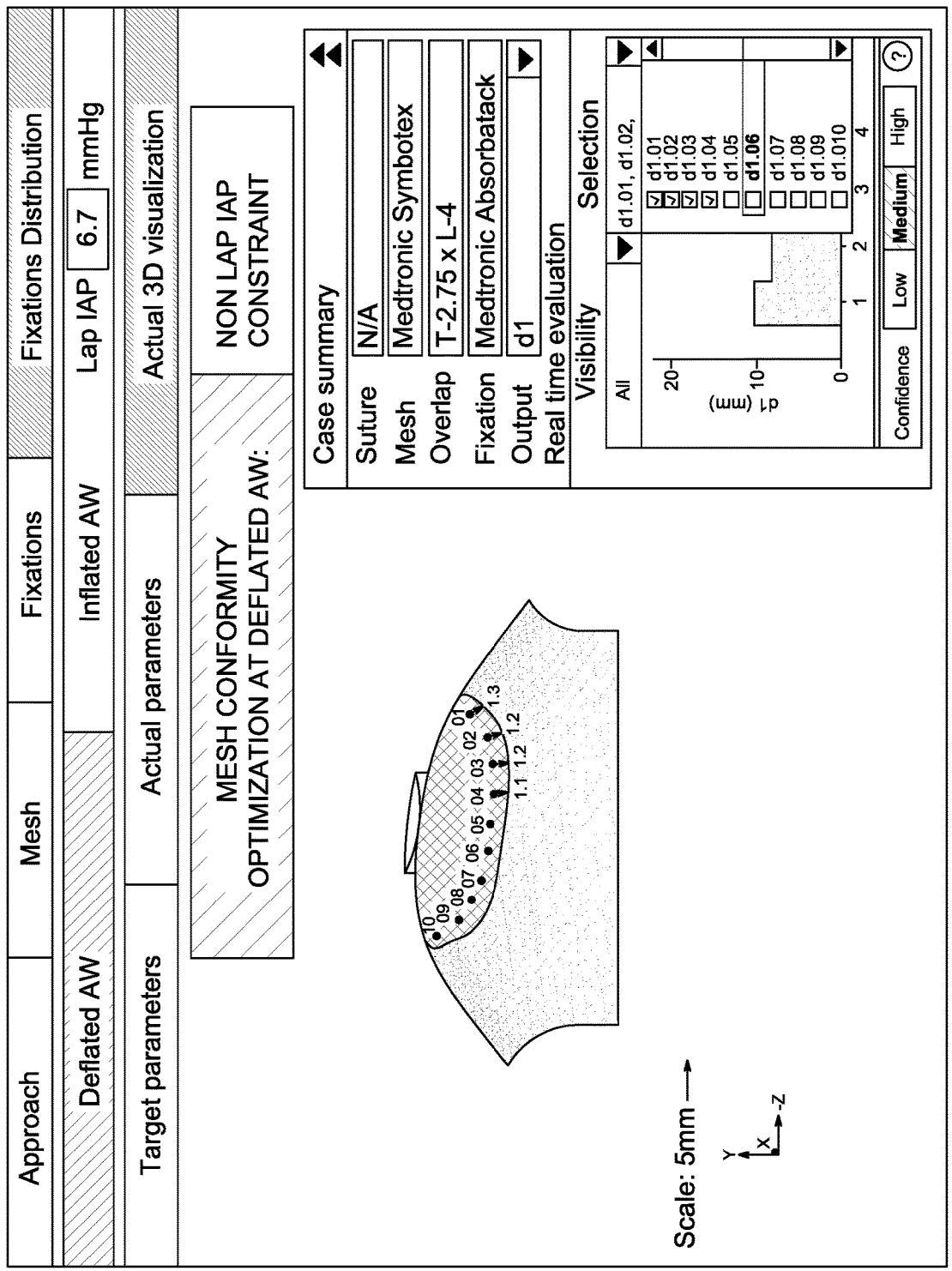
Figure 18B:
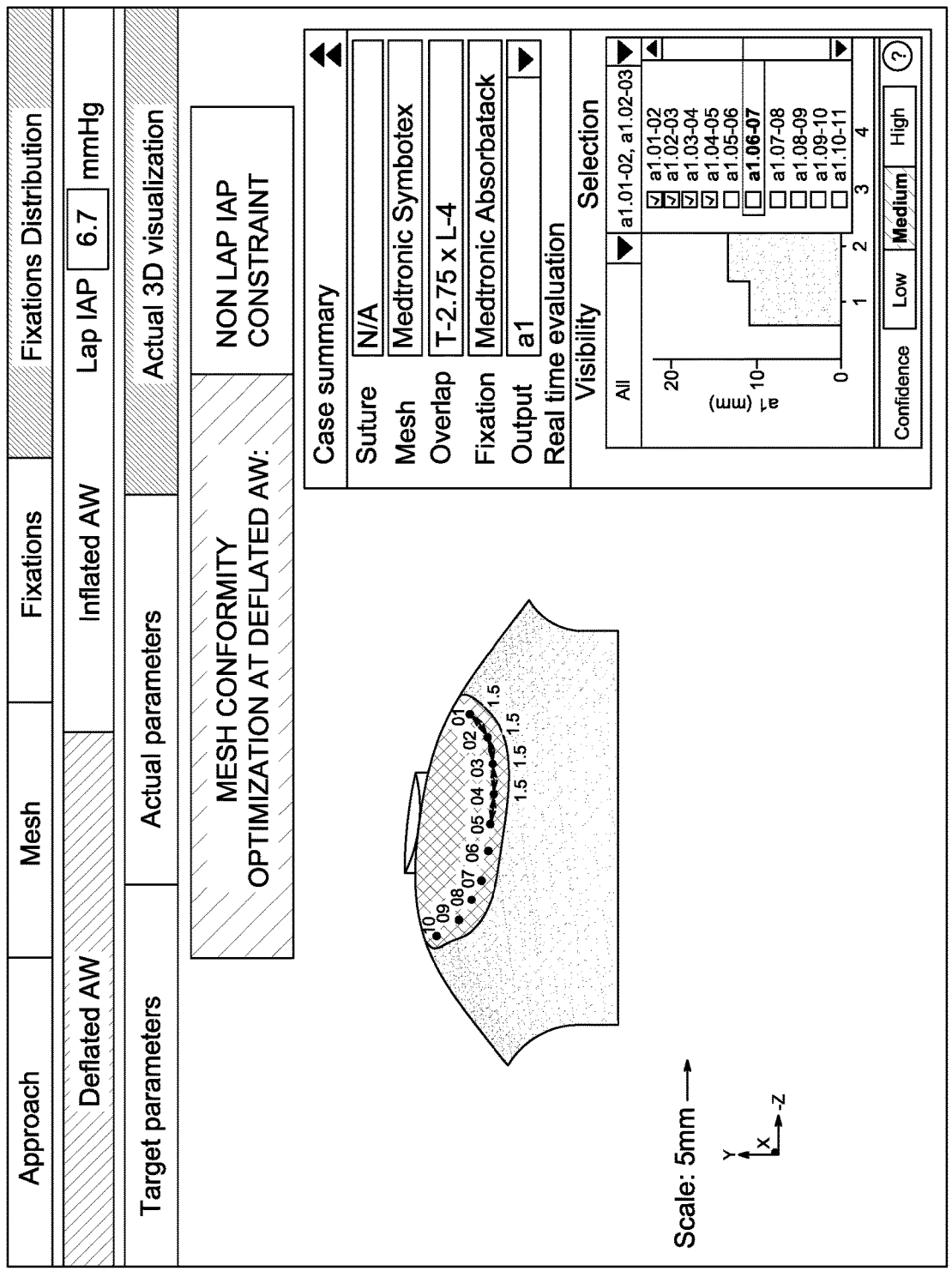

As shown in FIGS. 18A and 18B, the clinician may choose to view an interactive 3D model of the hernia repair site when the abdominal wall is returned to the deflated condition, e.g., by selecting "Actual 3D visualization." A "Case summary" of the interactive 3D model and a "Real time evaluation" is displayed alongside the 3D model substantially as described above with respect to FIGS. 16A-16C. Additionally, an output may be selected by the clinician (e.g., via a pull-down menu) to visualize outputs relating to the fixation distribution when the abdominal wall is in the deflated condition such as, but not limited to, d1 (FIG. 18A) and a1 (FIG. 18B).

As shown in FIG. 18A, the clinician may choose "d1" as the output to view the distance (e.g., shown in FIG. 18A as 1.1 mm, 1.2 mm, and 1.3 mm) between selected fixations and an edge of the hernia mesh when the abdominal wall is returned to the deflated condition from the inflated condition at the optimized Lap IAP. As shown in FIG. 18B, the clinician may choose "a1" as the output to view the distance (e.g., shown in FIG. 16C as 1.5 mm) between fixations when the abdominal wall is returned to the deflated condition from the inflated condition at the optimized Lap IAP.

"Lap IAP Constraint" Mesh Conformity Optimization Option

The "Lap IAP Constraint" mesh conformity optimization option (see FIG. 11) is substantially similar to the "Non Lap IAP Constraint" mesh conformity optimization option and is only described herein to the extent necessary to describe the differences in the process of the "Lap IAP Constraint" mesh conformity optimization option.

Figure 19A:
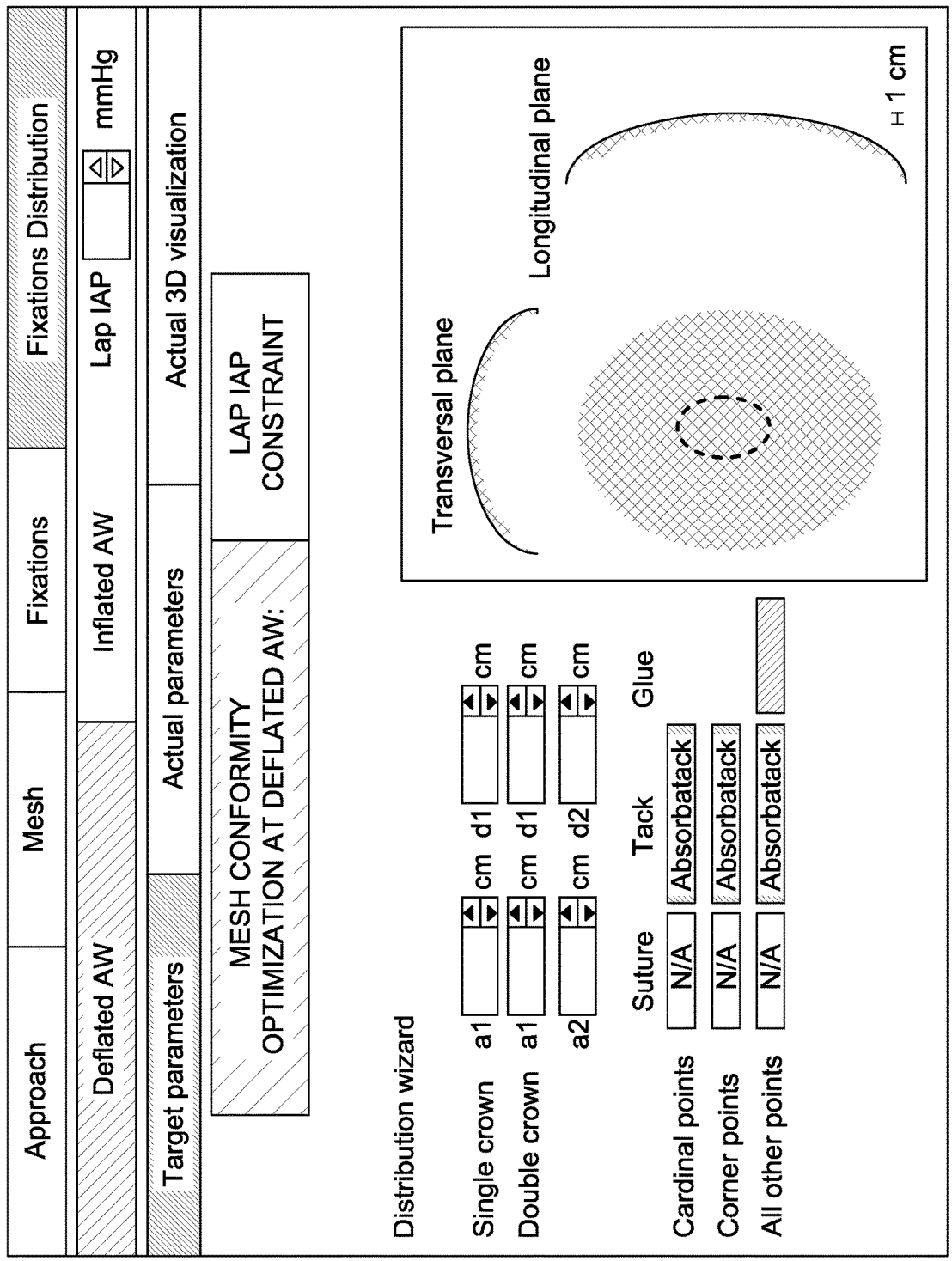
FIGS. 19A-23B are illustrations of a user interface presenting a fixation distribution process in connection with a step of selecting the "Lap IAP CONSTRAINT" mesh conformity optimization option presented in FIG. 11 according to an embodiment of the present disclosure.
Figure 19B:
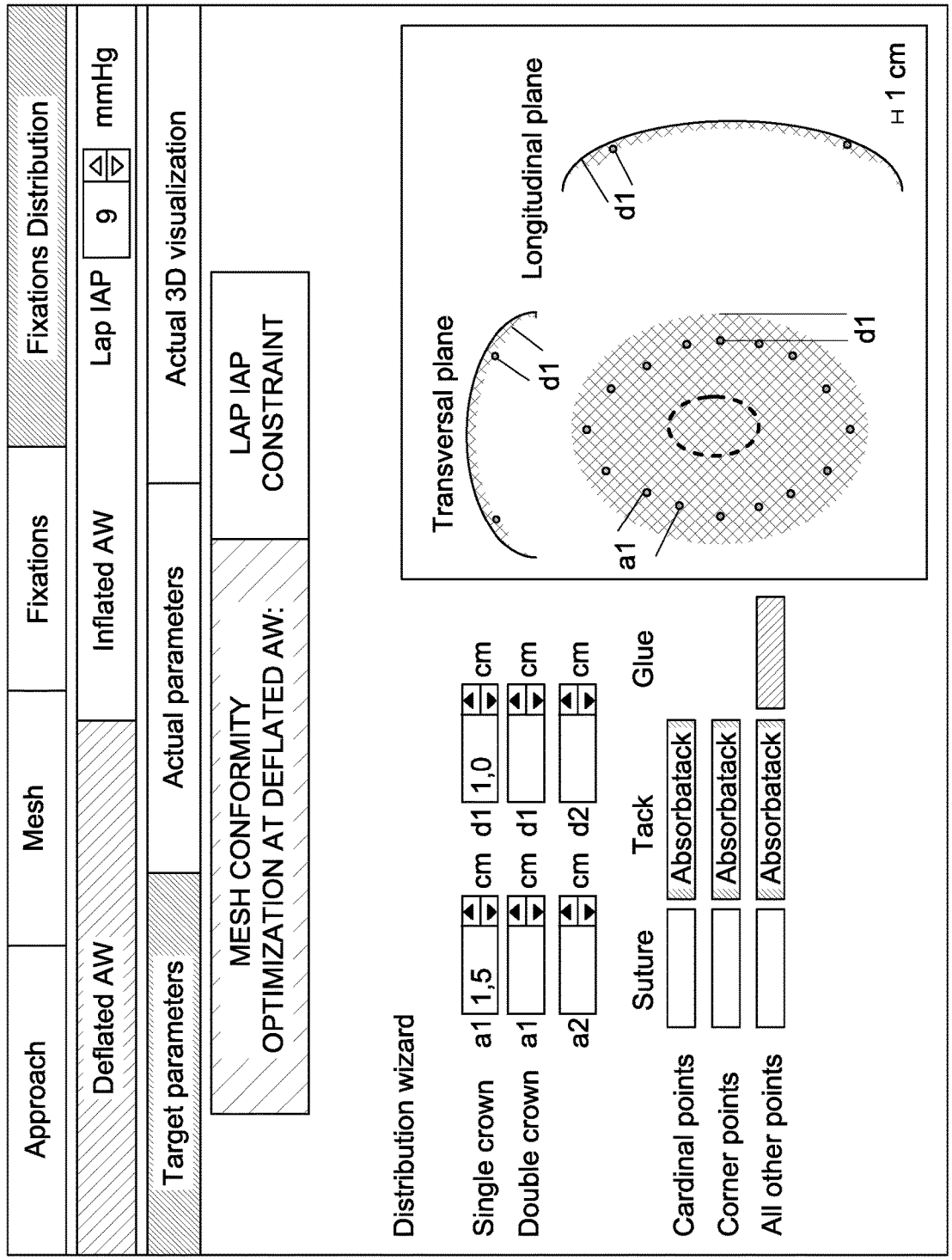

With reference to FIGS. 19A and 19B, upon selection of the "Lap IAP Constraint" optimization option (see FIG. 11), the clinician may indicate target fixation distribution parameters corresponding to a deflated condition of the abdominal wall and a Lap IAP at which the abdominal wall is to be inflated. In contrast to the "Non Lap IAP Constraint" optimization option, the application 116 does not generate an optimized Lap IAP in the "Lap IAP Constraint" option. Rather, the "Lap IAP Constraint" optimization option allows the clinician to specify the Lap IAP at which the abdominal wall is to be inflated for implantation of the hernia mesh.

Figure 20A:
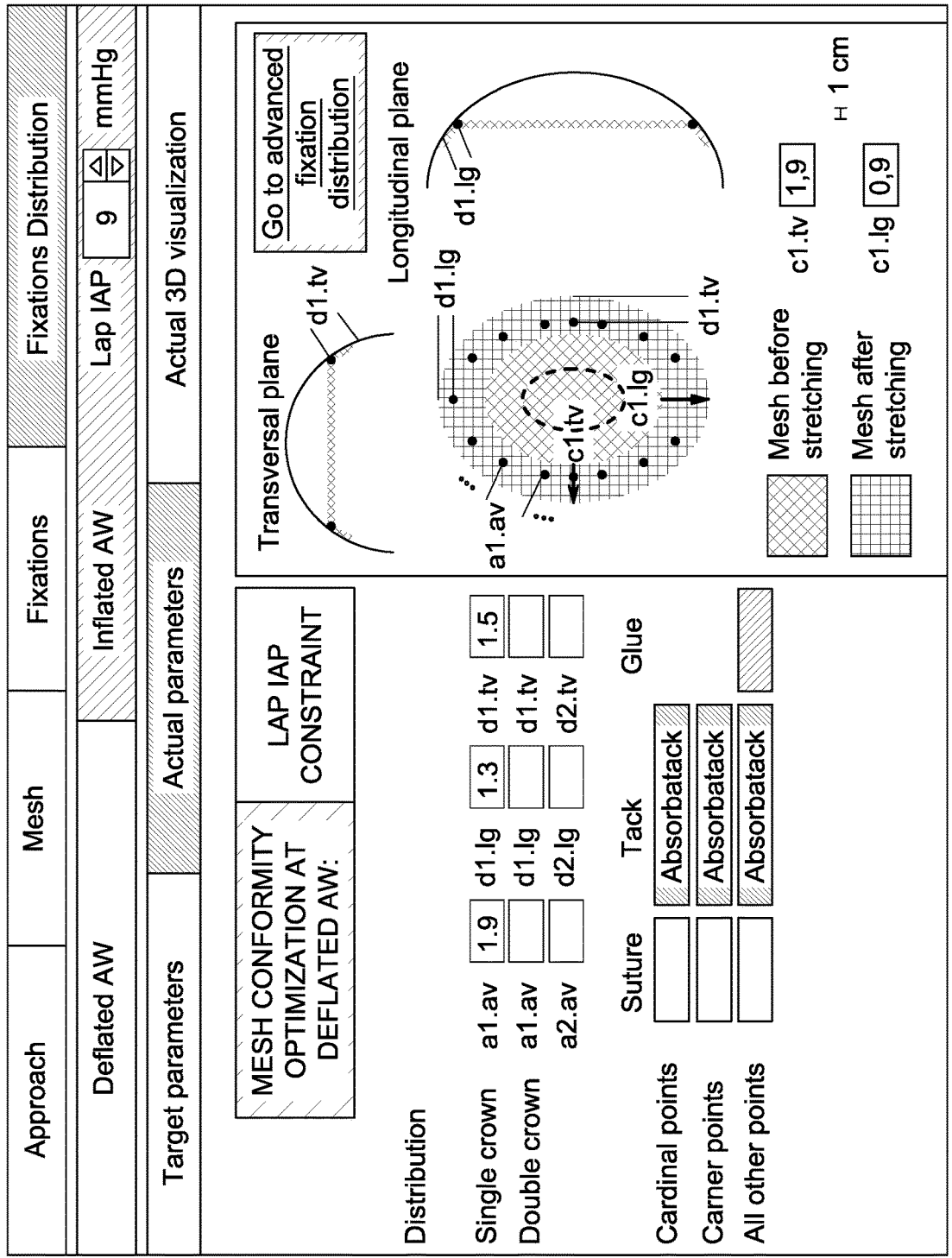
Figure 20B:
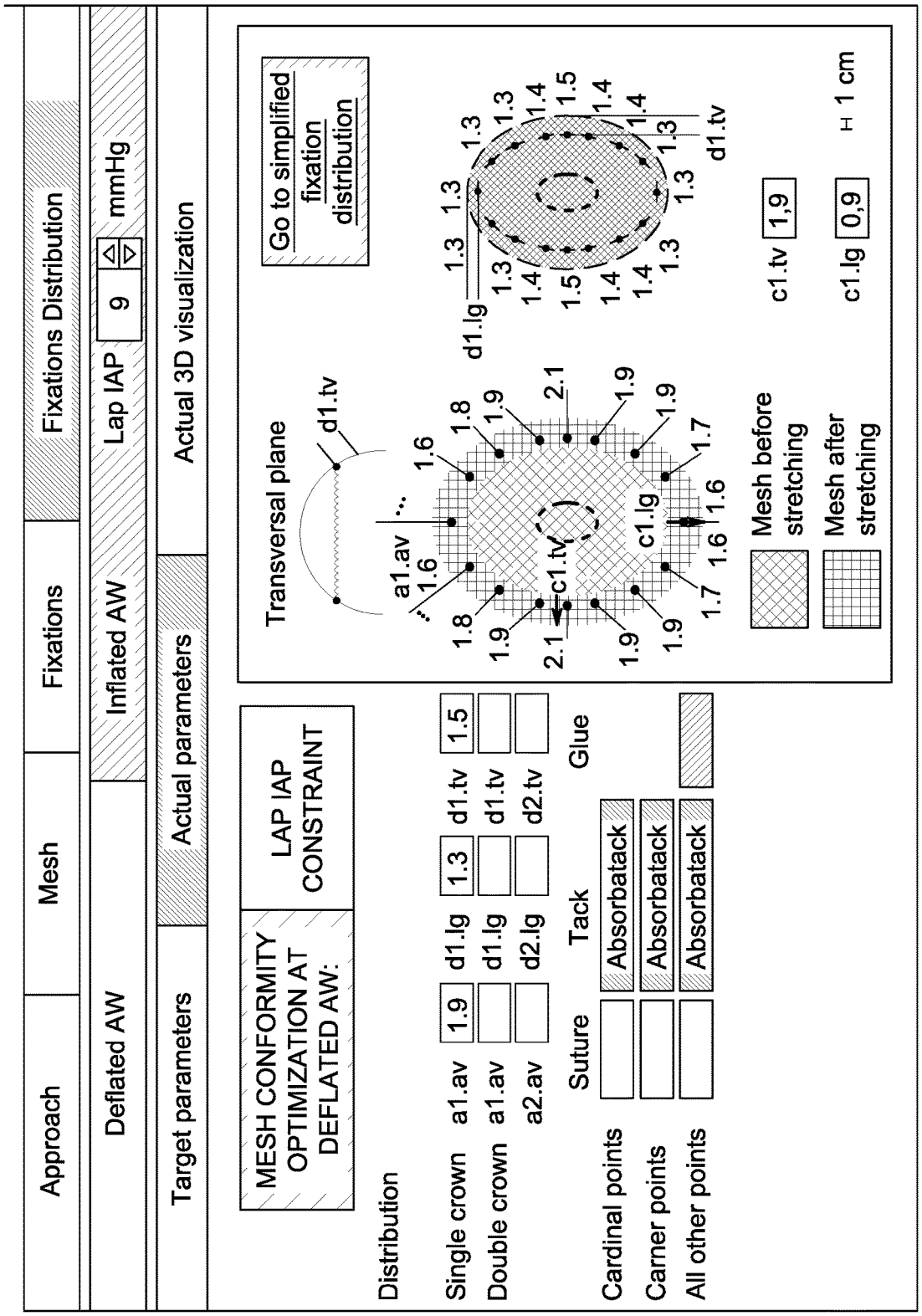

Once the clinician has specified target values for "a1" and "d1" (depicted in FIG. 19B as 1.5 and 1.0, respectively) and a value for Lap IAP (depicted in FIG. 19B as 9 mmHg), the clinician may select "Actual parameters" (FIGS. 20A and 20B), in response to which the application 116 generates optimized fixation distribution parameters for the distribution of fixations about the hernia mesh while the abdominal wall is inflated. These optimized fixation distribution parameters (depicted in FIGS. 20A and 20B as a1.av, d1.1g, and d1.tv) indicate to the clinician that applying these optimized fixation distribution parameters to the hernia mesh while the abdominal wall is inflated at the selected Lap IAP (e.g., 9 mmHg) will result in the target fixation distribution parameters previously indicated by the clinician (see FIG. 19B) upon return of the abdominal wall to the deflated condition. Substantially as described above with respect to FIGS. 15A and 15B, the clinician may choose to view the optimized fixation distribution under a "simplified fixation distribution" view as shown in FIG. 20A or under an "advanced fixation distribution" view as shown in FIG. 20B. As described hereinabove, since the "Lap IAP Constraint" mesh conformity optimization option allows the clinician to adjust the Lap IAP, stretching of the hernia mesh due to over-inflation of the abdominal wall may result. With this in mind, the clinician may be provided with a visualization of the hernia mesh before stretching and after stretching in conjunction with fixation distribution parameters so that the clinician can visualize the effects of inflating the abdominal wall to a particular Lap IAP (see FIGS. 20A and 20B).

Figure 21A:
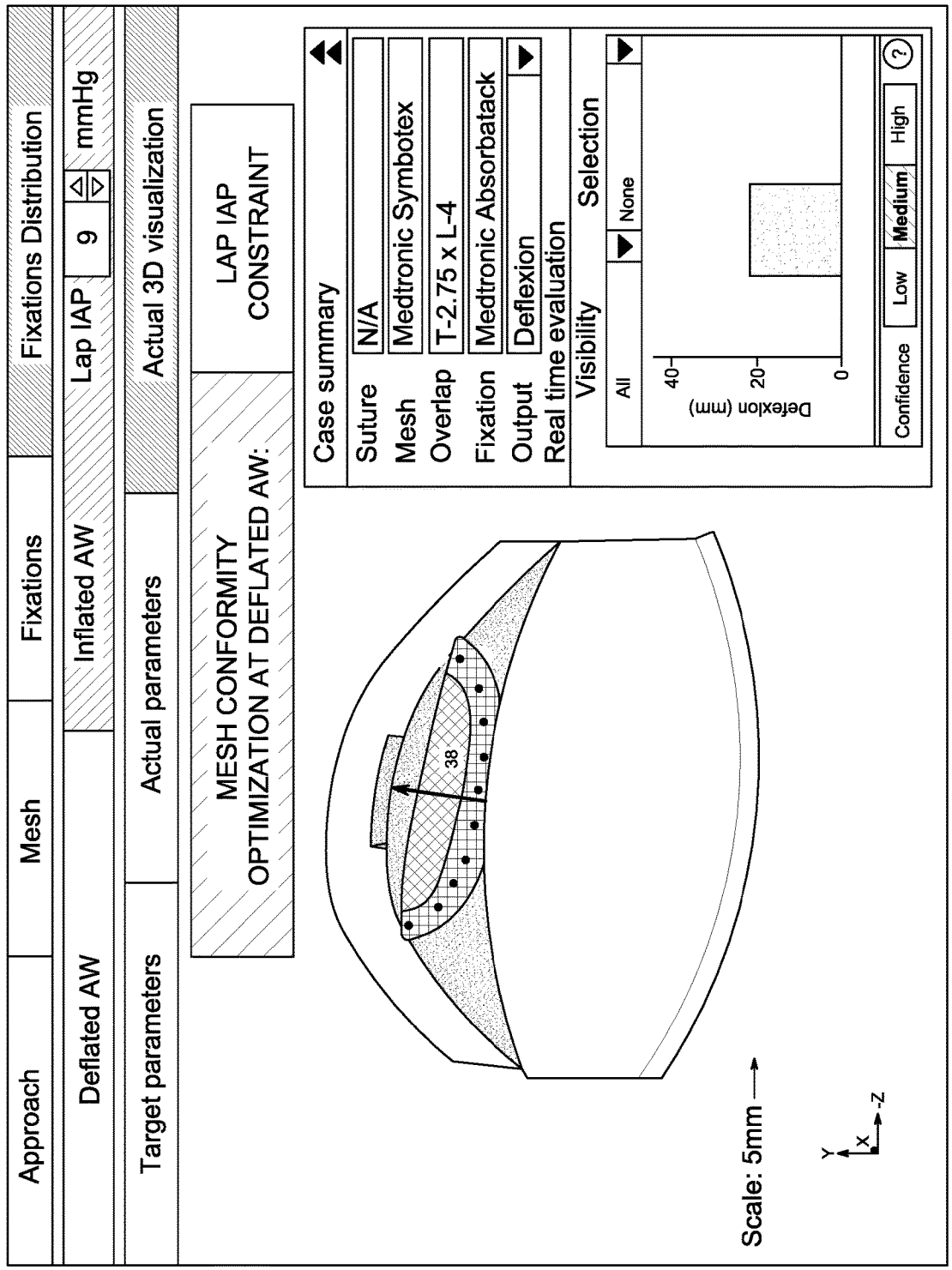
Figure 21B:
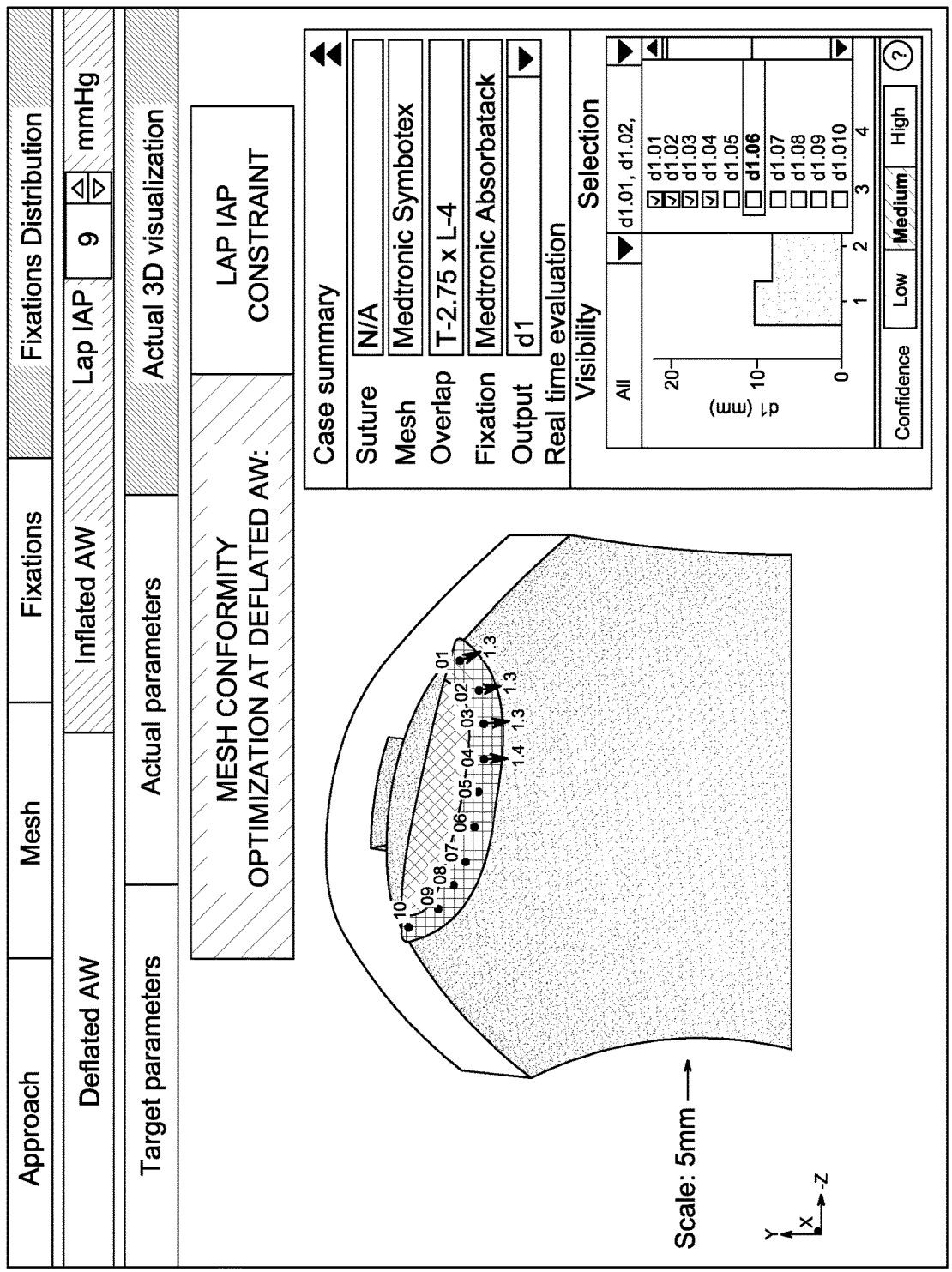
Figure 21C:
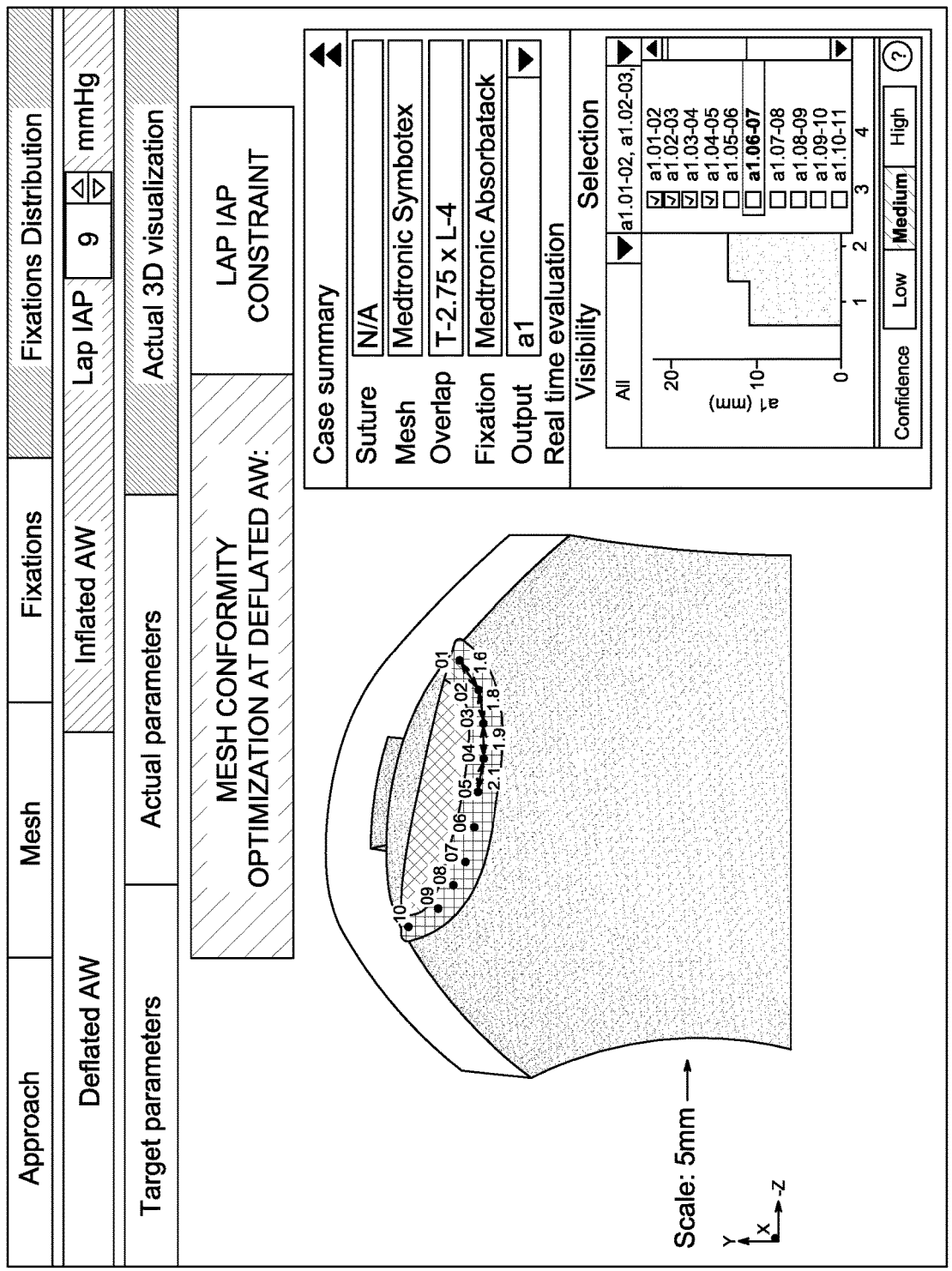

As shown in FIGS. 21A-21C, the clinician may choose to view an interactive 3D model of the hernia repair site when the abdominal wall is inflated at the selected Lap IAP, e.g., by selecting "Actual 3D visualization." Substantially as described above with respect to FIGS. 16A-16C, a "Case summary" of the interactive 3D model is displayed alongside the 3D model and includes a mesh type and size, overlap measurements, and fixation type, all of which were previously indicated and/or confirmed by the clinician. Additionally, an output may be selected by the clinician (e.g., via a pull-down menu) to visualize outputs relating to the fixation distribution when the abdominal wall is in the inflated condition such as, but not limited to, deflexion (FIG. 21A), d1 (FIG. 21B), or a1 (FIG. 21C).

Figure 22A:
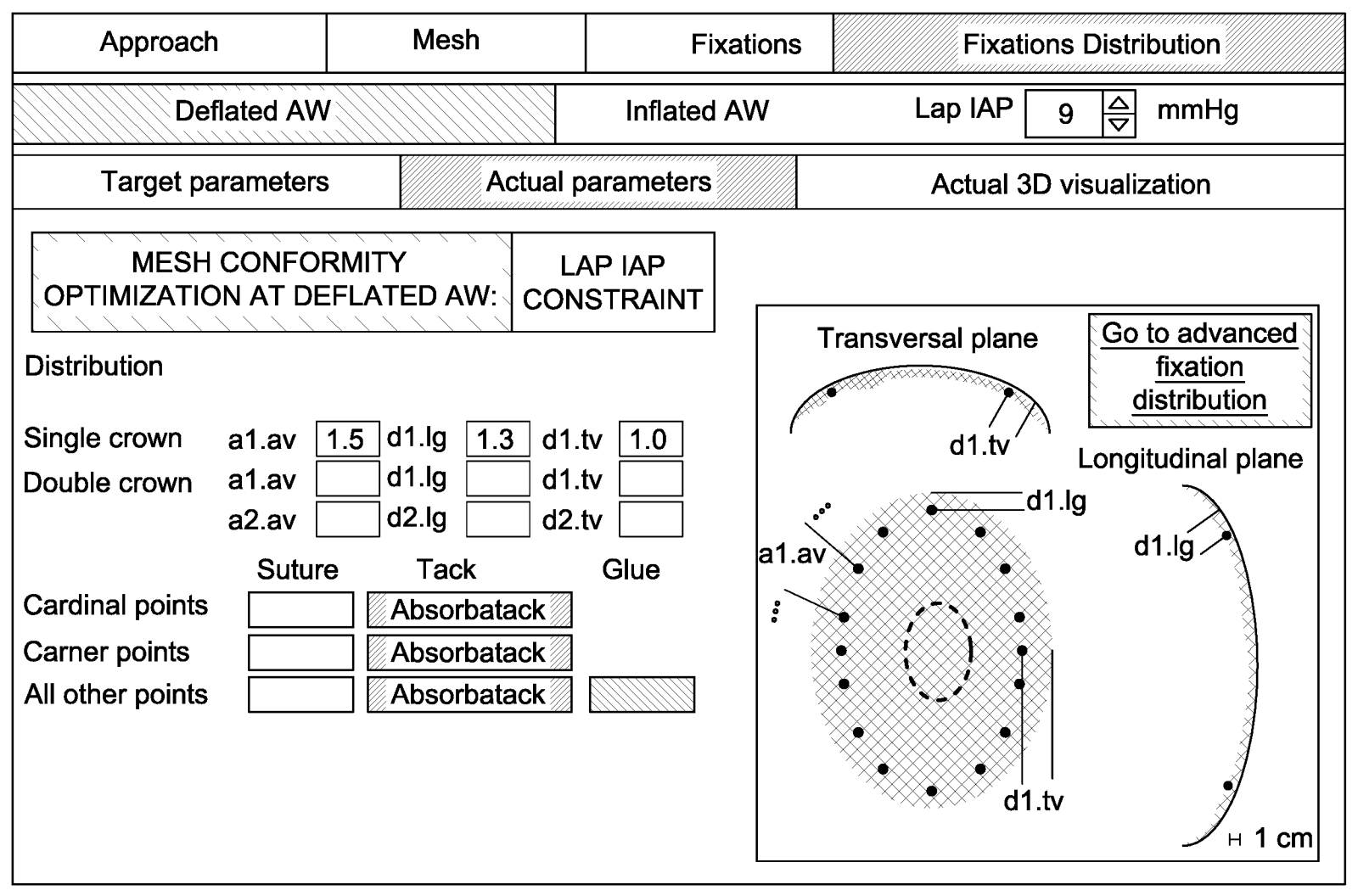
Figure 22B:
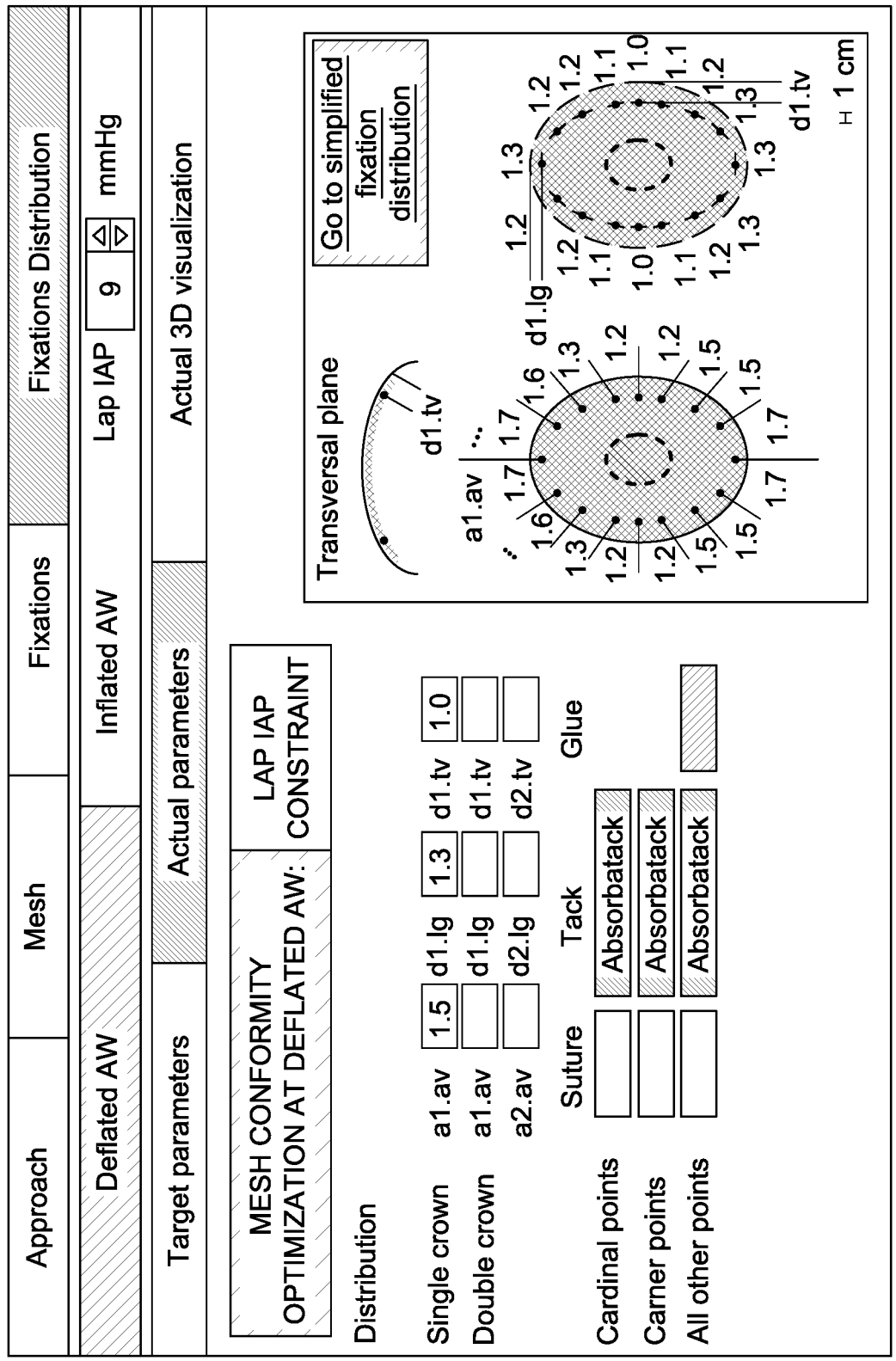

As shown in FIGS. 22A and 22B, the clinician may choose to view the "Actual parameters" relating to the fixation distribution when the abdominal wall is deflated resulting from the use of the "Actual parameters" while the abdominal wall was inflated (see FIGS. 20A and 20B). Substantially as described above with respect to FIGS. 15A and 15B, the clinician may choose to view the detailed fixation distribution under a "simplified fixation distribution" while the abdominal wall is in the deflated condition as shown in FIG. 22A or under an "advanced fixation distribution" while the abdominal wall is in the deflated condition as shown in FIG. 22B.

Figure 23A:
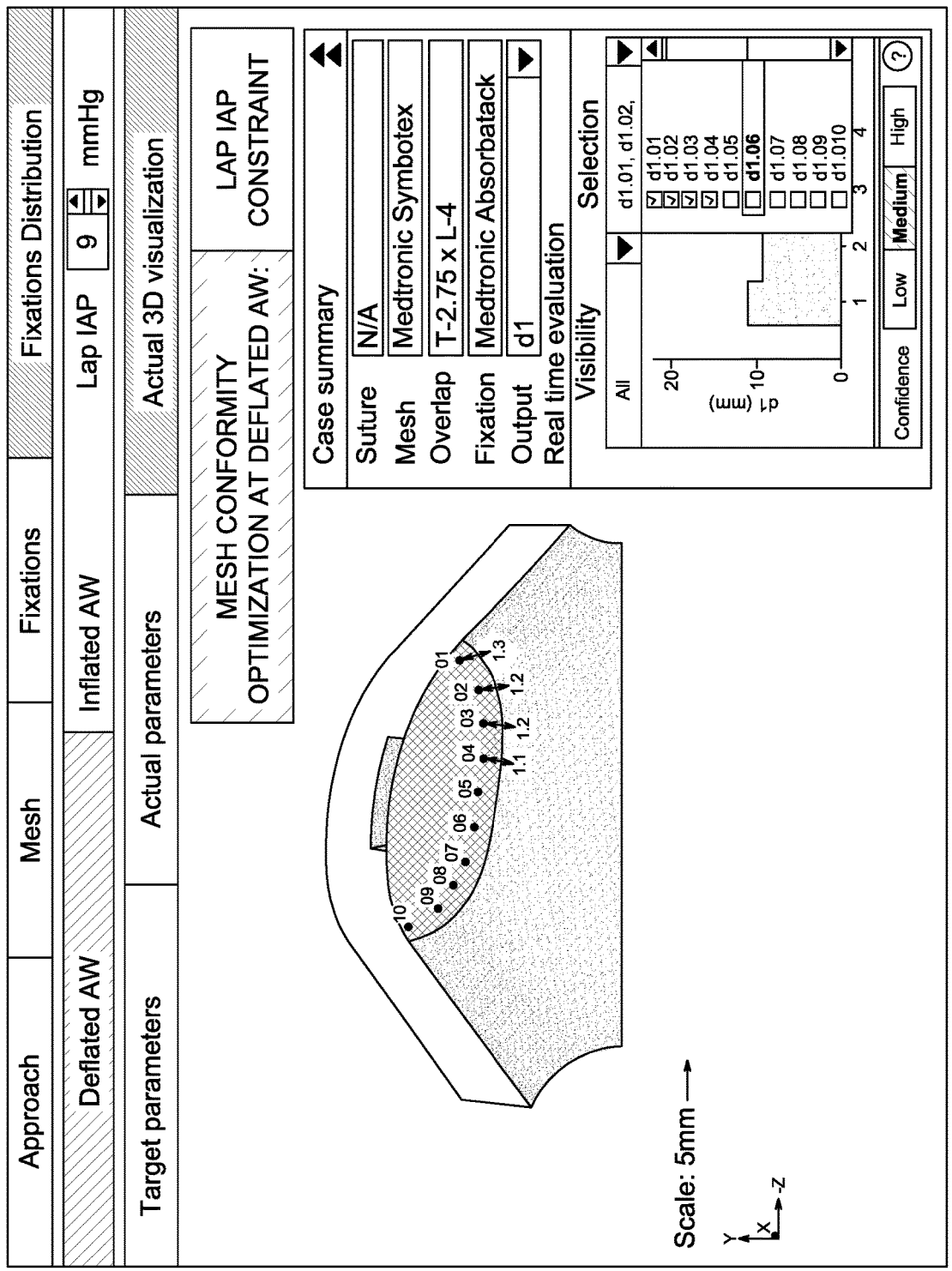
Figure 23B:
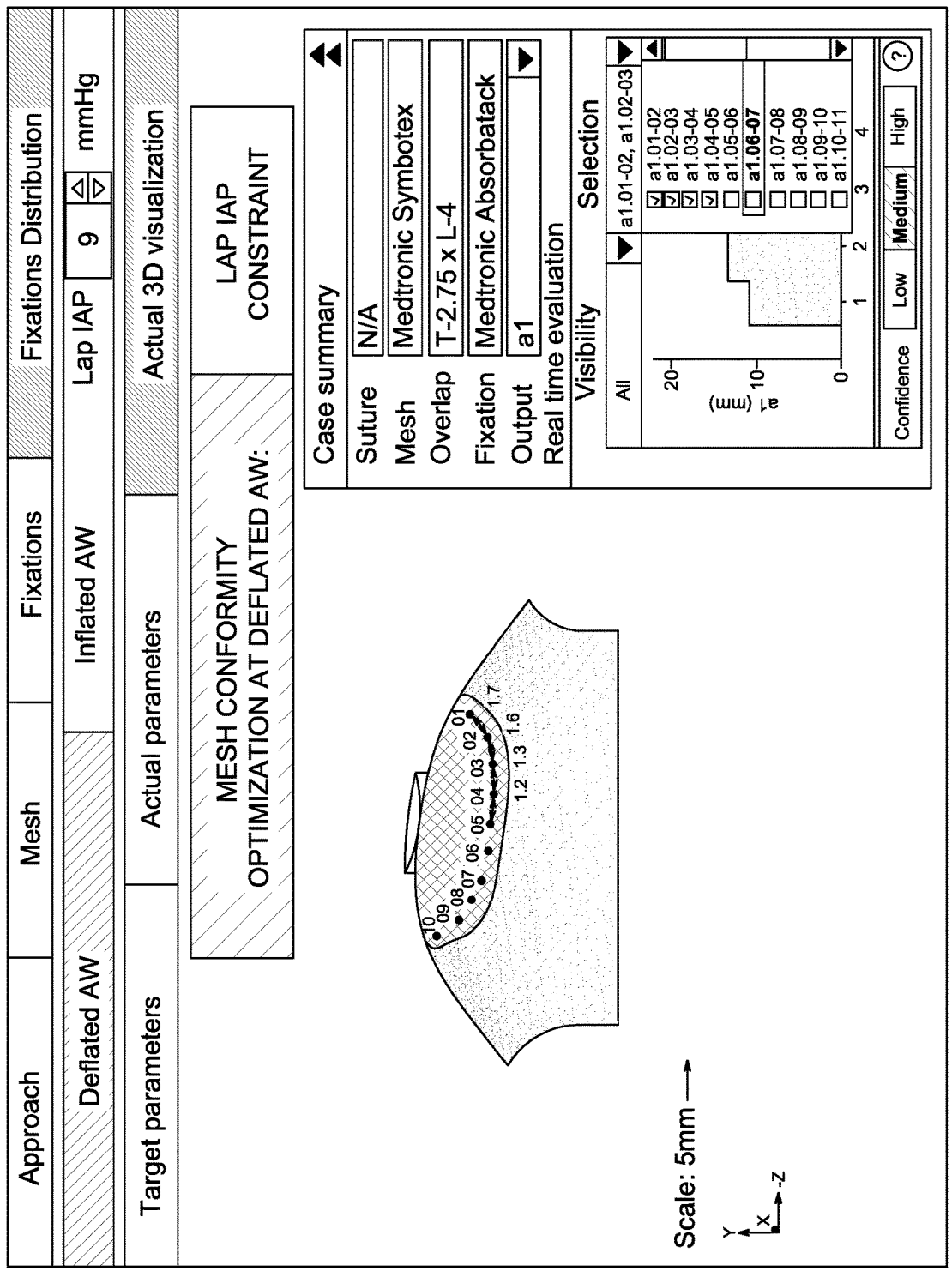

Substantially as described above with respect to FIGS. 18A and 18B, the clinician may choose to view an interactive 3D model of the hernia repair site when the abdominal wall is returned to a deflated state, e.g., by selecting "Actual 3D visualization," as shown in FIGS. 23A and 23B. A "Case summary" of the interactive 3D model and a "Real time evaluation" is displayed alongside the 3D model substantially as described above with respect to FIGS. 16A-16C. Additionally, an output may be selected by the clinician (e.g., via a pull-down menu) to visualize outputs relating to the fixation distribution when the abdominal wall is in the deflated condition such as, but not limited to, d1 (FIG. 23A) and a1 (FIG. 23B).

"No" Mesh Conformity Optimization Option

The "No" mesh conformity optimization option (see FIG. 11) is substantially similar to the "Non Lap IAP Constraint" and "Lap IAP Constraint" mesh conformity optimization options and is only described herein to the extent necessary to describe the differences in the process of the "No" mesh conformity optimization option.

Figure 24A:
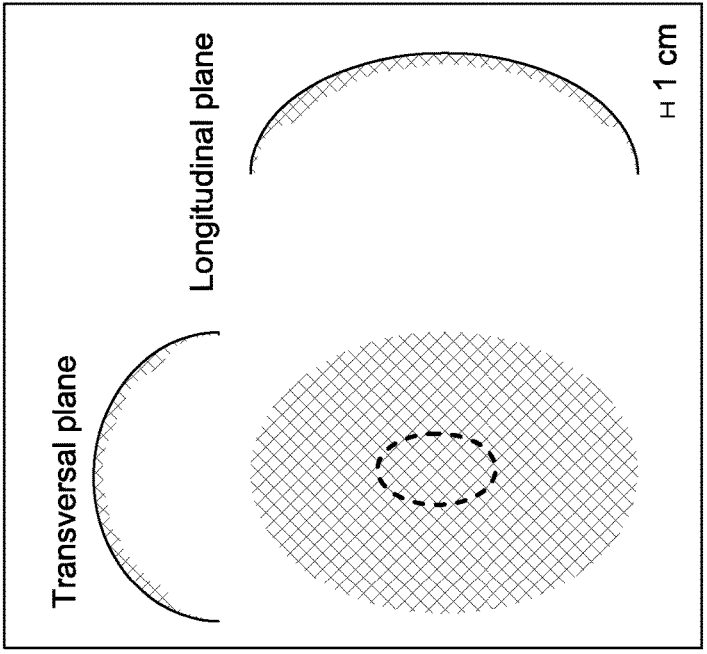
FIGS. 24A-28B are illustrations of a user interface presenting an editable fixation distribution process in connection with a step of selecting the "NO" mesh conformity optimization option presented in FIG. 11 according to an embodiment of the present disclosure.
Figure 24B:
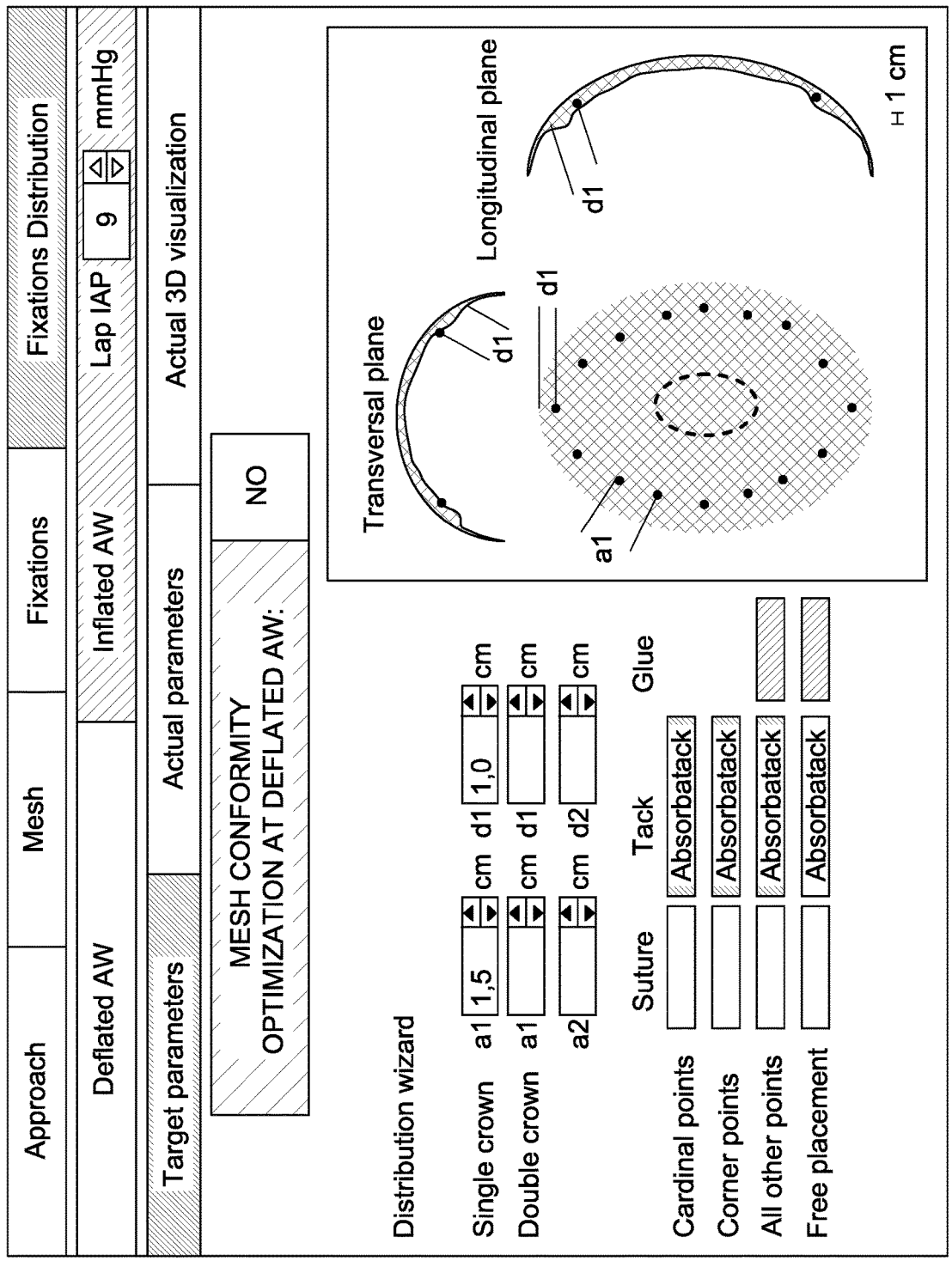

With reference to FIGS. 24A and 24B, upon selection of the "No" mesh conformity optimization option (see FIG. 11), the clinician may indicate target fixation distribution parameters corresponding to an inflated condition of the abdominal wall and a Lap IAP at which the abdominal wall is to be inflated to achieve a target fixation distribution. In contrast to the "Non Lap IAP Constraint" and "Lap IAP Constraint" mesh conformity optimization options, the application 116 does not generate optimized fixation distribution parameters corresponding to an inflated condition of the abdominal wall in the "No" mesh conformity optimization option. Nor does the application 116 generate an optimized Lap IAP in the "No" mesh conformity optimization option. Rather, the "No" mesh conformity optimization option allows the clinician to specify the target fixation distribution parameters corresponding to an inflated condition of the abdominal wall and the Lap IAP at which the abdominal wall is to be inflated for implantation of the hernia mesh.

Figure 25A:
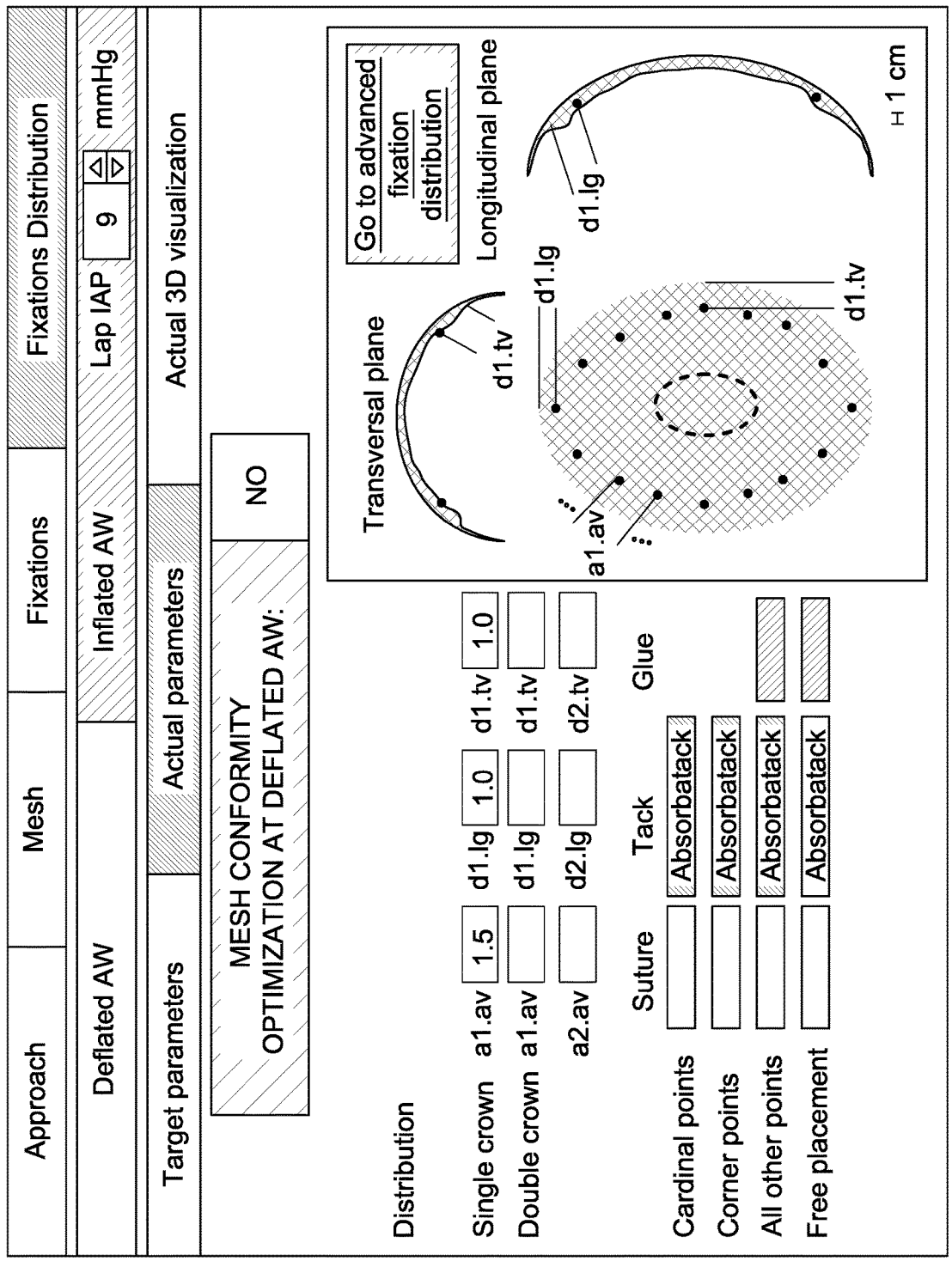
Figure 25B:
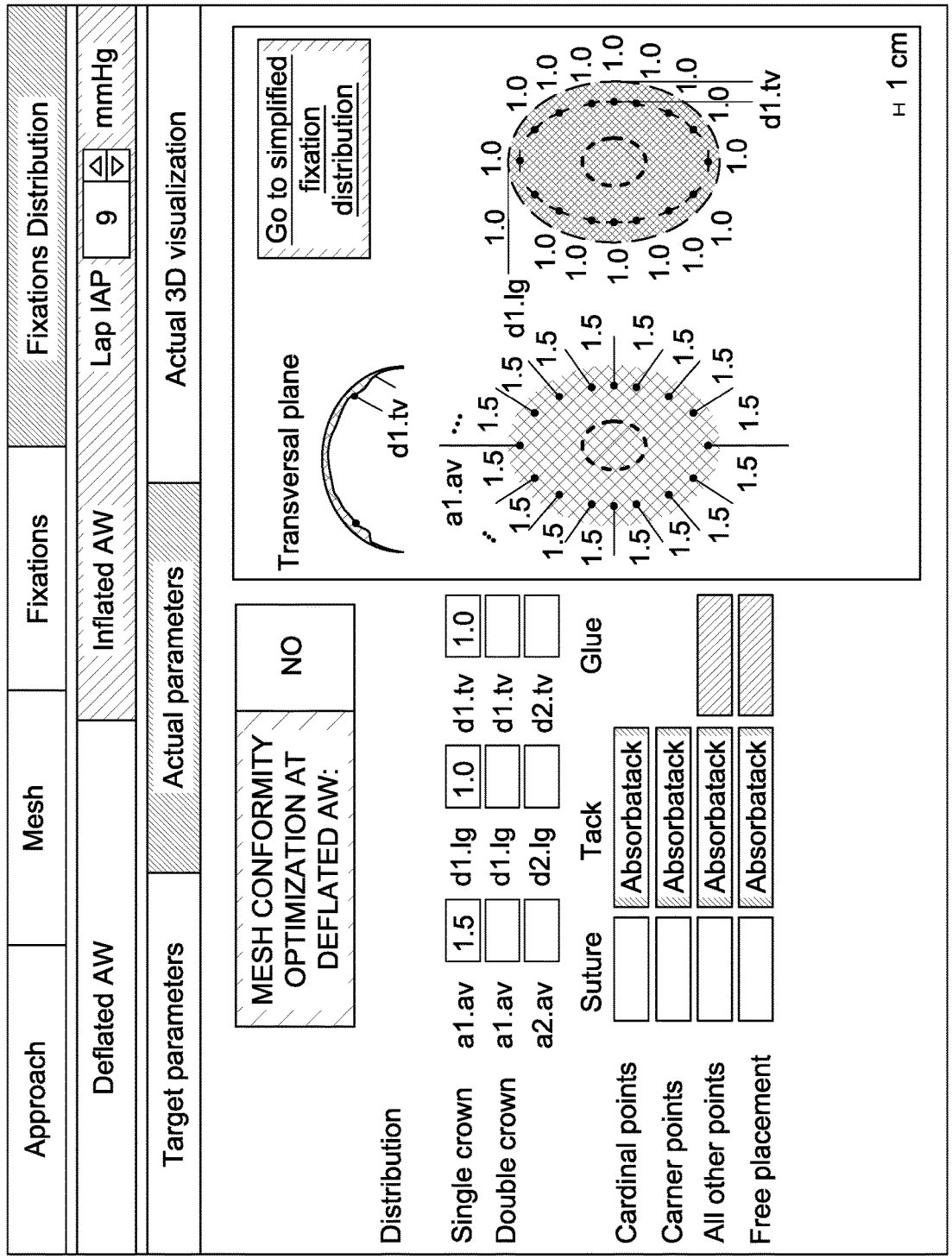

Once the clinician has specified target values for "a1" and "d1" (depicted in FIG. 24B as 1.5 and 1.0, respectively) and a value for Lap IAP (depicted in FIG. 24B as 9 mmHg), the clinician may select "Actual parameters" (FIGS. 25A and 25B), in response to which the application 116 generates the details of the target distribution parameters (depicted in FIGS. 25A and 25B as a1.av, d1.1g, and d1.tv) selected by the clinician for the distribution of fixations about the hernia mesh while the abdominal wall is inflated. More specifically, and as shown in FIGS. 25A and 25B, the application 116 generates an actual distribution of the fixation about the implantable repair material when the abdominal wall of the patient is inflated based on the target fixation distribution parameters and the indicated IAP. Substantially as described above with respect to FIGS. 15A and 15B, the clinician may choose to view the detailed fixation distribution under a "simplified fixation distribution" view while the abdominal wall is in the inflated condition as shown in FIG. 25A or under an "advanced fixation distribution" view while the abdominal wall is in the inflated condition as shown in FIG. 25B.

Figure 26A:
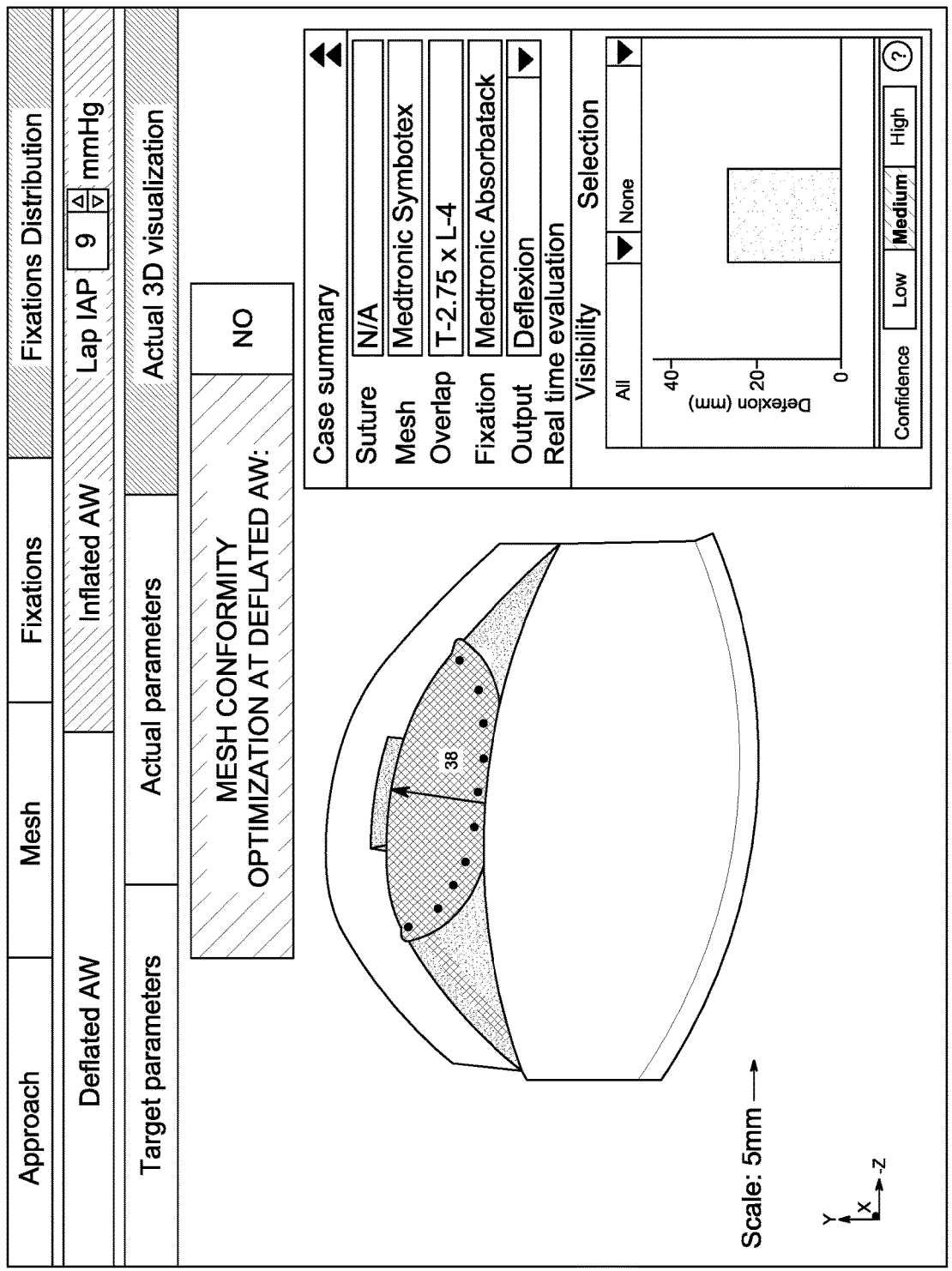
Figure 26B:
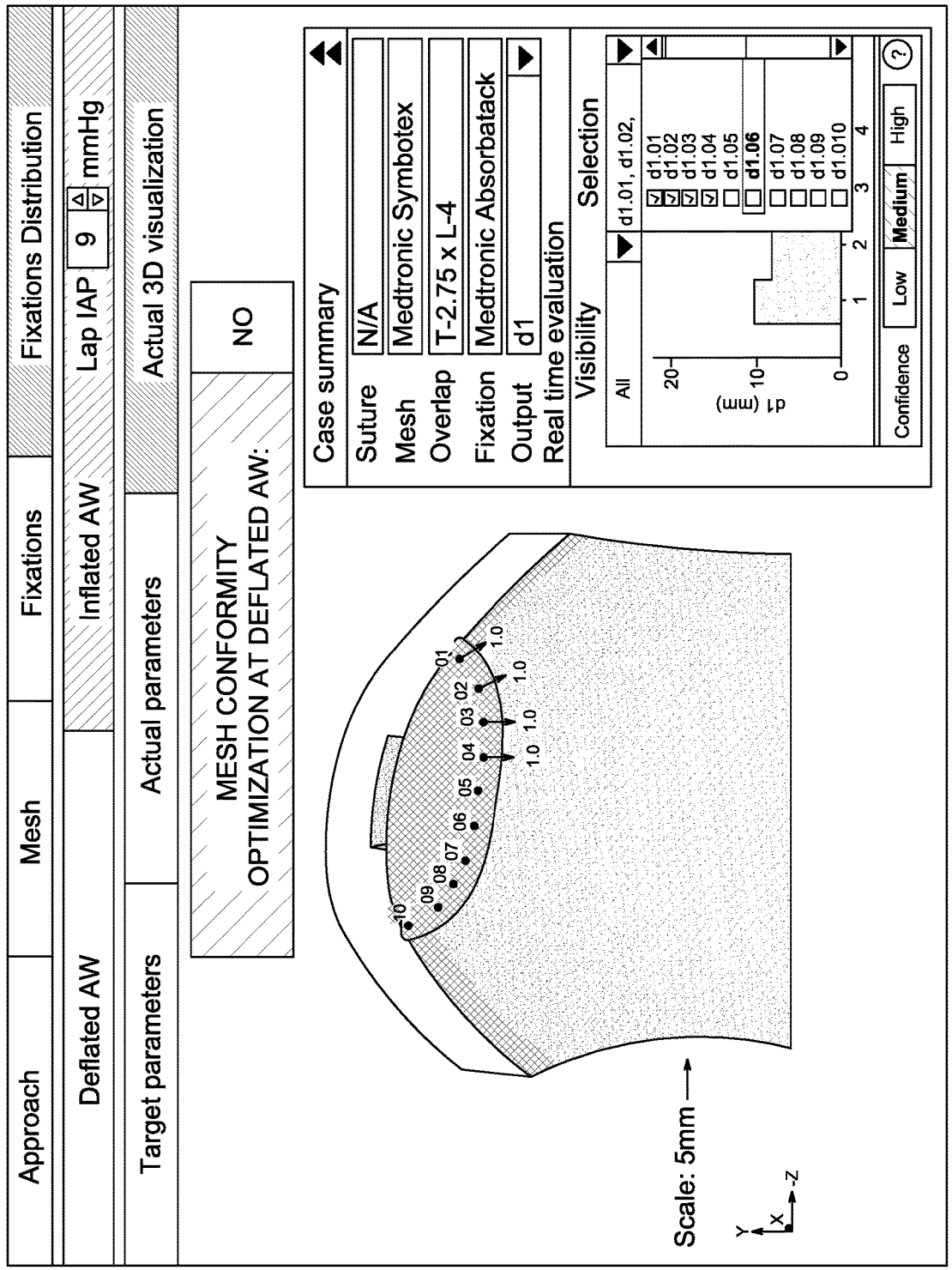
Figure 26C:
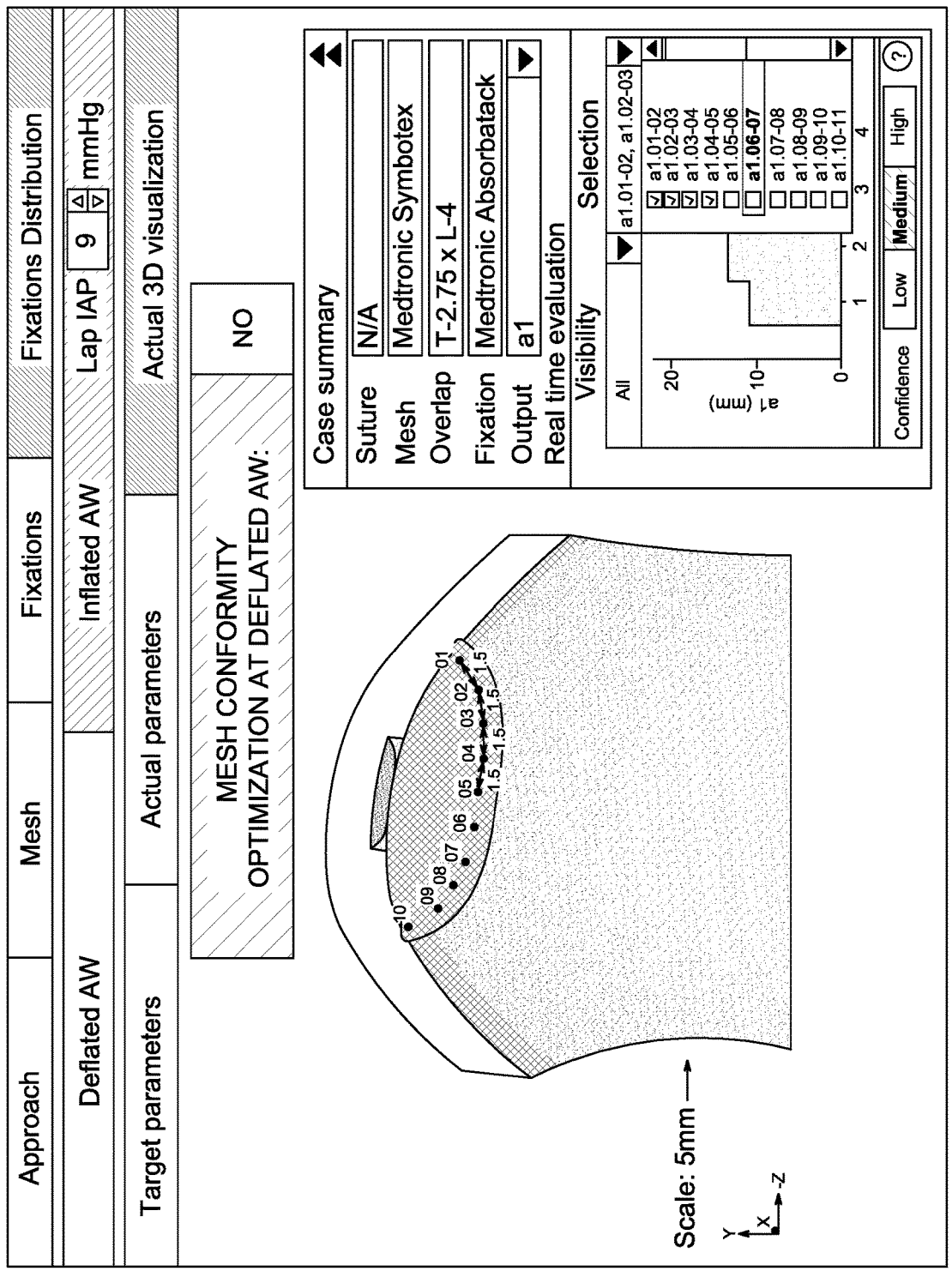

As shown in FIGS. 26A-26C, the clinician may choose to view an interactive 3D model of the hernia repair site when the abdominal wall is inflated at the selected Lap IAP, e.g., by selecting "Actual 3D visualization." Substantially as described above with respect to FIGS. 16A-16C, a "Case summary" of the interactive 3D model is displayed alongside the 3D model and includes a suture type, mesh type and size (or suture type and size), overlap measurements, and fixation type, all of which were previously indicated and/or confirmed by the clinician or otherwise based on a clinical profile provided to the computing device 100. Additionally, an output may be selected by the clinician (e.g., via a pull-down menu) to visualize outputs relating to the fixation distribution when the abdominal wall is in the inflated condition such as, but not limited to, deflexion (FIG. 26A), d1 (FIG. 26B), or a1 (FIG. 26C).

Figure 27A:
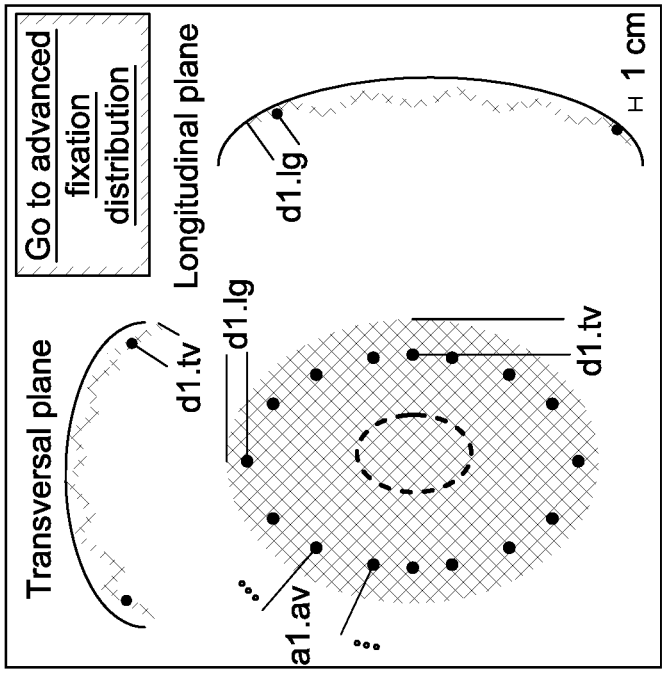
Figure 27B:
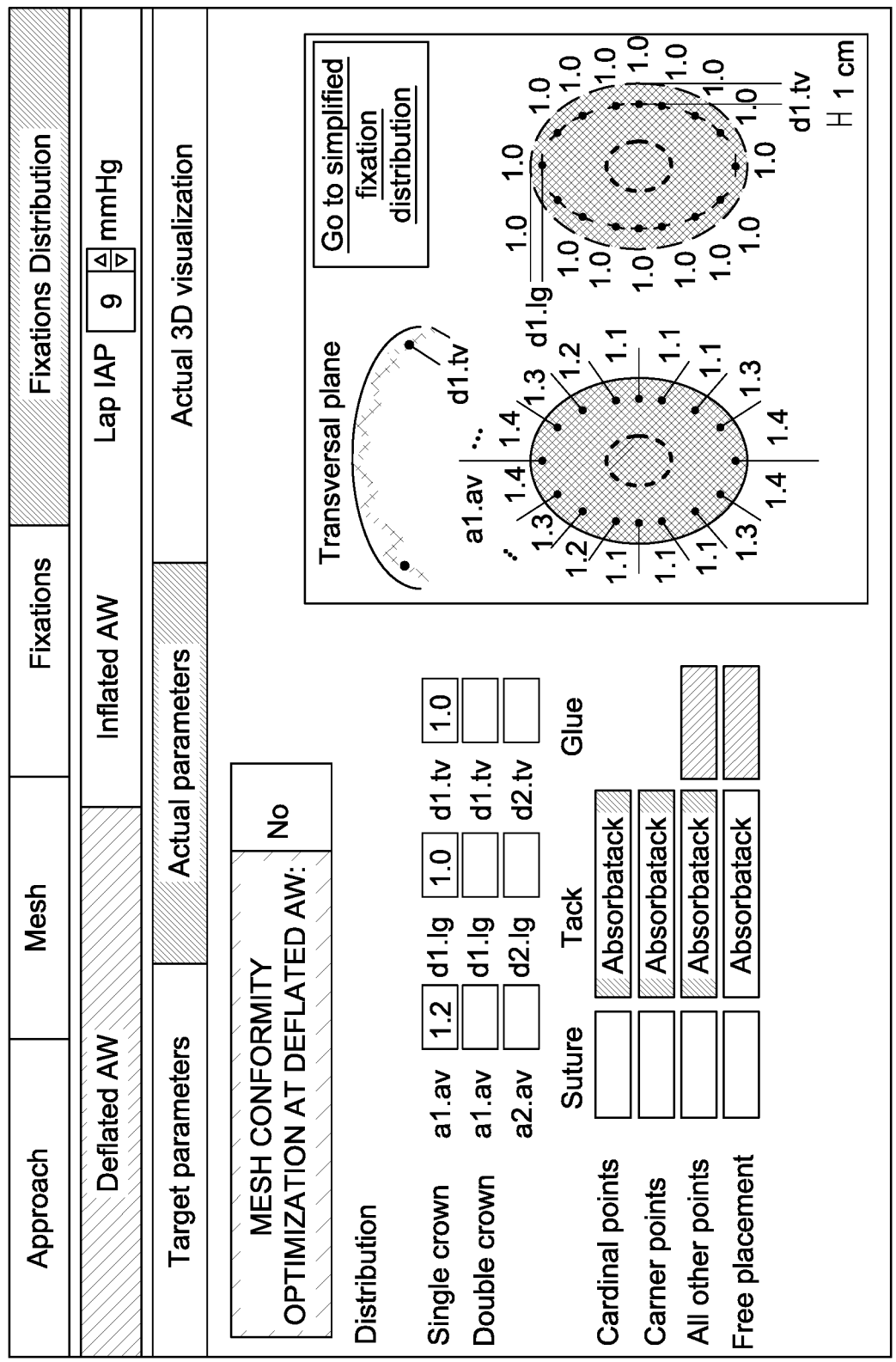

As shown in FIGS. 27A and 27B, the clinician may choose to view the "Actual parameters" relating to the fixation distribution when the abdominal wall is deflated resulting from the use of the "Actual parameters" while the abdominal wall was inflated at the selected Lap IAP (see FIGS. 25A and 25B). More specifically, FIGS. 27A and 27B show the detailed fixation distribution that results upon return of the abdominal wall to the deflated condition if the clinician applied the target fixation distribution parameters to the hernia mesh while the abdominal wall was inflated at the selected Lap IAP (see FIG. 24B). Substantially as described above with respect to FIGS. 15A and 15B, the clinician may choose to view the detailed fixation distribution under a "simplified fixation distribution" view while the abdominal wall is deflated as shown in FIG. 27A or under an "advanced fixation distribution" while the abdominal wall is deflated as shown in FIG. 27B.

Figure 28A:
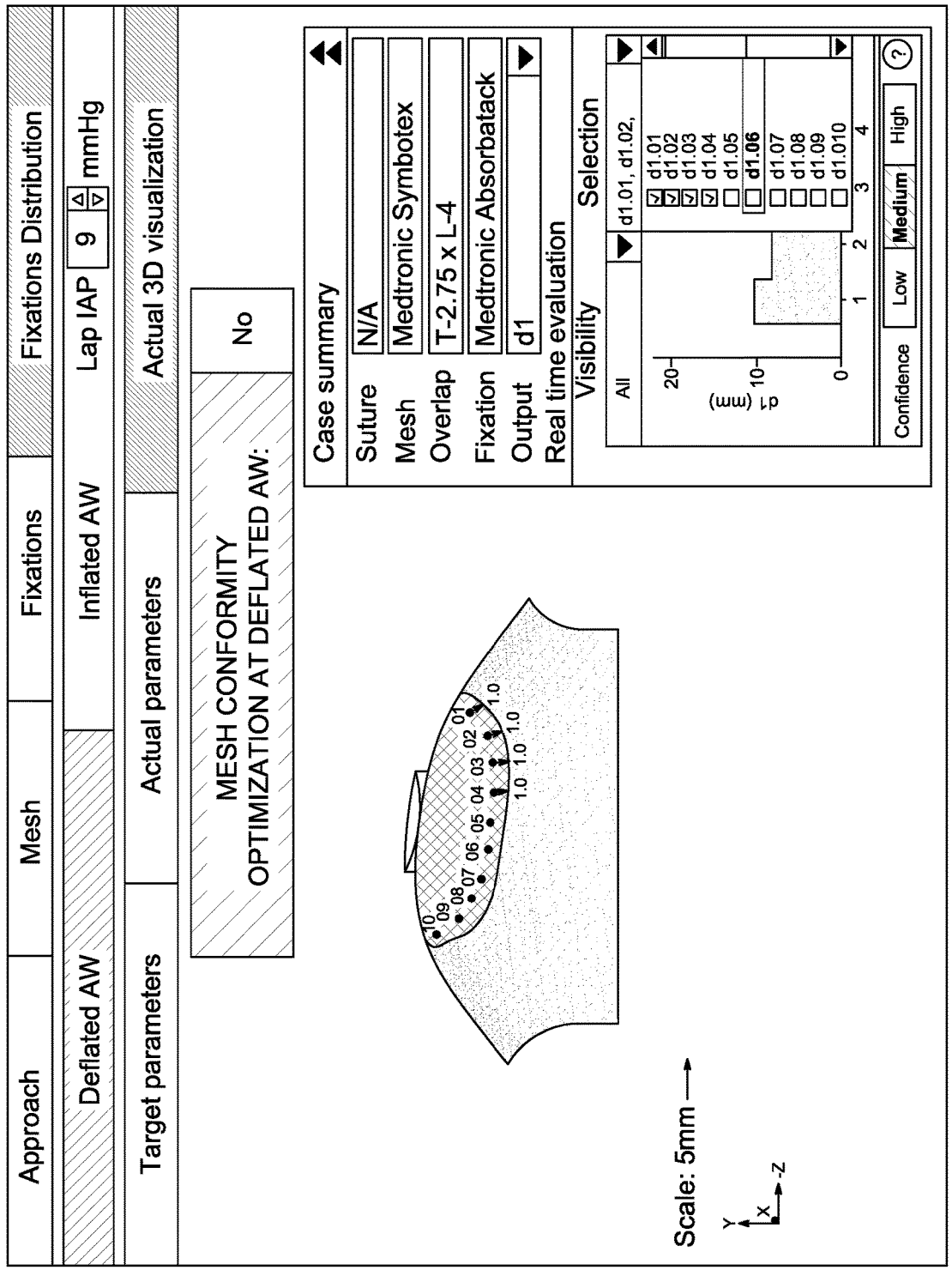
Figure 28B:
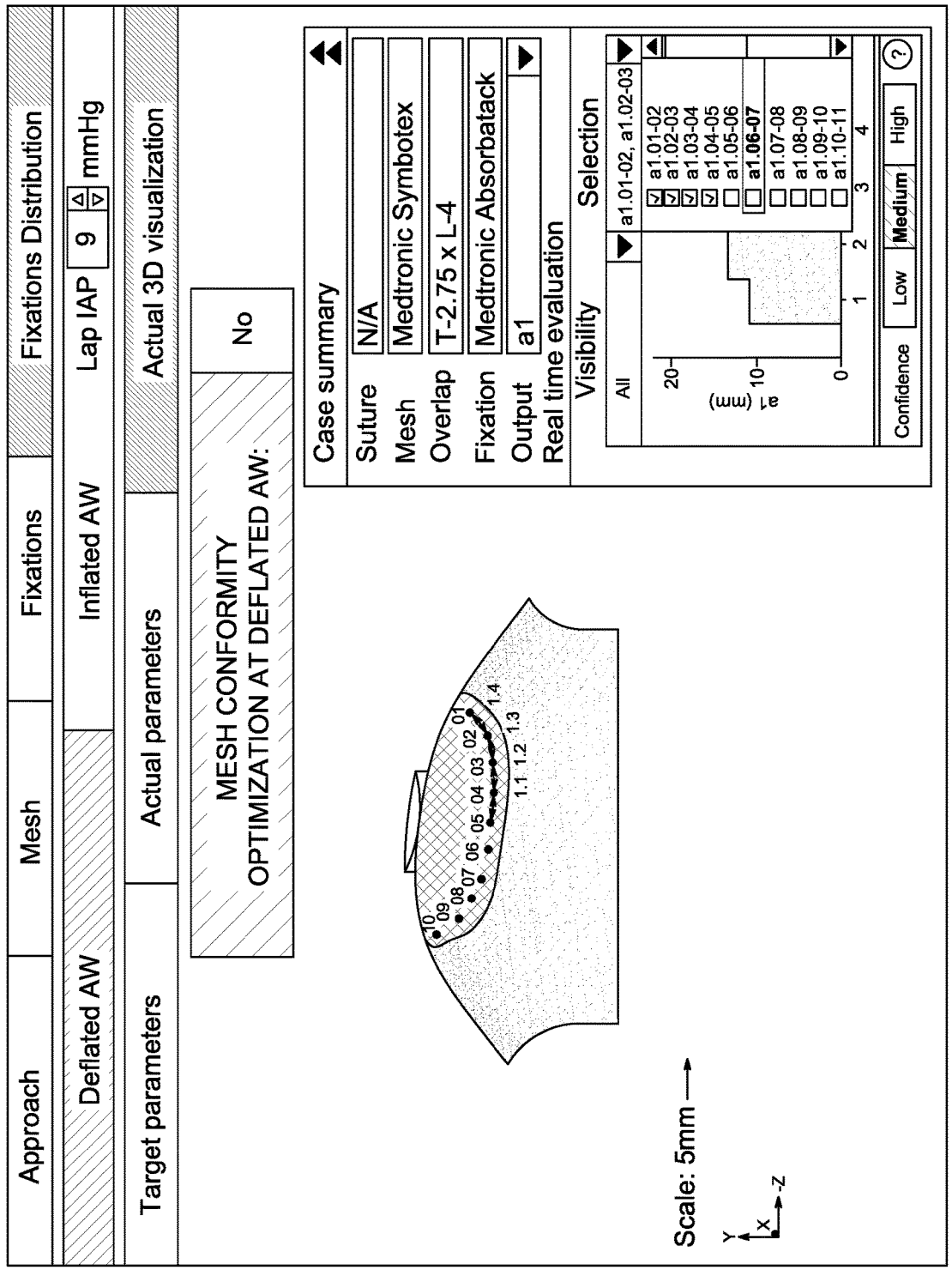

Substantially as described above with respect to FIGS. 18A and 18B, the clinician may choose to view an interactive 3D model of the hernia repair site when the abdominal wall is returned to a deflated state, e.g., by selecting "Actual 3D visualization," as shown in FIGS. 28A and 28B. A "Case summary" of the interactive 3D model and a "Real time evaluation" is displayed alongside the 3D model substantially as described above with respect to FIGS. 16A-16C. Additionally, an output may be selected by the clinician (e.g., via a pull-down menu) to visualize outputs relating to the fixation distribution when the abdominal wall is in the deflated condition such as, but not limited to, d1 (FIG. 28A) and a1 (FIG. 28B).

Figure 29A:
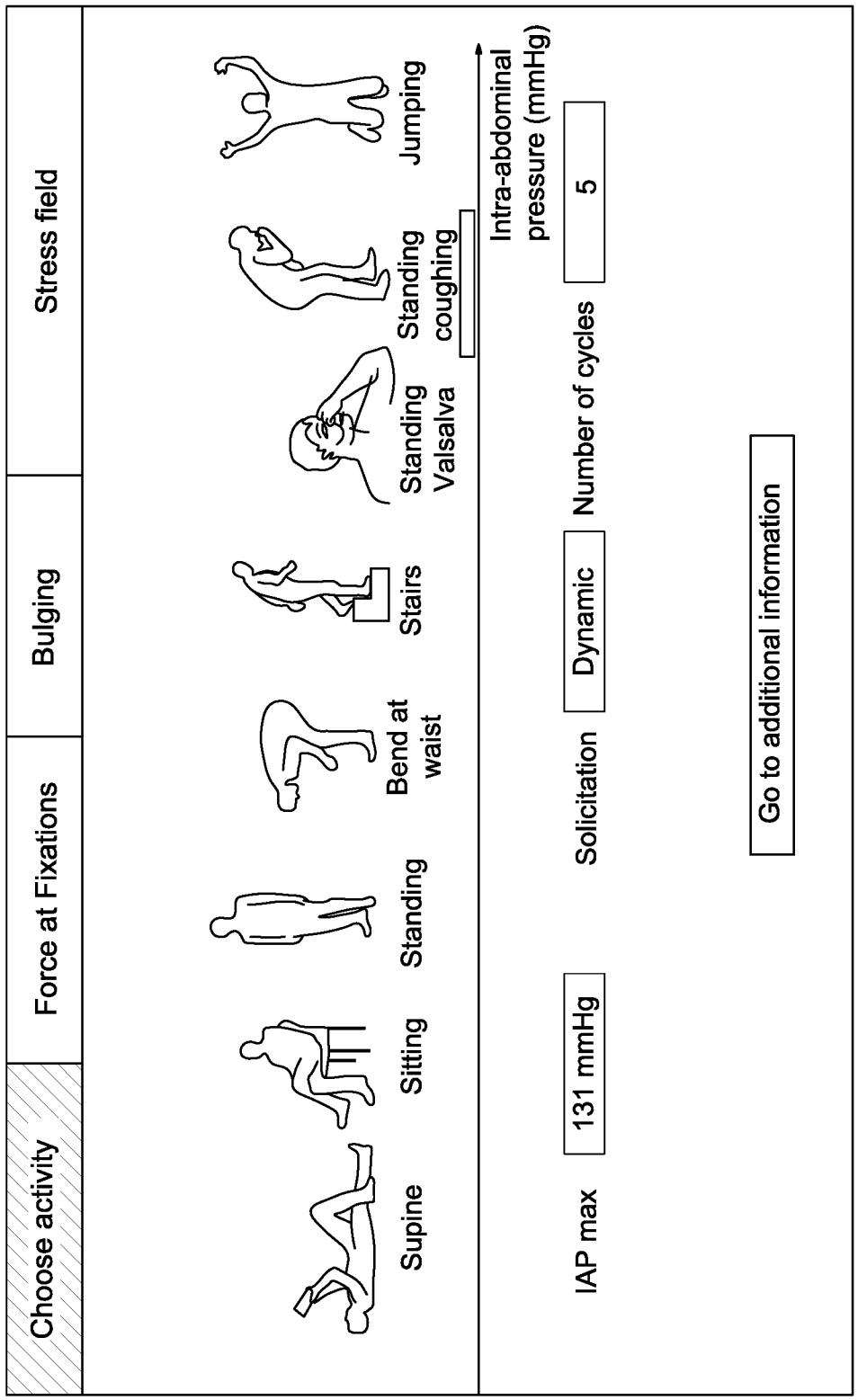
FIGS. 29A and 29B are illustrations of a user interface presenting a view showing a step of indicating a patient activity in accordance with an embodiment of the present disclosure.
Figure 29B:
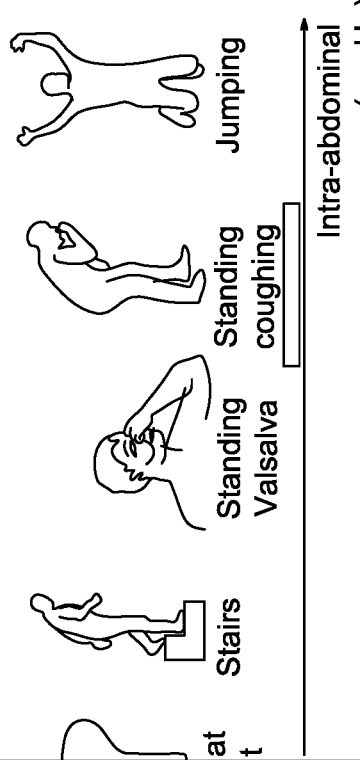

Step 240 includes indicating a patient activity from a menu of patient activities, as shown in FIGS. 29A and 29B. For example, patient activities may include, but are not limited to supine, sitting, standing, bend at waist, walking on stairs, standing valsalva, standing coughing, and jumping. Patient activities may be indicated through selection from a pull down menu, a list menu, or from a slide scale menu as shown in the illustrated embodiment of FIGS. 29A and 29B. For each patient activity indicated, a number of cycles (e.g., number of standing coughs) and a solicitation (e.g., dynamic in the case of jumping or static in the case of sitting) may be displayed. Additionally, an IAP maximum may be displayed as a number value expressed in mmHg (shown in FIG. 29A as "IAP max") and is generated by the application 116 based on the biomechanical profile of the patient, which may include a set of conditions that vary over the duration of time that the indicated patient activity is performed. The clinician may optionally change the IAP maximum number value directly or changing the IAP maximum number value may be effected by the clinician making changes to the biomechanical profile (e.g., changing the muscle contractibility). The clinician may be provided an option to display the set of conditions (e.g., by selecting "Go to additional information" shown in FIG. 29A) on the display 110, as shown in FIG. 29B. The set of conditions may include, but are not limited to, rectus contraction, external oblique contraction, internal oblique contraction, transverse contraction, diaphragm contraction, activity, posture, solicitation type, cycles, and IAP activity range. The IAP activity range may be displayed to illustrate where the IAP max ranks for that patient relative to a minimum and a maximum of a larger population of patients. In some embodiments, the minimum and/or average IAP may alternatively or additionally be displayed substantially as described above with respect to the maximum IAP. Depending on the gender of the patient, patient activities may be depicted using female patient illustrations or male patient illustrations. In the illustrated example of FIGS. 29A and 29B, various patient activities are presented with corresponding depictions of a male patient performing the various patient activities and "Standing coughing" is indicated as the patient activity.

Figure 30A:
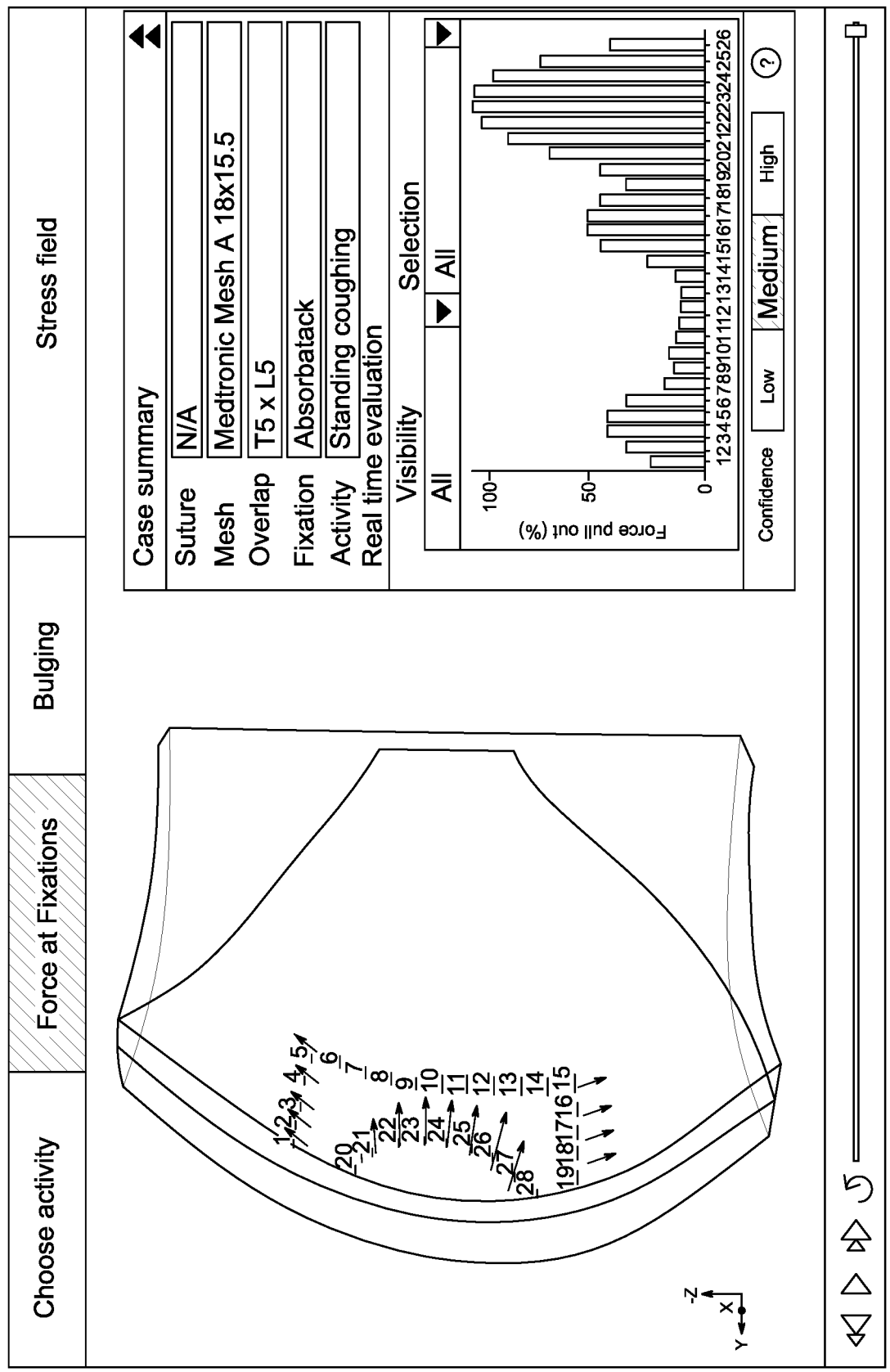
FIGS. 30A-30C are illustrations of a user interface showing a step of generating a simulation of an effect of a patient activity on surgical repair site in accordance with an embodiment of the present disclosure.
Figure 30B:
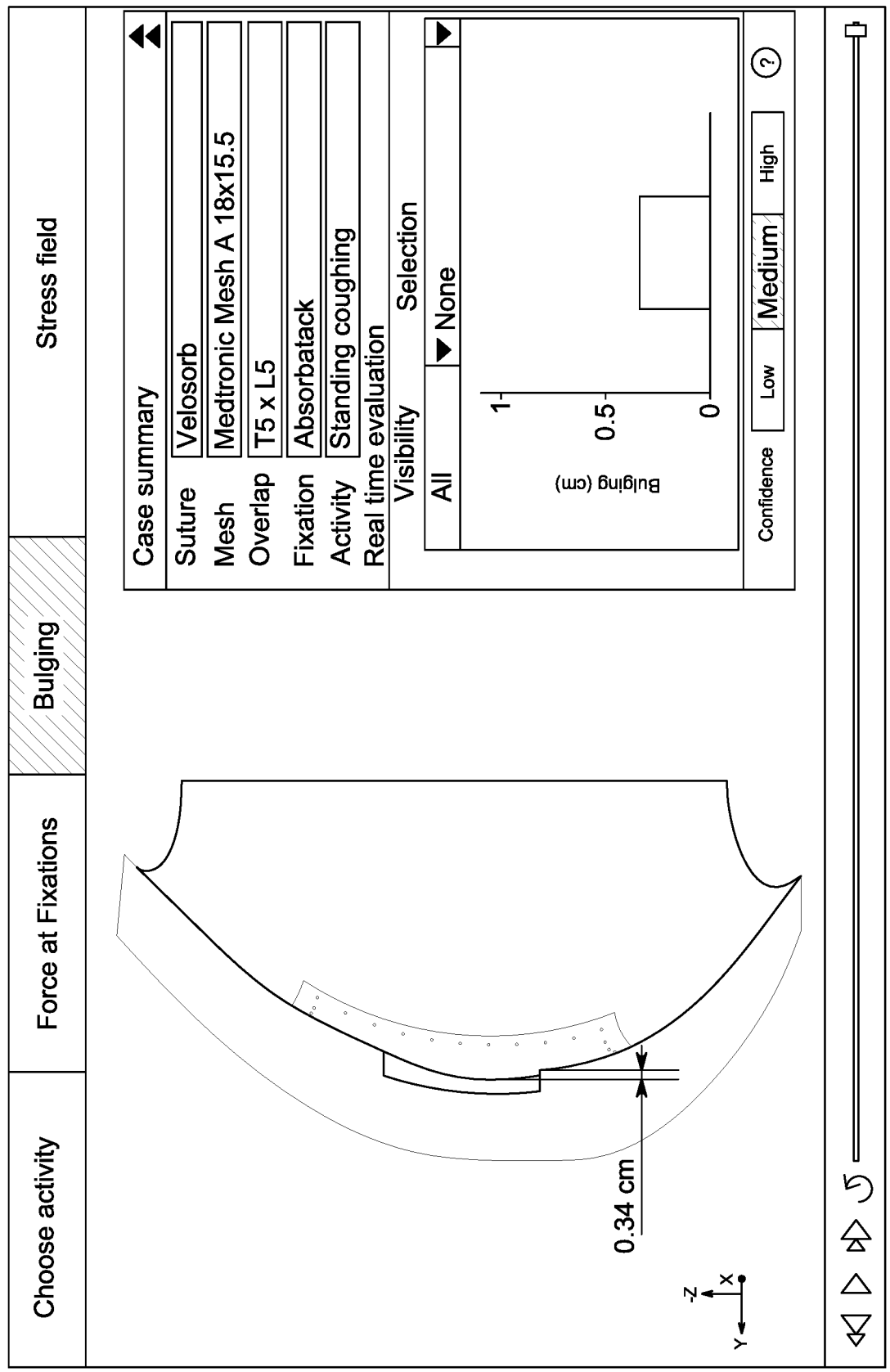
Figure 30C:
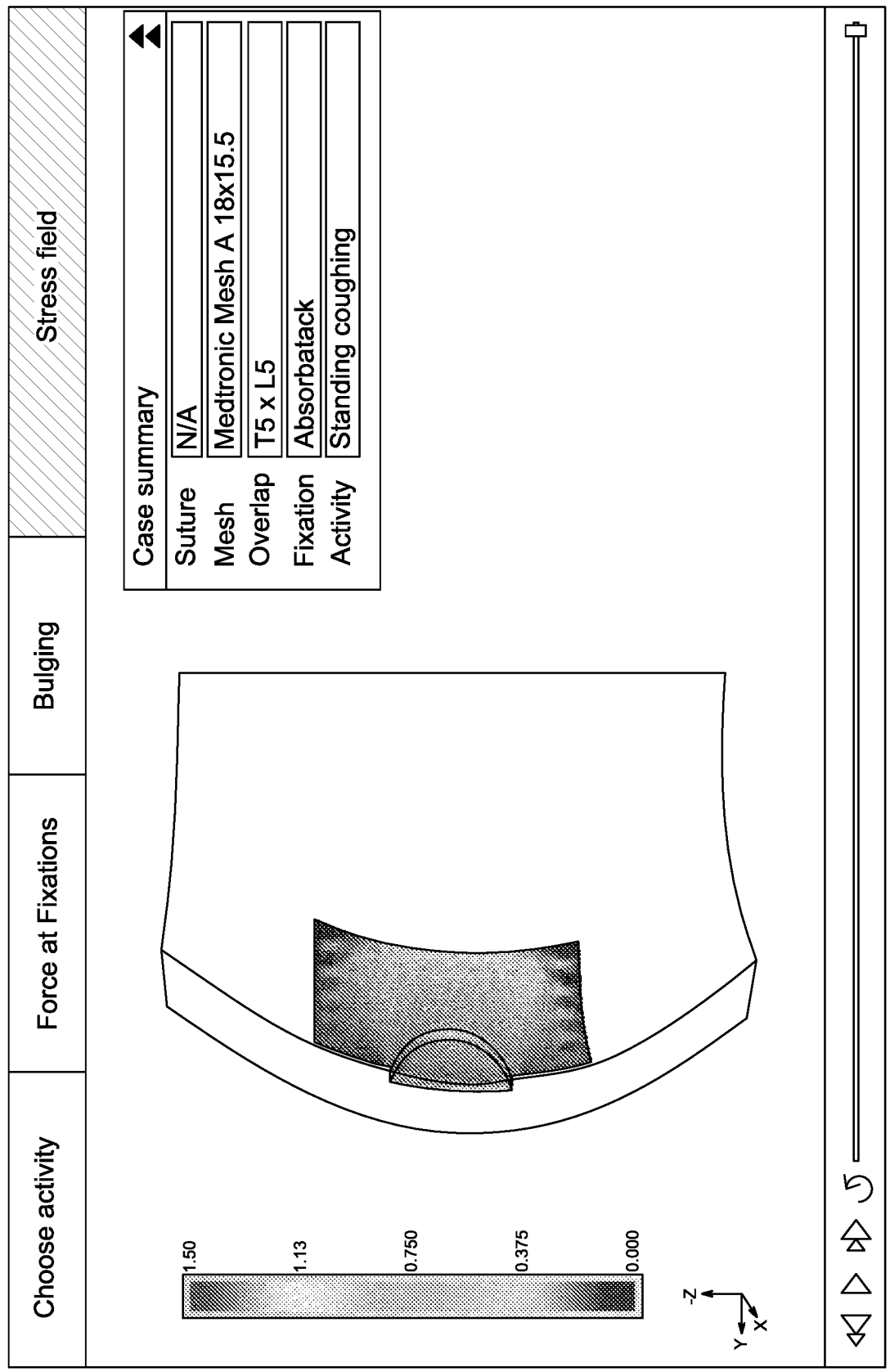

In step 250, an observable simulation is generated using the interactive 3D model, as shown in FIGS. 30A-30C. The observable simulation is based on the indications, selections, information, and/or data provided or confirmed in any one or more of steps 210-240, a summary of which may be displayed alongside the observable simulation, as shown in FIGS. 30A-30C. The summary serves to provide the clinician some context relating to the simulation. For example, the summary may include a patient name, particulars of an implanted hernia mesh or suture, overlap, fixation, and patient activity. However, the clinician at this time, or at any time, has the capability to freely navigate through the user interface 118 to update, edit, or change any indications, selections, information, and/or data provided during any one or more steps of method 200, which will be reflected in the observable simulation accordingly (e.g., changing the patient activity from sitting to jumping, changing the morphotype from ectomorph to mesomorph, changing the approach technique from onlay to Preperitoneal).

The observable simulation provides the clinician the capability to observe the effect on a tissue defect repaired by an implanted repair material (e.g., hernia mesh, suture, prophylactic onlay mesh, etc.) given the performance of the patient activity indicated in step 240. Additionally, the observable simulation provides a clinician the capability to observe the interaction between the patient tissue and the implanted repair material given the performance of the patient activity indicated in step 240. For example, the clinician may choose to generate a simulation of (1) how and to what extent the indicated patient activity affects the force at the fixations securing a mesh to the abdominal wall of the patient (FIG. 30A), (2) how and to what extent the indicated patient activity causes bulging of the mesh (FIG. 30B), or (3) how and to what extent the indicated patient activity causes a stress field on the mesh (FIG. 30C). For example, in the instance of incision or defect closure, the clinician may choose to generate a simulation of how and to what extent the indicated patient activity affects the force within the suture yarn or at the suture stitches.

In some embodiments, the clinician may choose to forego indicating a patient activity in step 240. In this embodiment, the application 116 may generate an observable model of an implantable repair material (e.g., hernia mesh) secured to the abdominal wall of the patient without generating the simulation described below with reference to FIGS. 30A-30C. For example, upon generating or indicating a surgery plan in step 230, the application 116 may generate the observable model as shown in FIGS. 30A-30C including a depiction of the indicated fixations in the indicated distribution about the implantable repair material.

Referring generally to FIGS. 30A-30C, the observable simulation may be generated by animating the 3D model using varying colors and/or varying pixel intensities on the display 110 to indicate force, stress, bulging at particular locations, such as fixation points, on the 3D model. Additionally, the clinician has the option to start and stop the simulation and to manipulate the interactive 3D model through the user interface 118 substantially as described above with respect to step 220. More specifically, the clinician may interact with the observable simulation via the user interface 118 to specify locations on the mesh (e.g., specific fixation points) or locations on the suture (e.g., in the case of using an augmentation technique with a mesh or a suture to close an incision) at which the clinician wishes to view an effect (e.g., force, stress, and/or bulging) of a given patient activity on those particular locations. The clinician may also choose to select/deselect specific locations on the mesh or suture either by using a menu (e.g., a pull-down menu) that lists the specific locations or by directly selecting/deselecting the specific locations with an input device (e.g., mouse, touch screen) via the user interface 118. For each location specified, the resulting force, stress, and/or bulging at that location may be displayed numerically or graphically (e.g., via bar graph, arrows, force vectors, heat map, etc.) to aid in the clinician's analysis of the observable simulation, as detailed below.

Referring to FIG. 30A, a simulation of the force at the fixations securing a mesh to the abdominal wall of the patient is shown and is based on the indications, selections, information, and/or data provided or confirmed in any one or more of steps 210-240. For example, the simulation of the force at fixations may illustrate the effect of a patient activity on the pull-out force applied at each individual fixation. While FIGS. 30A-30C describe generating an observable simulation in terms of observing a mesh secured to tissue, the observable simulation may also be generated in terms of observing a suture secured to tissue. In the example illustrated in FIG. 30A, a "case summary" of the currently generated simulation is displayed alongside the observable simulation and includes a suture type, mesh type and size (or suture type and size), overlap measurements, fixation type, and patient activity, all of which were previously indicated and/or confirmed by the clinician. Additionally, the summary includes a "real time evaluation" allowing the clinician to interact with the observable simulation. More specifically, a "visibility" menu (e.g., a pull-down menu) serves to allow the clinician to choose specific anatomical structures to be visible or invisible during the observable simulation. Anatomical structures may include, but are not limited to, fat, linear alba, skin, pelvis, ribs, spine, rectus muscle, rectus sheath, external oblique, internal oblique, and transversus. Additionally, the clinician may use a "selection" menu (e.g., a pull-down menu) to select specific fixation points (indicated in FIG. 30A by numbers superimposed on the 3D model) or groups of fixation points to observe the force at those particular fixations. The clinician may also mouse-click directly on the 3D model to select/deselect specific fixation points in lieu of or in conjunction with the "selection" menu. As illustrated in FIG. 30A, the force at each selected fixation point may be graphically represented in real time. The ability of the clinician to observe the force at fixation for any or all of the individual fixation points, allows the clinician to identify which fixation points are being subjected to the highest forces and compare these forces as numerical values to experimental data stored in the memory 102 to assess performance (e.g., weather bulging is detectable or undetectable) and the risks of failure (e.g., tear in the mesh, fixation pull out, etc.). The clinician may decide to modify the surgical plan via the user interface 118 in a manner intended to reduce the risk to an acceptable level and increase the safety factor to the expected level by minimizing the forces at those identified points, e.g., by using a double crown fixation technique, and generate a new simulation based on the modified surgical plan. More specifically, the clinician is able to seamlessly navigate through the user interface 118 at any time to modify any one or more indications, selections, information, and/or data provided or confirmed in any one or more of steps 210-240 to generate multiple different simulations. As detailed below, the results of multiple simulations may be presented to the clinician via the user interface 118 such that the clinician may compare simulation results side-by-side and evaluate which corresponding surgical plan should be utilized.

Referring to FIG. 30B, a simulation of how and to what extent the indicated patient activity causes bulging of the mesh is shown and is based on the indications, selections, information, and/or data provided or confirmed in any one or more of steps 210-240. A depiction of the distance the mesh is bulging may be shown and is depicted by way of example in FIG. 30B as "0.34 cm"). Similar to the example illustrated in FIG. 30A, the example illustrated in FIG. 30B also includes a "case summary" of the currently generated simulation displayed alongside the observable simulation and may include a suture type, mesh type and size (or suture type and size), overlap measurements, fixation type, and patient activity, all of which were previously indicated and/or confirmed by the clinician or otherwise based on a clinical profile provided to the computing device 100. Additionally, the summary includes a "real time evaluation" allowing the clinician to interact with the observable simulation substantially as describe above with respect to FIG. 30A. The clinician may decide to modify the surgical plan via the user interface 118 in a manner intended to minimize bulging by using an increased number of fixations, and generate a new simulation based on the modified surgical plan. More specifically, the clinician is able to seamlessly navigate through the user interface 118 at any time to modify any one or more indications, selections, information, and/or data provided or confirmed in any one or more of steps 210-240 to generate multiple different simulations. As detailed below, the results of multiple simulations may be presented to the clinician via the user interface 118 such that the clinician may compare simulation results side-by-side and evaluate which corresponding surgical plan should be utilized.

Referring to FIG. 30C, a simulation of how and to what extent the indicated patient activity causes a stress field on the mesh, on particular zones of the mesh, and/or on individual fixation points securing the mesh to tissue is shown and is based on the indications, selections, information, and/or data provided or confirmed in any one or more of steps 210-240. Similar to the examples illustrated in FIGS. 30A and 30B, the example illustrated in FIG. 30C includes a "Case summary" of the currently generated simulation displayed alongside the observable simulation and includes a suture type, mesh type and size (or suture type and size), overlap measurements, fixation type, and patient activity, all of which were previously generated by the application 116, indicated or confirmed by the clinician. The simulation may include color coding the 3D model to correspond to a color coded scale (depicted on the left side of FIG. 30C as ranging between "0.000" and "1.50") using a range of colors to indicate the magnitude of the stress field on tissue at specific locations of the repair site. For example, the color coded scale may range from the color blue, indicating a weak stress field, to a the color red, indicating a strong stress field. The ability of the clinician to observe the stress field at any or all zones of the mesh, allows the clinician to identify which zones of the mesh are most affected by the stress field. The clinician may decide to modify, via the user interface 118, the surgical plan in a manner intended to minimize the stress field at those identified zones, e.g., by using a larger mesh or different mesh type, and generate a new simulation based on the modified surgical plan. More specifically, the clinician is able to seamlessly navigate through the user interface 118 at any time to modify any one or more indications, selections, information, and/or data provided or confirmed in any one or more of steps 210-240 to generate multiple different simulations. As discussed in greater detail below, the results of multiple simulations may be presented to the clinician via the user interface 118 such that the clinician may compare simulation results side-by-side and evaluate which corresponding surgical plan should be utilized.

Additionally, although not shown in FIG. 30C, the summary may include a "real time evaluation" allowing the clinician to interact with the observable simulation substantially as describe above with respect to FIGS. 30A and 30B.

With continued reference to FIGS. 30A-30C, a confidence level (e.g., very low, low, standard, high, very high, etc.) may be generated automatically by the application 116 to indicate a level of confidence in each of the generated simulations described above with respect to FIGS. 30A-30C. A generated confidence level may be stored in connection with the simulation for later use as an indicator of confidence in that particular simulation. Simulations, indicated confidence levels, and corresponding clinical profiles, biomechanical profiles, and surgical plans may be stored in the memory 102 of computing device 100 and/or on a remote server (e.g., a hospital server) through use of the network interface 108.

Figure 31A:
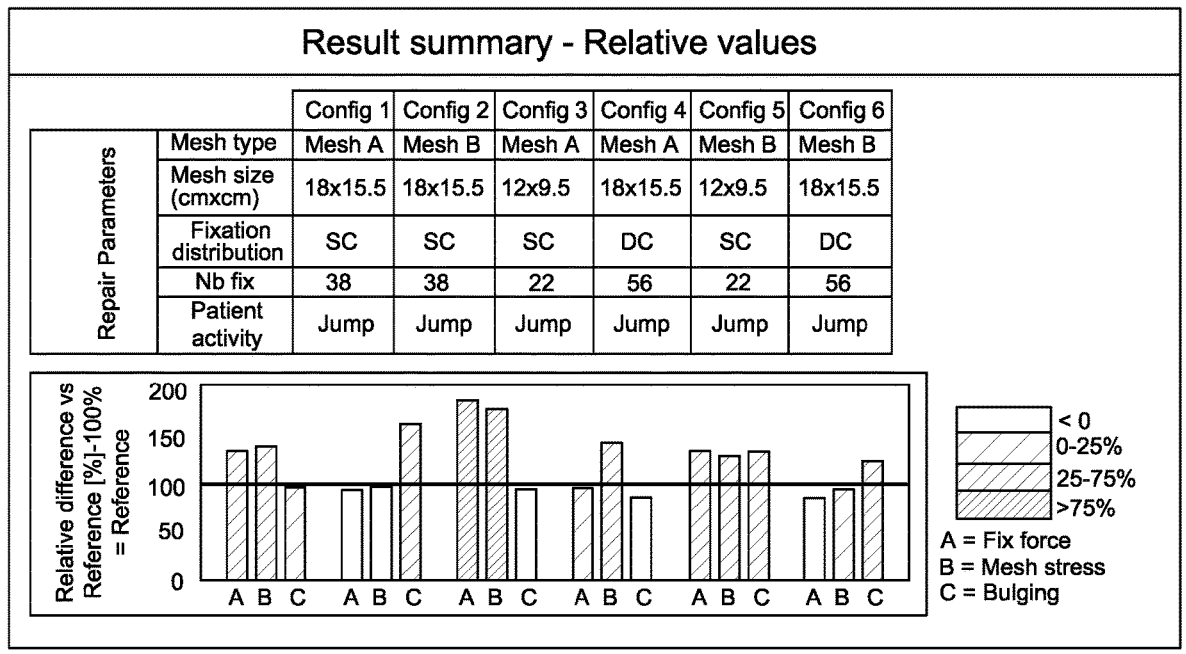
FIGS. 31A and 31B are illustrations of a user interface showing a step of generating an analysis report of the simulations of FIGS. 30A-30C in accordance with an embodiment of the present disclosure.
Figure 31B:
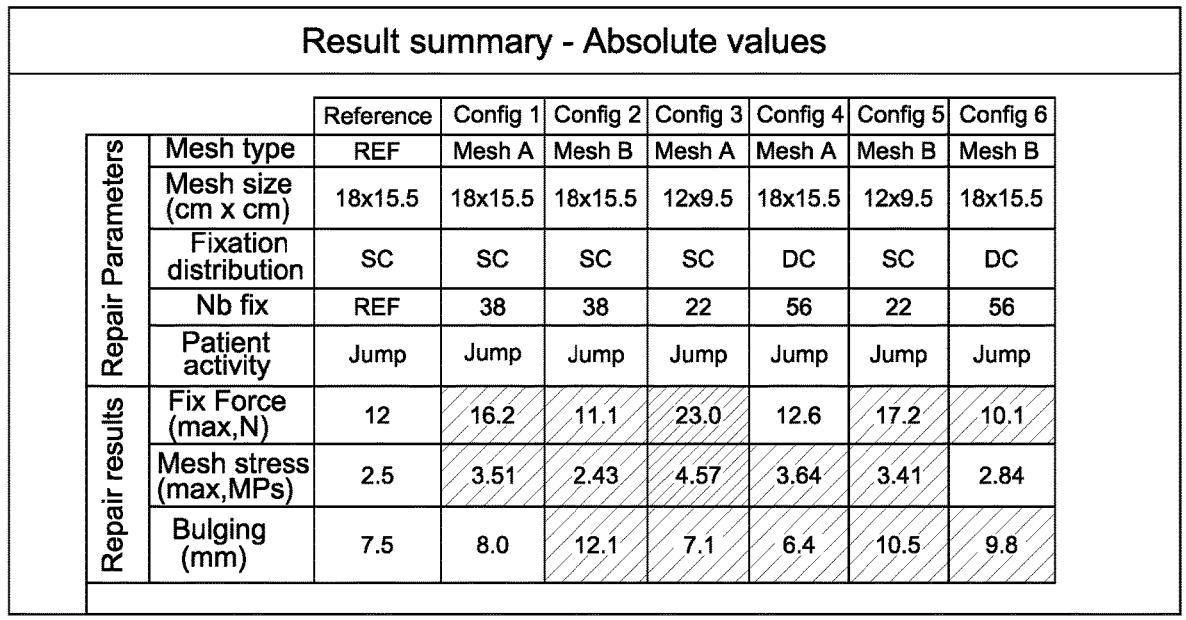
Figure 32B:
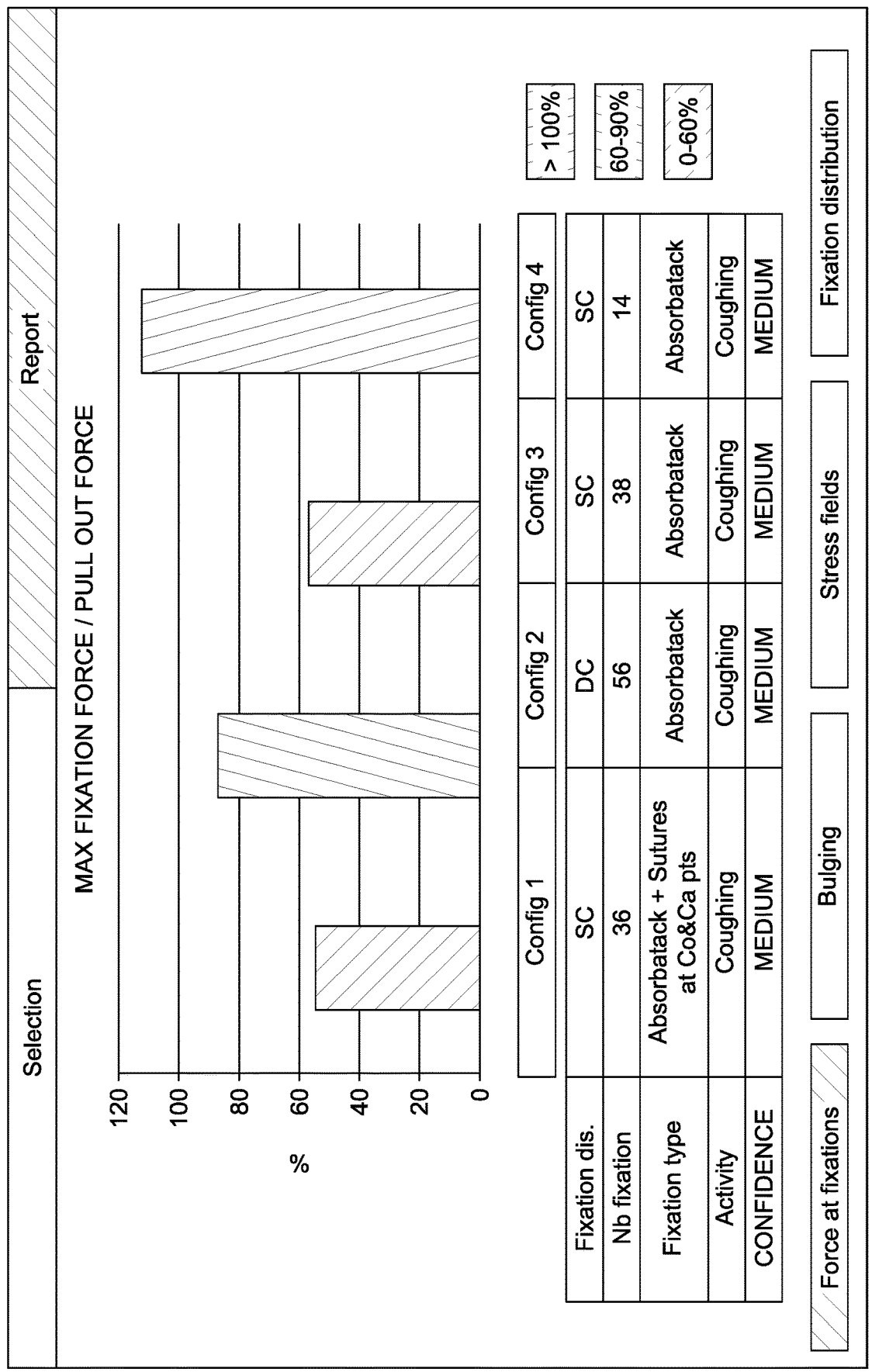
Figure 32C:
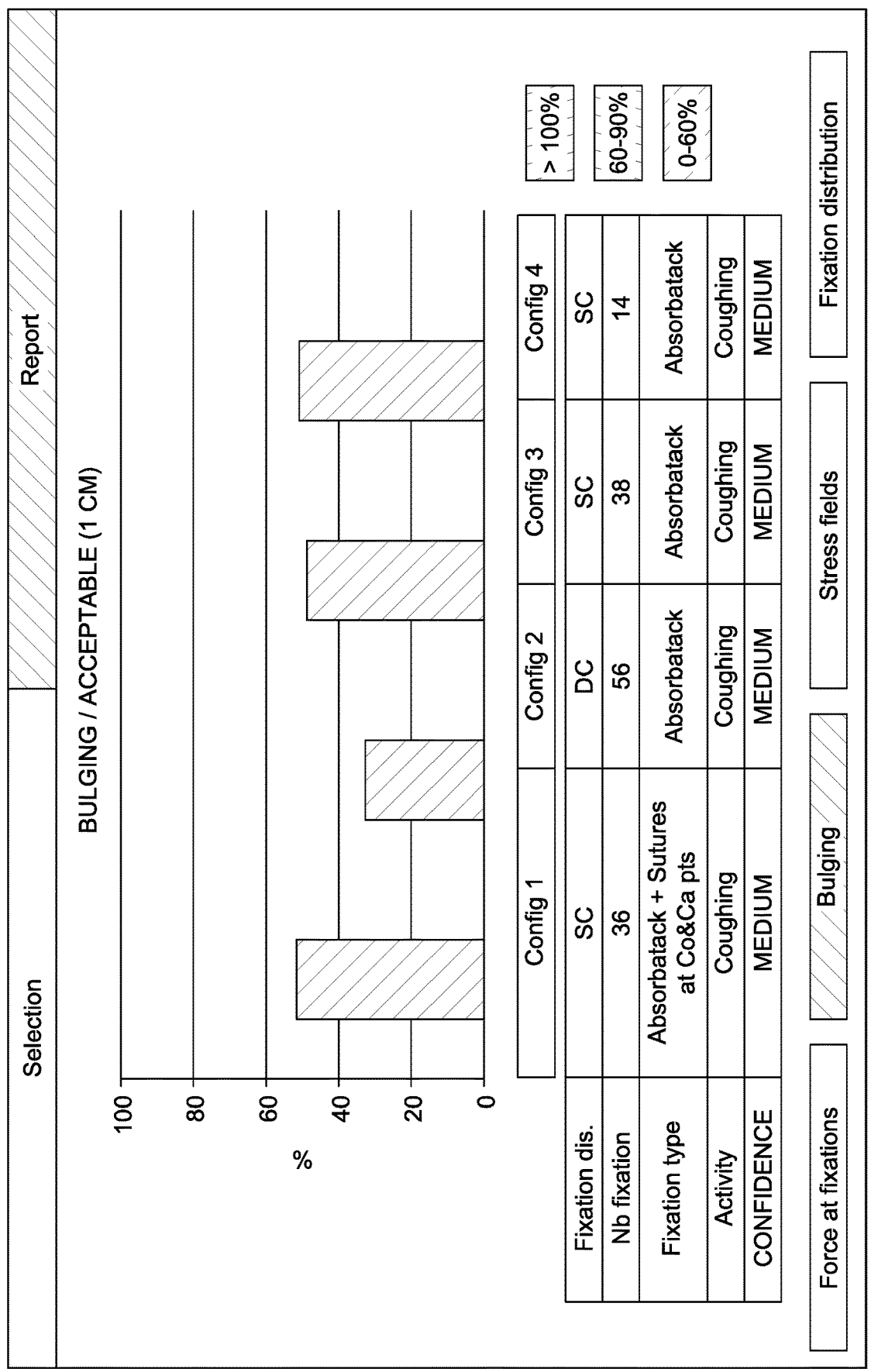
Figure 32D:
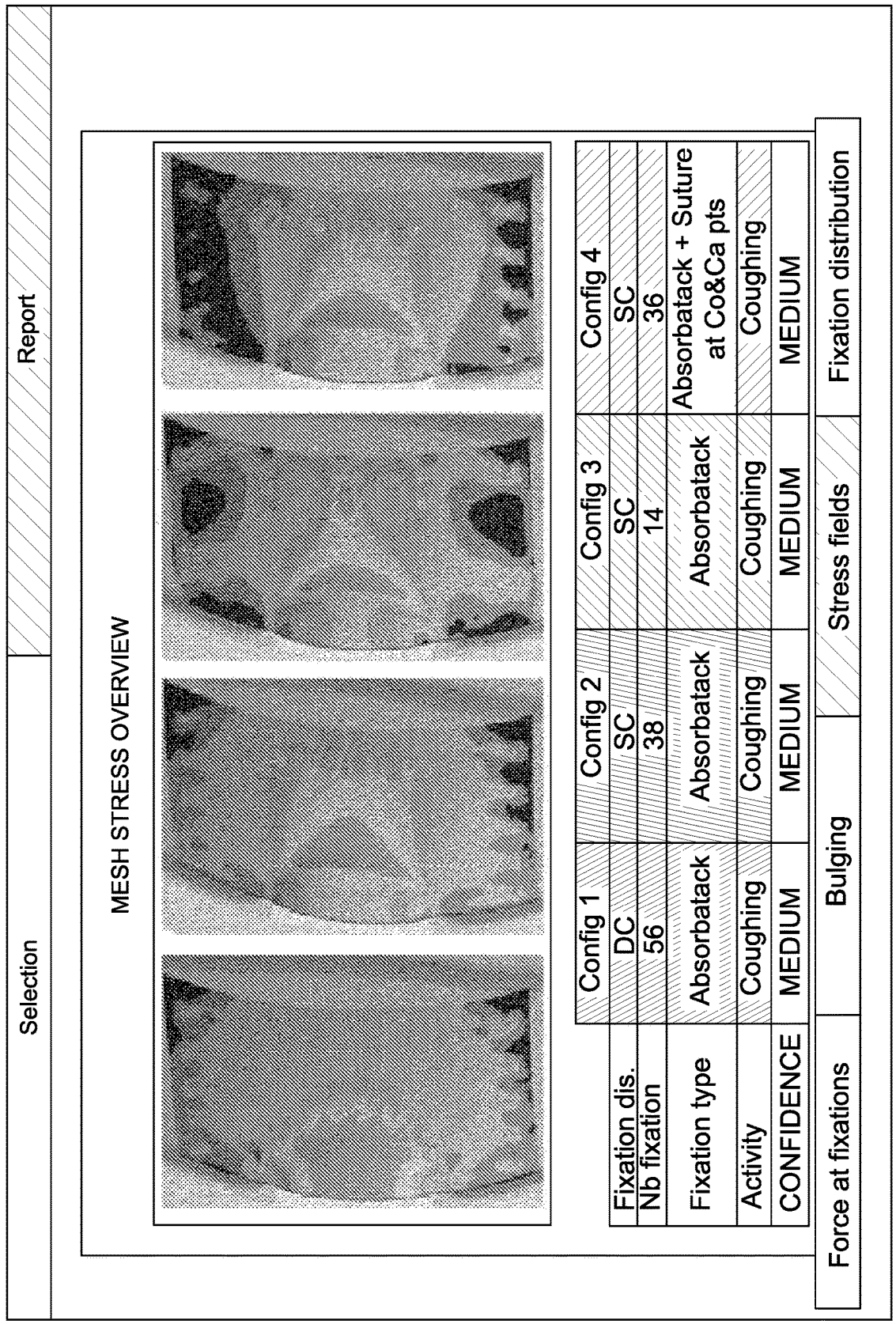
Figure 32E:
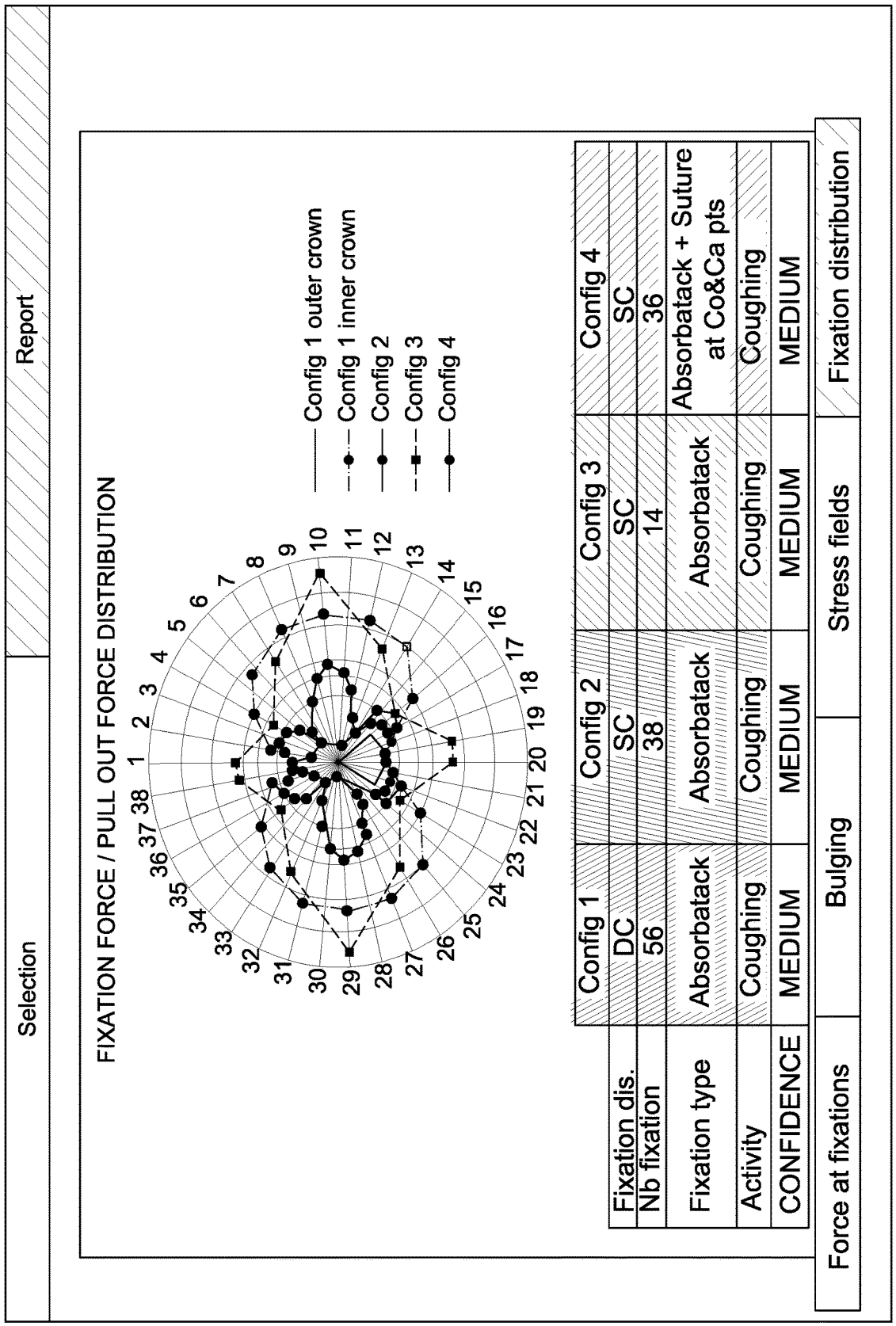
Figure 33A:
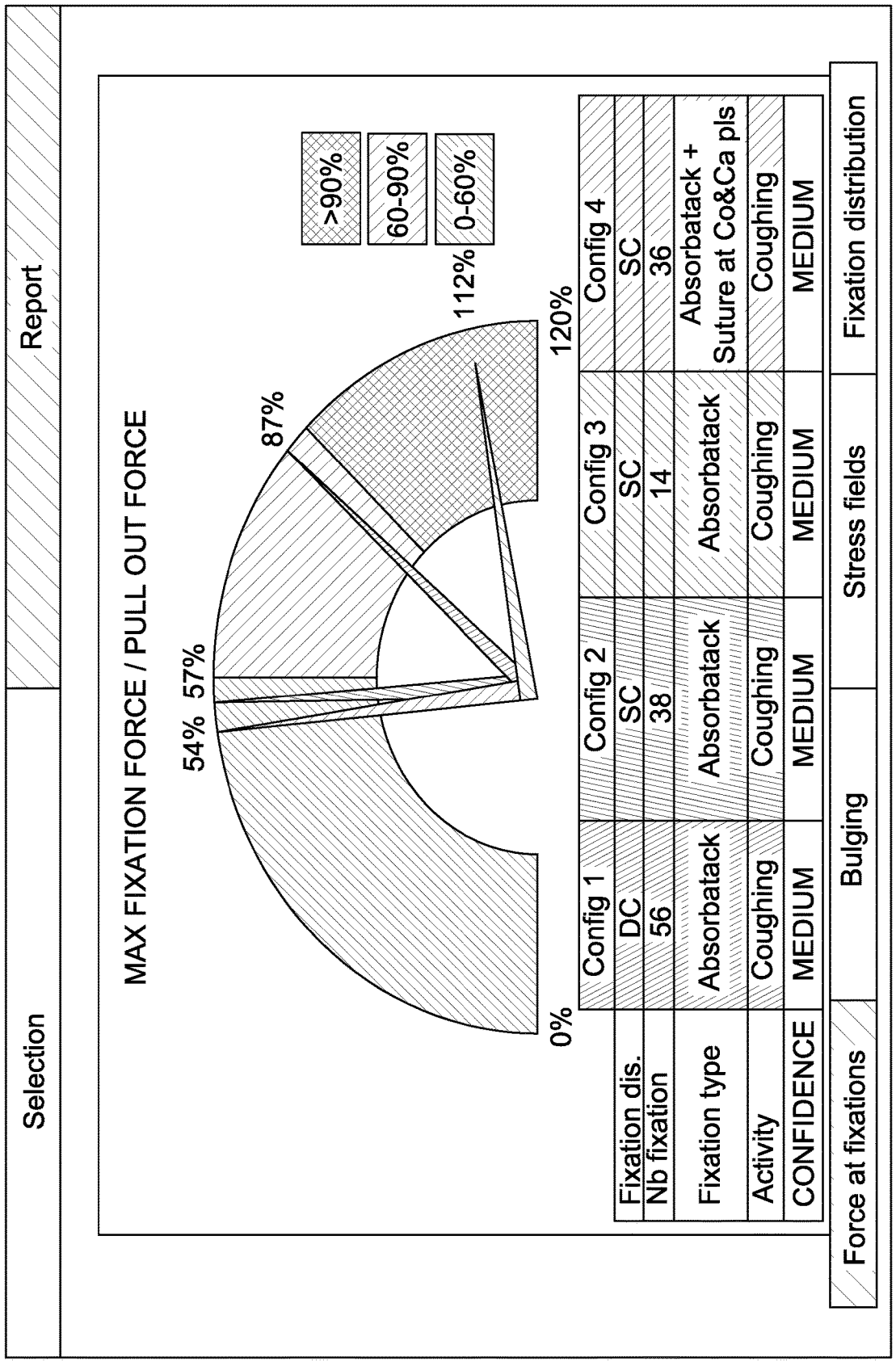
FIGS. 33A and 33B are illustrations of a user interface showing a step of generating an analysis report of the simulations of FIGS. 30A-30C in accordance with yet another embodiment of the present disclosure.
Figure 33B:
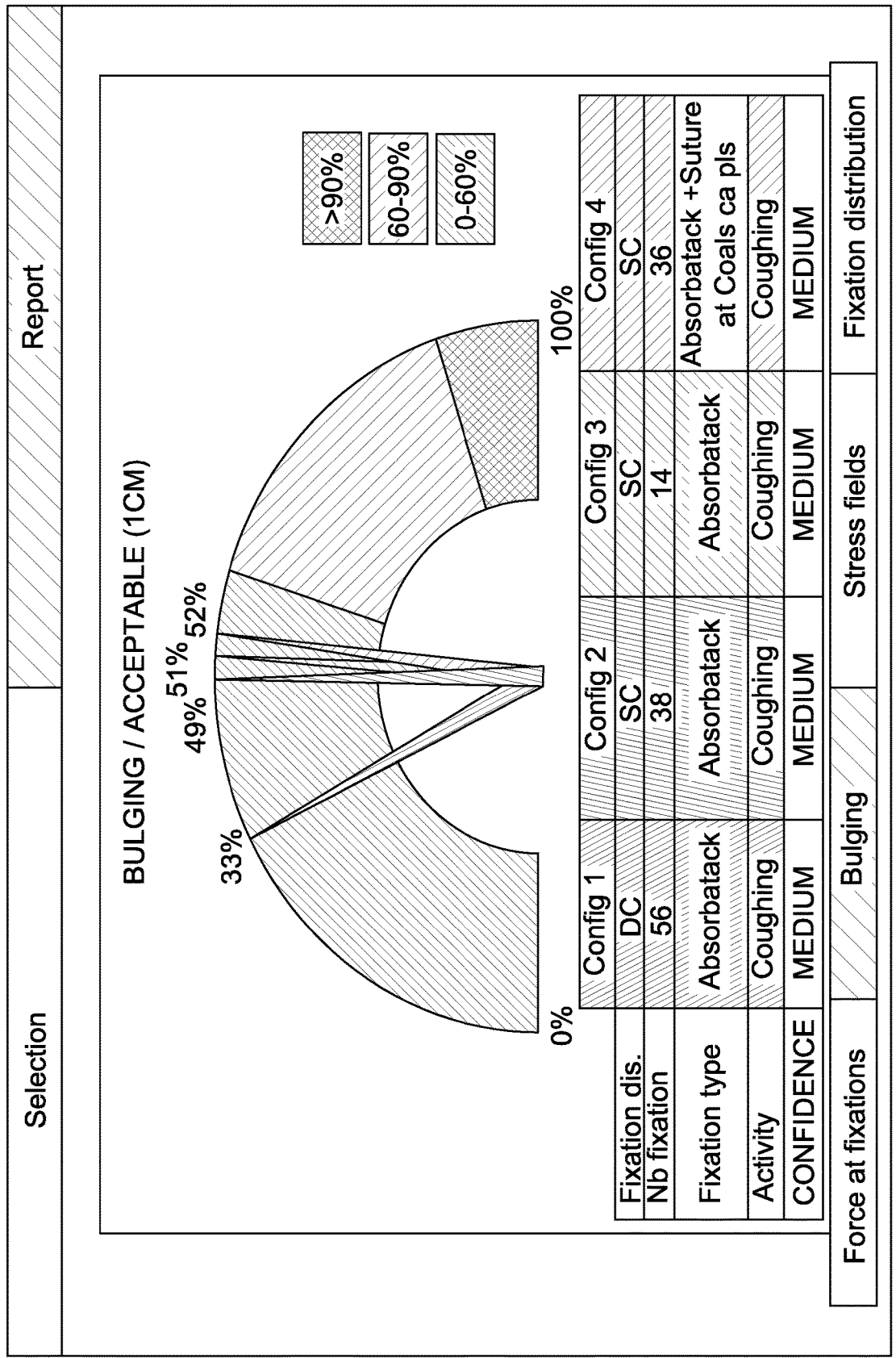

Step 260 includes generating analysis of the simulation or simulations based on the specifics of each generated simulation, as shown in FIGS. 31A and 31B in accordance with one embodiment of the present disclosure, as shown in FIGS. 32A-32E in accordance with another embodiment of the present disclosure, or as shown in FIGS. 33A and 33B in accordance with another embodiment of the present disclosure.

Referring to the embodiment illustrated in FIGS. 31A and 31B, the generated analysis may be in the form of a report including a summary of any one or more of the repair indications made by the clinician or by default as well as the resulting simulation results such as force at fixation, bulging, and stress field. The report may serve to compare the resulting simulation results of a plurality of repair material configurations. For example, simulation results for various mesh configurations (e.g., mesh type, mesh size, fixation distribution) are shown for purposes of comparison to aid the clinician in choosing an optimal mesh configuration. Referring specifically to FIG. 31A, the report may include relative results, wherein the simulation results for each repair material configuration is illustrated relative to a known optimal value. The known optimal value may be derived from experimental data stored in the memory 102. Experimental data may include stress threshold (e.g., threshold at which a mesh tears), maximum fixation pull out force, acceptable amount of bulging (e.g., visually undetectable). The known optimal value may be calculated by analyzing historical data of previous generated simulations and/or surgical repair procedures that have produced particular results. Additionally, the generated confidence level in a simulation, as described above with respect to FIGS. 30A-30C, may affect the optimal value. The known optimal value (depicted in FIG. 31A as a horizontal line) may be shown relative to a plot (e.g., bar graph) of the simulation results for purposes of comparison. Additionally, various schemes may be employed to indicate a deviation from the known optimal value for each simulation parameter (e.g., the results may be color coded).

Referring specifically to FIG. 31B, the report may also include absolute results such that the simulation results for each implantable repair material configuration are illustrated as an absolute value. For example, the force at fixation result may be indicated as a number value expressed in Newtons (N).

Referring now to the embodiment illustrated in FIGS. 32A-32E, the clinician is presented with a list of previously generated simulations (FIG. 32A) stored in the memory 102 of the computing device 100 and/or on a remote server. The clinician may select any one or more of the listed simulations to generate a report summarizing the simulation(s) side-by side (FIGS. 32B-32E). For example, FIG. 32B illustrates a report based on all of the generated simulations listed in FIG. 32A for the force at fixations (described above with respect to FIG. 30A), which may include absolute values for each force at fixations and a percentage of the force at fixations relative to a threshold force value. For each simulation, the report includes parameters such as the fixation distribution, the number of fixations, the fixation type, the indicated patient activity, and the confidence level in the simulation indicated by the clinician. Additionally, for each simulation, the report graphically represents the maximum fixation force. The report illustrated as a bar graph in FIG. 32B may alternatively or additionally be illustrated as a gauge type report as illustrated in FIG. 33A.

FIG. 32C illustrates a report based on all of the simulations listed in FIG. 32A for tissue bulging (described above with respect to FIG. 30B). For each simulation, the report includes parameters such as the fixation distribution, the number of fixations, the fixation type, the indicated patient activity, and the confidence level in the simulation indicated by the clinician. Additionally, for each simulation, the report graphically represents bulging as a percentage of an acceptable maximum bulging. The report serves to provide the clinician with side-by-side results of multiple simulations of bulging such that the clinician may evaluate which corresponding surgical plan should be utilized. The report illustrated as a bar graph in FIG. 32C may alternatively or additionally be illustrated as a gauge type report as illustrated in FIG. 33B.

FIG. 32D illustrates a report based on all of the simulations listed in FIG. 32A for stress fields (described above with respect to FIG. 30C). For each simulation, the report includes parameters such as the fixation distribution, the number of fixations, the fixation type, the indicated patient activity, and the confidence level in the simulation indicated by the clinician. Additionally, for each simulation, the report may represent stress fields using color-coded heat maps to help the clinician visualize the concentration of the stress fields. The report serves to provide the clinician with side-by-side results of multiple simulations of stress fields such that the clinician may evaluate which corresponding surgical plan should be utilized.

FIG. 32E illustrates a report based on all of the simulations listed in FIG. 32A for the force distribution at the fixation points previously indicated or confirmed by the clinician and used to contribute to generating each simulation. For each generated simulation selected, the report includes parameters such as the force distribution at the fixation points, the number of fixations, the fixation type, the indicated patient activity, and the confidence level in the simulation. Additionally, for each simulation, the report graphically represents the force distribution at the fixation points using line graphs plotted along the fixation points, as shown in FIG. 32E. The report serves to provide the clinician with side-by-side fixation distribution configurations used for multiple generated simulations such that the clinician may evaluate which corresponding fixation distribution configuration should be utilized.

It should be understood that any of the above-described steps 210-260 are not necessarily order specific, in that the clinician may have the capability to perform any one of steps 210-260 or any actions described hereinabove as being associated with steps 210-260 at any time during method 200. For example the clinician may skip any one of steps 210-260 or repeat the performance of any one of steps 210-260.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

For example, according to another embodiment of the present disclosure, a method of generating a computer-based observable model of an implantable repair material secured to a patient is provided. The method includes generating an observable model of the implantable repair material secured to the patient on a display operably associated with a computing device. The observable model depicts an indicated distribution of a fixation about the implantable repair material.

According to one aspect of the above-described embodiment, the method also includes processing data corresponding to a patient using the computing device. The computing device includes a processor and a memory storing a software application executable by the processor.

According to another aspect of the above-described embodiment, the method also includes indicating the implantable repair material and the distribution of the fixation about the implantable repair material for securing the implantable repair material to the patient.

According to yet another embodiment of the present disclosure, a system is provided for generating a computer-based observable model of an implantable repair material secured to a patient. The system includes a computing device including a processor and a memory storing a software application which, when executed by the processor, cause the computing device to perform a method. The method includes generating an observable model of the implantable repair material secured to the patient on a display operably associated with a computing device. The observable model depicts an indicated distribution of a fixation about the implantable repair material.

According to one aspect of the above-described embodiment, the method also includes processing data corresponding to a patient using the computing device.

According to another aspect of the above-described embodiment, the method also includes indicating the implantable repair material and the distribution of the fixation about the implantable repair material for securing the implantable repair material to the patient.

According to yet another embodiment of the present disclosure, a method of generating a computer-based observable model of a hernia mesh secured to a patient is provided. The method includes generating an observable model of the hernia mesh secured to the patient on a display operably associated with a computing device. The observable model depicts an indicated distribution of a fixation about the hernia mesh.

According to one aspect of the above-described embodiment, the method also includes processing data corresponding to a patient using the computing device. The computing device includes a processor and a memory storing a software application executable by the processor.

According to another aspect of the above-described embodiment, the method also includes indicating the hernia mesh and the distribution of the fixation about the hernia mesh for securing the hernia mesh to the patient.

According to yet another embodiment of the present disclosure, a method of generating a computer-based observable model of an implantable repair material secured to a patient is provided. The method includes generating an optimized distribution of a fixation about the implantable repair material when an abdominal wall of a patient is inflated at an optimized intra-abdominal pressure (IAP).

According to one aspect of the above-described embodiment, the method includes processing data corresponding to a patient using a computing device including a processor and a memory storing a software application executable by the processor.

According to another aspect of the above-described embodiment, the method includes indicating the implantable repair material and the fixation for securing the implantable repair material to the patient.

According to another aspect of the above-described embodiment, the method includes indicating a target distribution of the fixation about the implantable repair material when an abdominal wall of the patient is deflated.

According to another aspect of the above-described embodiment, the method includes generating the optimized IAP to which to insufflate the abdominal wall of the patient.

According to yet another embodiment of the present disclosure, a method of generating a computer-based observable model of an implantable repair material secured to a patient is provided. The method includes generating an optimized distribution of a fixation about the implantable repair material when an abdominal wall of a patient is inflated at an intra-abdominal pressure (IAP).

According to one aspect of the above-described embodiment, the method also includes processing data corresponding to a patient using a computing device. The computing device includes a processor and a memory storing a software application executable by the processor.

According to another aspect of the above-described embodiment, the method also includes indicating the implantable repair material and the fixation for securing the implantable repair material to the patient.

According to another aspect of the above-described embodiment, the method also includes indicating a target distribution of the fixation about the implantable repair material when the abdominal wall of the patient is deflated.

According to another aspect of the above-described embodiment, the method also includes indicating the IAP to which to insufflate the abdominal wall of the patient.

According to yet another embodiment of the present disclosure, a method of generating a computer-based observable model of an implantable repair material secured to a patient is provided. The method includes generating an actual distribution of a fixation about the implantable repair material when an abdominal wall of a patient is inflated at an intra-abdominal pressure (IAP).

According to one aspect of the above-described embodiment, the method also includes processing data corresponding to the patient using a computing device. The computing device includes a processor and a memory storing a software application executable by the processor.

According to another aspect of the above-described embodiment, the method also includes indicating the implantable repair material and the fixation for securing the implantable repair material to the patient.

According to another aspect of the above-described embodiment, the method also includes indicating a target distribution of the fixation about the implantable repair material when the abdominal wall of the patient is inflated.

According to another aspect of the above-described embodiment, the method also includes indicating the IAP to which to insufflate the abdominal wall of the patient.

According to yet another embodiment of the present disclosure, a method of generating a computer-based simulation of an effect of a patient activity on an implantable repair material secured to a patient is provided. The method includes indicating an activity to be performed by a patient and generating, on a display operably associated with a computing device, a simulation of an effect of the indicated activity on the implantable repair material secured to the patient.

Although the foregoing disclosure has been described in some detail by way of illustration and example, for purposes of clarity or understanding, it will be obvious that certain changes and modifications may be practiced within the scope of the appended claims.

What is claimed is:

1. A method of generating a computer-based observable model of an implantable repair mesh secured to a tissue of a patient, comprising:
   processing data corresponding to a patient using a computing device including a processor and a memory storing a software application executable by the processor;
   indicating an implantable repair mesh and a fixation for securing the implantable repair mesh to the tissue of the patient;
   indicating a distribution of the fixation about the implantable repair mesh;
   generating a computer-based interactive observable model of the implantable repair mesh secured to the tissue of the patient based on the indicated implantable repair mesh, the indicated fixation, and the indicated distribution of the fixation; and
   displaying, on a display operably associated with the computing device, the computer-based interactive observable model depicting the indicated distribution of the fixation about the implantable repair mesh.

2. The method according to claim 1, further comprising: indicating an activity to be performed by the patient; and generating, on the display, a simulation of an effect of the indicated activity on the implantable repair mesh secured to the tissue of the patient.

3. The method according to claim 2, wherein the effect of the indicated activity on the implantable repair mesh is selected from the group consisting of a force at the fixation securing the implantable repair mesh to the patient, bulging of the implantable repair mesh, and a stress field on the implantable repair mesh.

4. The method according to claim 1, wherein the data corresponding to the patient includes a clinical profile of the patient.

5. The method according to claim 1, wherein at least one of the implantable repair mesh, the fixation, or the distribution of the fixation about the implantable repair mesh is generated by the software application.

6. The method according to claim 1, wherein at least one of the implantable repair mesh, the fixation, or the distribution of the fixation about the implantable repair mesh is selected through an user interface of the computing device.

7. The method according to claim 1, wherein the observable model is generated in 3D.

8. The method according to claim 1, wherein the observable model is generated by the software application.

9. The method according to claim 1, wherein the observable model is selected through an user interface of the computing device.

10. The method according to claim 1, further comprising indicating a placement technique selected from the group consisting of onlay, inlay, retromuscular, preperitoneal, and intraperitoneal.

11. The method according to claim 1, further comprising indicating a technique for tissue release selected from the group consisting of transversus abdominis muscle release (TAR) and component separation.

12. The method according to claim 1, further comprising indicating a type of defect repair as one of augmentation or bridging.

13. The method according to claim 1, further comprising indicating a morphotype of the patient.

14. The method according to claim 1, further comprising indicating a surgical approach for securing the implantable repair mesh to the tissue of the patient as one of an open surgical approach or a laparoscopic surgical approach.

15. The method according to claim 1, wherein generating the observable model is based on at least one of the processed data, the indicated implantable repair mesh, the indicated fixation, or the indicated distribution of the fixation.

16. The method according to claim 2, wherein generating the simulation is based on at least one of the processed data, the indicated implantable repair mesh, the indicated fixation, the indicated distribution of the fixation, or the indicated activity to be performed by the patient.

17. The method according to claim 1, wherein the implantable repair mesh is a hernia mesh.

18. The method according to claim 1, wherein the fixation for securing the implantable repair mesh to the tissue of the patient is at least one of a tack, a suture, glue, a strap, or a staple.

19. The method according to claim 1, wherein the fixation for securing the implantable repair mesh to the tissue of the patient is a tack.

20. The method according to claim 1, wherein the fixation for securing the implantable repair mesh to the tissue of the patient is a suture.

21. The method according to claim 1, wherein the fixation for securing the implantable repair mesh to the tissue of the patient is glue.

22. The method according to claim 1, wherein the fixation for securing the implantable repair material to the tissue of the patient is a staple.

23. A system for generating a computer-based observable model of an implantable repair mesh secured to a tissue of a patient, the system comprising:

a computing device including a processor and a memory storing a software application which, when executed by the processor, cause the computing device to perform a method, comprising:

processing data corresponding to a patient using the computing device;

indicating an implantable repair mesh and a fixation for securing the implantable repair mesh to the tissue of the patient;

indicating a distribution of the fixation about the implantable repair mesh; and generating a computer-based interactive observable model of the implantable repair mesh secured to the tissue of the patient based on the indicated implantable repair mesh, the indicated fixation, and the indicated distribution of the fixation; and displaying, on a display operably associated with the computing device, the computer-based interactive observable model depicting the indicated distribution of the fixation about the implantable repair mesh.

24. The system according to claim 23, wherein the method further comprises:

indicating an activity to be performed by the patient; and generating, on the display, a simulation of an effect of the indicated activity on the implantable repair mesh secured to the tissue of the patient.

25. A method of generating a computer-based observable model of a hernia mesh secured to a tissue of a patient, comprising:

processing data corresponding to a patient using a computing device including a processor and a memory storing a software application executable by the processor;

indicating a hernia mesh and a distribution of a fixation about the hernia mesh for securing the hernia mesh to the tissue of the patient; and generating a computer-based interactive observable model of the hernia mesh secured to the tissue of the patient based on the indicated implantable repair mesh, the indicated fixation, and the indicated distribution of the fixation; and displaying, on a display operably associated with the computing device, the computer-based interactive observable model depicting the indicated distribution of the fixation about the hernia mesh.

26. The method according to claim 25, further comprising:

indicating an activity to be performed by the patient; and generating, on the display, a simulation of an effect of the indicated patient activity on the hernia mesh secured to the tissue of the patient.

27. The method according to claim 1, wherein indicating the implantable repair mesh, the fixation, and the distribution of the fixation includes providing input data specifying the implantable repair mesh, the fixation, and the distribution of the fixation.

* * * * *